(12) United States Patent
Van Schalkwyk et al.

(10) Patent No.: US 11,202,878 B2
(45) Date of Patent: Dec. 21, 2021

(54) VALVE MODULE AND FILTER

(71) Applicant: Fisher & Paykel Healthcare Limited, Auckland (NZ)

(72) Inventors: Andre Van Schalkwyk, Auckland (NZ); Stephen William Kavermann, Auckland (NZ); Jess Edward Donnelly, Auckland (NZ); Peter Geoffrey Hawkins, Auckland (NZ)

(73) Assignee: Fisher and Paykel Healthcare Limited, Auckland (NZ)

( * ) Notice: Subject to any disclaimer, the term of this patent is extended or adjusted under 35 U.S.C. 154(b) by 154 days.

(21) Appl. No.: 16/342,472

(22) PCT Filed: Oct. 18, 2017

(86) PCT No.: PCT/NZ2017/050136
§ 371 (c)(1),
(2) Date: Apr. 16, 2019

(87) PCT Pub. No.: WO2018/074935
PCT Pub. Date: Apr. 26, 2018

(65) Prior Publication Data
US 2019/0255276 A1 Aug. 22, 2019

Related U.S. Application Data

(60) Provisional application No. 62/409,543, filed on Oct. 18, 2016, provisional application No. 62/488,841, filed on Apr. 23, 2017.

(51) Int. Cl.
*A61M 16/10* (2006.01)
*A61M 16/12* (2006.01)
(Continued)

(52) U.S. Cl.
CPC ...... *A61M 16/105* (2013.01); *A61M 16/0066* (2013.01); *A61M 16/12* (2013.01);
(Continued)

(58) Field of Classification Search
CPC .. A61M 16/00; A61M 16/009; A61M 16/105; A61M 16/106; A61M 16/1065;
(Continued)

(56) References Cited

U.S. PATENT DOCUMENTS 4,928,684 A 5/1990 Breitenfelder et al.
6,024,087 A 2/2000 Kersey et al.
(Continued)

FOREIGN PATENT DOCUMENTS

DE 102006011151 9/2007
DE 202011107902 3/2012
(Continued)

OTHER PUBLICATIONS

Extended European Search Report, Application No. 17861903.7, dated May 13, 2020, 9 pages.
(Continued)

*Primary Examiner* — Joseph D. Boecker
(74) *Attorney, Agent, or Firm* — Knobbe, Martens, Olson and Bear LLC.

(57) ABSTRACT

A filter for an apparatus for delivering a flow of gas, the filter comprising: a filter body, wherein the filter body has a main compartment and a sub-compartment at least partly within the main compartment, wherein the main compartment is in fluid communication with a main compartment gases inlet and the sub-compartment is in fluid communication with a sub-compartment gases inlet; and a filter medium associated with both the main compartment and the sub-compartment, and that is arranged to filter gases in, or exiting, the main compartment and the sub-compartment.

26 Claims, 54 Drawing Sheets

(51) Int. Cl.
*A61M 16/16* (2006.01)
*A61M 16/20* (2006.01)
*A61M 16/00* (2006.01)
A61M 16/08 (2006.01)
A61M 16/06 (2006.01)

(52) U.S. Cl.
CPC .......... *A61M 16/125* (2014.02); *A61M 16/16* (2013.01); *A61M 16/161* (2014.02); *A61M 16/20* (2013.01); *A61M 16/203* (2014.02); *A61M 16/0672* (2014.02); *A61M 16/0825* (2014.02); *A61M 16/109* (2014.02); *A61M 16/1055* (2013.01); *A61M 16/1095* (2014.02); *A61M 16/202* (2014.02); *A61M 2016/0027* (2013.01); *A61M 2016/0039* (2013.01); *A61M 2202/025* (2013.01); *A61M 2202/0208* (2013.01); *A61M 2205/125* (2013.01); *A61M 2205/128* (2013.01); *A61M 2205/3331* (2013.01); *A61M 2205/3368* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/42* (2013.01); *A61M 2205/7518* (2013.01); *A61M 2205/7545* (2013.01); *A61M 2207/00* (2013.01)

(58) Field of Classification Search
CPC ............ A61M 16/107; A61M 16/1005; A61M 16/12; A61M 16/125; A61M 16/22; A61M 2205/75; B01D 2201/302; B01D 46/0002; B01D 46/0006; B01D 46/0009; B01D 46/0013
See application file for complete search history.

(56) References Cited

U.S. PATENT DOCUMENTS

| | | | |
|---|---|---|---|
| 6,035,851 A | 3/2000 | Wallen | |
| 6,217,627 B1 | 4/2001 | Vyskocil et al. | |
| 6,619,287 B2 * | 9/2003 | Blackhurst | A61M 16/1055 128/201.13 |
| 6,634,356 B1 | 10/2003 | O'Dea et al. | |
| 2004/0025484 A1 * | 2/2004 | Marchart | F02M 35/024 55/480 |
| 2004/0040274 A1 * | 3/2004 | Amann | B01D 46/521 55/498 |
| 2004/0134171 A1 * | 7/2004 | Scott | B01D 46/521 55/482 |
| 2006/0272639 A1 * | 12/2006 | Makinson | A61M 16/107 128/203.16 |
| 2008/0066752 A1 | 3/2008 | Baker et al. | |
| 2008/0076962 A1 | 3/2008 | Miyagawa et al. | |
| 2008/0196722 A1 * | 8/2008 | Kramer | A61M 16/16 128/204.22 |
| 2008/0283053 A1 * | 11/2008 | Zucchi | A61M 16/08 128/201.13 |
| 2009/0025564 A1 * | 1/2009 | Kuwabara | A61M 16/08 128/201.13 |
| 2010/0139657 A1 * | 6/2010 | Chalvignac | A61M 16/0057 128/204.22 |
| 2010/0242961 A1 | 9/2010 | Mougel et al. | |
| 2010/0313532 A1 | 12/2010 | Stjernfelt et al. | |
| 2011/0100362 A1 | 5/2011 | Baecke et al. | |
| 2011/0126832 A1 * | 6/2011 | Winter | A61M 16/206 128/204.21 |
| 2011/0023879 A1 | 12/2011 | Vandine et al. | |
| 2012/0285454 A1 | 11/2012 | Nibu et al. | |
| 2013/0023729 A1 * | 1/2013 | Vazales | A61M 16/0463 600/104 |
| 2013/0239968 A1 | 9/2013 | Friberg et al. | |
| 2014/0144446 A1 | 5/2014 | Bobey et al. | |
| 2015/0112246 A1 | 4/2015 | Palmerton et al. | |
| 2016/0082220 A1 * | 3/2016 | Barker | B01F 15/00207 128/203.12 |

FOREIGN PATENT DOCUMENTS

| | | | | |
|---|---|---|---|---|
| GB | 2450735 | | 1/2009 | |
| GB | 2450735 A | * | 1/2009 | .......... A61M 16/105 |
| WO | WO 2013/170290 | | 11/2013 | |
| WO | WO 2015/187986 | | 12/2015 | |

OTHER PUBLICATIONS

International Search Report, Application No. PCT/NZ2017/050136, dated Jan. 23, 2018, in 11 pages.
Search Report and Written Opinion; Singapore Patent Application No. 11201903239V; dated Jun. 16, 2020; 9 pages.

* cited by examiner

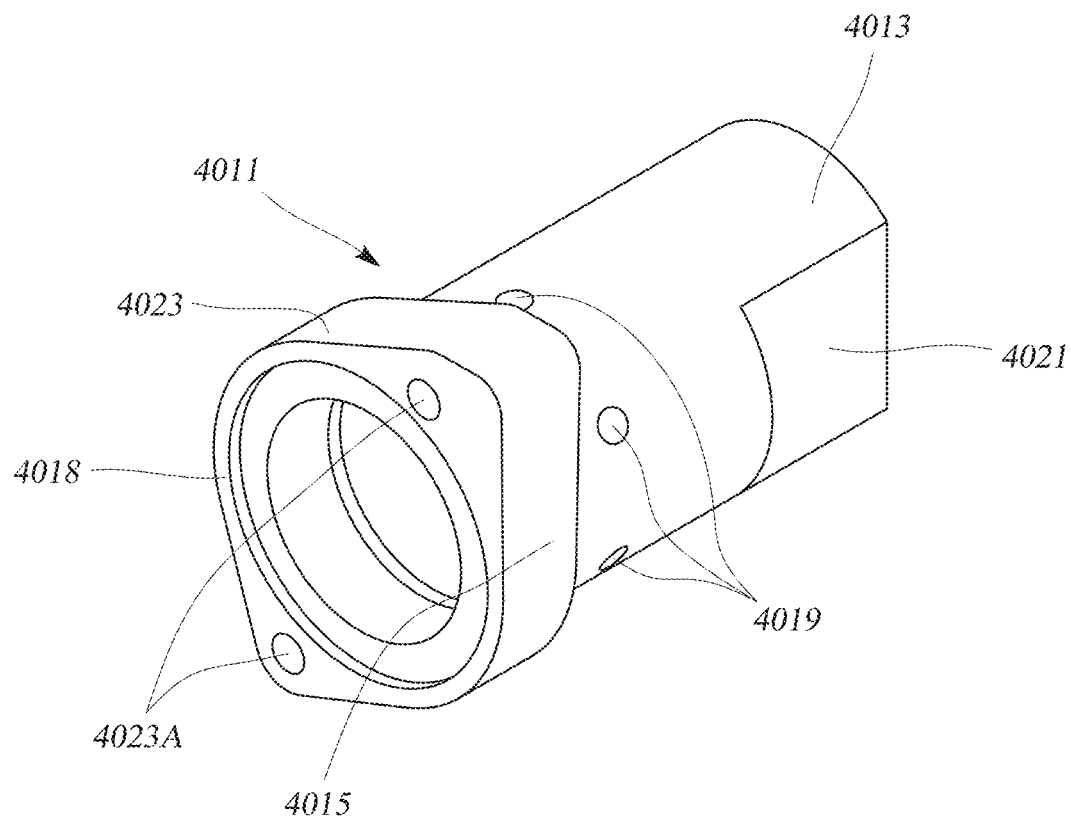
FIGURE 20A
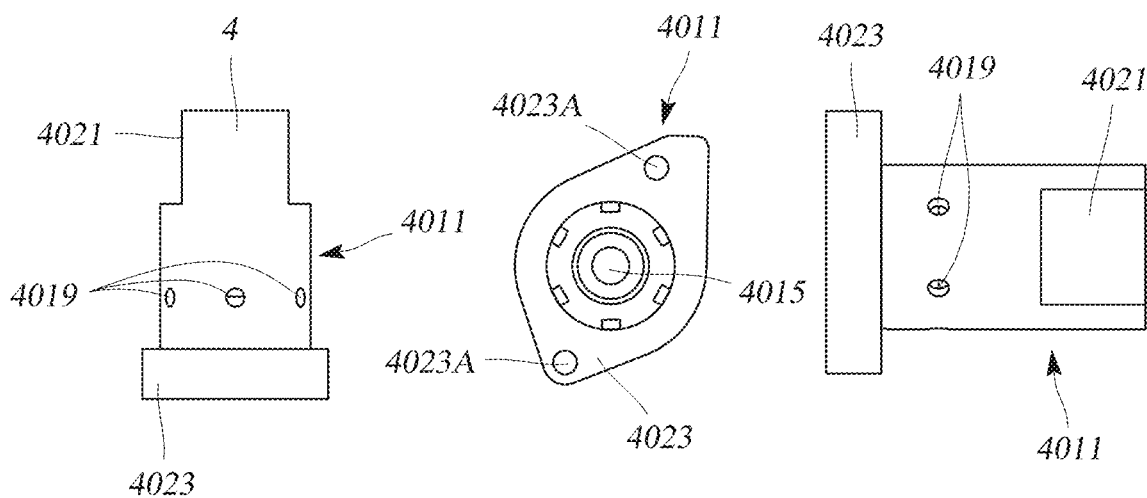
FIGURE 20B  FIGURE 20C  FIGURE 20D

VALVE MODULE AND FILTER

TECHNICAL FIELD

The present invention relates to a valve module and filter for use in an apparatus for delivering a flow of gas.

BACKGROUND ART

Breathing assistance apparatuses are used in various environments such as hospital, medical facility, residential care, or home environments to deliver a flow of gas to users or patients.

SUMMARY

The applicant has identified potential difficulties in replacing valves or servicing other components in breathing assistance apparatuses, which typically require substantial disassembly of the housing of the breathing assistance apparatus which risks compromising seals of the apparatus. That could potentially render the apparatus susceptible to liquid, gas, or solid particulate ingress. If oxygen was to ingress into the apparatus, it may be a safety risk. If liquid was to ingress into the apparatus, it could reduce dielectric strength of electronic components, such as by short-circuit or corrosion. Ingress of solid particulates could be problematic if the solid particulates enter into the gas flow path.

The applicant has also identified potential difficulties in positioning apparatuses with connected gases lines, which gases lines may prevent the apparatus from being positioned correctly and/or which may be damaged during the positioning of the apparatus.

The applicant has also identified potential issues with gas entrainment in filters that enable gases to mix in the filter and/or that enable gases to pass back through gases inlets.

The applicant has also identified pressure drops in apparatuses that utilise filters and valves, caused by flow resistance from direction changes, restrictions, convergences, divergences, filter mediums, and different frictional characteristics acting on gases passing through components caused by different material use for different components.

Accordingly, it would be desirable to provide a valve module that is readily replaceable.

Additionally or alternatively, it would be desirable to provide an apparatus with a gases inlet that can be selectively positioned to enable easy positioning of the apparatus.

Additionally or alternatively, it would be desirable to provide a filter that assists with entrainment of gas in an apparatus for delivering a flow of gas.

Additionally or alternatively, it would be desirable to provide a valve module or a filter that minimises pressure drop.

It is an object of one or more of the disclosed embodiments to provide a filter, a valve module, or an apparatus for delivering a flow of gas that goes at least some way toward achieving one or more of the above desirable outcomes, or that at least provides the public or a medical professional with a useful choice.

Thus, in accordance with certain features, aspects and advantages of at least one of the embodiments disclosed herein, a valve module for an apparatus for delivering a flow of gas is disclosed, the valve module comprising: a filter for an apparatus for delivering a flow of gas, the filter comprising: a filter body, wherein the filter body has a main compartment and a sub-compartment at least partly within the main compartment, wherein the main compartment is in fluid communication with a main compartment gases inlet and the sub-compartment is in fluid communication with a sub-compartment gases inlet; and a filter medium associated with both the main compartment and the sub-compartment, and that is arranged to filter gases in, or exiting, the main compartment and the sub-compartment.

In some configurations, the filter is a filter module that is removably and sealably engageable with a housing of an apparatus for delivering a flow of gas.

In some configurations, the filter comprising seal(s) about an external periphery of the filter to sealingly engage the filter in the housing of the apparatus.

In some configurations, the seal(s) comprise(s) O-ring(s) or integrally formed 'wiper' seal(s).

In some configurations, the main compartment is defined by at least one main compartment wall bounding a main compartment volume.

In some configurations, the sub-compartment is defined by at least one sub-compartment wall bounding a sub-compartment volume at least partly within the main compartment volume.

In some configurations, the filter comprising a second sub-compartment at least partly within the main compartment, wherein the second sub-compartment is arranged to receive gas from a second sub-compartment gases inlet.

In some configurations, the filter medium comprises substantially a same material as the filter body.

In some configurations, the filter body comprises polypropylene material or other suitable polymeric material, and wherein the filter medium comprises spun polypropylene, other suitable polymeric or synthetic material(s), and/or wool fibres.

In some configurations, the filter medium is ultrasonically welded to the at least one main compartment wall and the at least one sub-compartment wall.

In some configurations, the at least one main compartment wall and the at least one sub-compartment wall are shaped to provide a large ultrasonic weld area.

In some configurations, the main compartment is substantially rectangular in profile.

In some configurations, the filter comprises a filter top panel that is attached or attachable to the filter body.

In some configurations, the filter top panel is attachable to the filter body by way of a snap fit.

In some configurations, the filter top panel is arranged to be substantially flush with a housing of the apparatus for delivering a flow of gas, when the filter is engaged with the housing.

In some configurations, the filter top panel comprises a handling feature to aid in insertion and/or removal of the filter from a housing of the apparatus for delivering a flow of gas.

In some configurations, the filter body comprises a gas supply line connector in fluid communication with the sub-compartment.

In some configurations, gas supply line connector comprises a gas supply line retention feature at or adjacent an upper end of the gas supply line connector.

In some configurations, the filter top panel comprises an opening that exposes and protectively surrounds the gas supply line connector.

In some configurations, the filter comprises a second sub-compartment at least partly within the main compartment, wherein the second sub-compartment is arranged to receive gas from a second sub-compartment gases inlet, and wherein a duct is provided in fluid communication with the second sub-compartment.

In some configurations, the duct is integrally formed with the filter body or is separately formed from the filter body.

Additionally, in accordance with certain features, aspects and advantages of at least one of the embodiments disclosed herein, a filter for an apparatus for delivering a flow of gas is disclosed, the filter comprising: a filter body, wherein the filter body has a main compartment that is in fluid communication with a main compartment gases inlet and a main compartment gases outlet, wherein the main compartment gases outlet is substantially planar and is spanned by a filter medium, and wherein the main compartment gases inlet and main compartment gases outlet are arranged such that a gas flow direction through the inlet is offset from a gas flow direction through the outlet.

In some configurations, the gas flow direction through the main compartment gases inlet is at an angle of about 30° to about 150° relative to the gas flow direction through the main compartment gases outlet.

In some configurations, the gas flow direction through the main compartment gases inlet is at an angle of about 60° to 120° to the gas flow direction through the main compartment gases outlet.

In some configurations, the gas flow direction through the main compartment gases inlet is substantially perpendicular to the gas flow direction through the main compartment gases outlet.

In some configurations, the main compartment is substantially rectangular in profile.

In some configurations, at least a portion of the main compartment tapers inwardly such that a portion of the main compartment spaced further from the main compartment gases inlet has a smaller dimension than a portion of the main compartment adjacent the main compartment gases inlet.

In some configurations, at least a portion of the main compartment tapers outwardly such that a portion of the main compartment spaced further from the main compartment gases inlet has a larger dimension than a portion of the main compartment adjacent the main compartment gases inlet.

In some configurations, the filter body comprises a sub-compartment at least partly within the main compartment and that is in fluid communication with a sub-compartment gases inlet.

In some configurations, the sub-compartment comprises a sub-compartment gases outlet, and wherein the filter medium spans the sub-compartment gases outlet.

In some configurations, the gas flow direction through the sub-compartment gases inlet is at an angle of about 30° to 150° to the gas flow direction through the sub-compartment gases outlet.

In some configurations, the gas flow direction through the sub-compartment gases inlet is at an angle of about 60° to 120° to the gas flow direction through the sub-compartment gases outlet.

In some configurations, the gas flow direction through the sub-compartment gases inlet is substantially perpendicular to the gas flow direction through the sub-compartment gases outlet.

In some configurations, a ratio of the area of the sub-compartment gases inlet to the sub-compartment gases outlet is between about 1:5 and about 1:80, or is between about 1:1 and about 1:40, or is about 1:20.

In some configurations, at least a portion of the sub-compartment tapers inwardly.

In some configurations, the filter comprises a second sub-compartment at least partly within the main compartment, wherein the second sub-compartment is arranged to receive gas from a second sub-compartment gases inlet.

In some configurations, the second sub-compartment comprises a second sub-compartment gases outlet, and wherein the filter medium spans the second sub-compartment gases outlet.

In some configurations, the gas flow direction through the second sub-compartment gases inlet is at an angle of about 30° to 150° to the gas flow direction through the sub-compartment gases outlet.

In some configurations, the gas flow direction through the second sub-compartment gases inlet is at an angle of about 60° to 120° to the gas flow direction through the sub-compartment gases outlet.

In some configurations, the gas flow direction through the second sub-compartment gases inlet is substantially perpendicular to the gas flow direction through the second sub-compartment gases outlet.

In some configurations, a ratio of the area of the second sub-compartment gases inlet to the second sub-compartment gases outlet is between about 1:5 and about 1:80, or is between about 1:10 and about 1:40, or is between about 1:20 and about 1:25.

In some configurations, at least a portion of the second sub-compartment tapers inwardly such that a portion of the second sub-compartment spaced further from the second sub-compartment gases inlet has a smaller dimension than a portion of the main compartment adjacent the second sub-compartment gases inlet.

In some configurations, a ratio of the area of the main compartment gases inlet to the area of the main compartment gases outlet is between about 1:10 and about 1:40, or is between about 1:15 and about 1:30, or is between about 1:20 and about 1:25.

In some configurations, the filter comprises any one or more of the features described above in relation to the first described aspect.

Additionally, in accordance with certain features, aspects and advantages of at least one of the embodiments disclosed herein, an apparatus for delivering a flow of gas is disclosed, the apparatus comprising: a filter body, the filter body having a compartment, a compartment filter medium associated with the compartment that is arranged to filter gases in, or exiting, the compartment; an outlet filter medium associated with a gases outlet, to prevent, or at least substantially inhibit particulates from inadvertently entering the filter from the outlet; wherein one of the filter compartment medium and the outlet filter medium are downstream of the other of the filter compartment medium and the outlet filter medium.

In some configurations, the outlet filter medium may be or comprise a sintered metal filter. Examples of suitable sintered metals include copper, bronze, or steel.

In some configurations, the apparatus comprises an O-ring associated with the outlet filter medium to seal the outlet filter. The O-ring may be between the filter extension duct and the filter and/or manifold outlet. Other appropriate seals may be used, such as a grommet seal, or a face seal. Additionally, or alternatively, the filter extension duct could seal with the manifold through an interference fit, or a tight clearance fit.

In some configurations, the filter could be sealed to the manifold outlet by an O-ring seal, a grommet seal, a face seal, and/or any other suitable seal. Alternatively, the lower seal may not be present.

Additionally, in accordance with certain features, aspects and advantages of at least one of the embodiments disclosed herein, an apparatus for delivering a flow of gas is disclosed, the apparatus comprising: a housing with a gases outlet for delivering a flow of gas to a patient; and a first gases inlet, a second gases inlet, and an ambient air inlet.

In some configurations, the apparatus comprises a filter to filter gases that have been received from the first gases inlet, the second gases inlet, and the ambient air inlet.

In some configurations, the apparatus comprises a blower arranged to receive gases from the filter and to deliver the gases to a gases outlet.

In some configurations, the apparatus comprises a flow control valve arranged to receive gas from the first gases inlet and to deliver the gas to the filter.

In some configurations, the apparatus comprises a valve module that is removably engageable with the housing, wherein the valve module comprises the valve and a valve manifold to receive gas from the valve, wherein the valve manifold has a valve manifold gases outlet that is arranged to deliver the gas from the flow control valve to the filter.

In some configurations, the valve module comprises a valve carrier that substantially contains and supports the valve and the valve manifold.

In some configurations, the ambient air inlet is provided in the valve carrier.

In some configurations, the valve module is arranged to directly couple with the filter to provide a gas flow path from the valve module to the filter.

In some configurations, the first gases inlet is arranged to move relative to the housing.

In some configurations, the filter comprises a filter body, wherein the filter body has a main compartment, a first sub-compartment at least partly within the main compartment, and a second compartment at least partly within the main compartment, wherein the first gases inlet, the second gases inlet, and the ambient air inlet are each in fluid communication with a respective one of the main compartment, the first sub-compartment, and the second sub-compartment.

In some configurations, the filter comprises a filter medium associated with all of the main compartment, the first sub-compartment, and the second sub-compartment, wherein the filter medium is arranged to filter gases in, or exiting, the main compartment, the first sub-compartment, and the second sub-compartment.

In some configurations, the filter comprises a main compartment gases outlet, a first sub-compartment gases outlet, and a second sub-compartment gases outlet, and wherein the filter medium spans the main compartment gases outlet, the first sub-compartment gases outlet, and the second sub-compartment gases outlet.

In some configurations, the filter is removably engageable with the housing.

In some configurations, the apparatus is a nasal high flow therapy apparatus.

Additionally, in accordance with certain features, aspects and advantages of at least one of the embodiments disclosed herein, a valve module for an apparatus for delivering a flow of gas is disclosed, the valve module comprising: a flow control valve, wherein the valve is arranged to control a flow of gas, an ambient air flow path passing through the valve module.

In some configurations, the ambient air flow path has an ambient air outlet for delivering ambient air to other components of the apparatus for delivering a flow of gas.

In some configurations, the ambient air outlet is adapted to deliver ambient air to a filter module.

In some configurations, the ambient air flow path is adapted to deliver ambient air such that it flows past one or more temperature sensors of the apparatus for delivering a flow of gas.

In some configurations, the ambient air flow path passes near or adjacent to the valve.

In some configurations, the valve module comprises a valve manifold with a valve manifold gases inlet and a valve manifold gases outlet.

In some configurations, the valve is sealingly engaged with the valve manifold.

In some configurations, the valve is arranged to control a flow of gas from the valve manifold gases inlet to the valve manifold gases outlet.

In some configurations, the valve manifold has a shape that is complementary to the shape of the valve.

In some configurations, the valve manifold has a substantially cylindrical body, and wherein the valve has a substantially cylindrical body.

In some configurations, the valve manifold gases outlet is radially located on the valve manifold.

In some configurations, the valve manifold valve manifold comprises a plurality of gases outlets that are radially located about the valve manifold.

In some configurations, the valve module a valve carrier that substantially contains and supports the valve and the valve manifold.

In some configurations, the valve carrier comprises supporting structure to support the valve and valve manifold.

In some configurations, the valve carrier comprises a speaker housing and an audio speaker located in the speaker housing.

In some configurations, the valve module comprises one or more sensors on or in the valve carrier. In some configurations, one or more sensors comprises an ambient humidity sensor. In some configurations, the one or more sensors comprises an ambient pressure sensor. In some configurations, one or more sensors comprises an ambient temperature sensor.

In some configurations, the valve carrier comprises a first valve carrier part and a second valve carrier part, wherein the valve and valve manifold are secured in place at least partly between the first valve carrier part and the second valve carrier part.

In some configurations, the valve carrier comprises one or more guards.

In some configurations, the valve module comprises an electrical connector to provide an electrical connection between the valve module and one or more of the other components of the apparatus for delivering a flow of gas.

In some configurations, the electrical connector comprises a printed circuit board edge connector or wires.

In some configurations, the electrical connector comprises a flexible printed circuit board.

In some configurations, the valve carrier comprises flow guiding structure, wherein the flow guiding structure is arranged to direct gas flow from the valve manifold gases outlet(s) toward a filter when the valve module is removably engaged with the housing.

In some configurations, the valve module comprises a connector with a gases inlet, wherein the gases inlet of the connector is fluidly connectable to a gas supply line, and wherein the connector is arranged to provide a fluid connection between the gas supply line and the gases inlet of the valve manifold, and wherein the gases inlet is movable relative to the valve manifold.

In some configurations, the connector is a swivel connector, wherein the gases inlet is oriented substantially transversely relative to a longitudinal axis of the valve manifold, and wherein the gases inlet of the swivel connector is arranged to rotate about a longitudinal axis of the valve manifold.

In some configurations, the connector is a swivel connector, wherein the gases inlet is oriented substantially transversely relative to a longitudinal axis of the valve manifold, and wherein the gases inlet of the swivel connector is arranged to rotate in substantially any direction relative to the valve manifold via a ball and socket arrangement.

In some configurations, the gases inlet of the swivel connector extends in a substantially perpendicular direction relative to the longitudinal axis of the valve manifold.

In some configurations, the gases inlet of the valve manifold is axially located at or toward an end of the valve manifold.

In some configurations, the gases inlet of the swivel connector is rotatable through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

In some configurations, the valve manifold gases inlet extends substantially transversely relative to a longitudinal axis of the valve manifold, and is fluidly connectable to a gas supply Hoe, and wherein the valve and valve manifold are rotatable relative to the valve carrier about the longitudinal axis of the valve manifold.

In some configurations, the valve manifold gases inlet extends in a substantially perpendicular direction relative to the longitudinal axis of the valve manifold.

In some configurations, the valve and valve manifold are rotatable relative to the valve carrier through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

In some configurations, the valve module is arranged to directly couple with a filter module to provide a gas flow path from the valve module to the filter module.

In some configurations, the valve module is removably engageable with a housing of the apparatus for delivering a flow of gas, such that the valve module is substantially received within the housing and is accessible from an exterior of the housing.

Additionally, in accordance with certain features, aspects and advantages of at least one of the embodiments disclosed herein, an apparatus for delivering a flow of gas is disclosed, the apparatus comprising: a housing with a gases outlet for delivering a flow of gas to a patient, the housing defining a recess; and a filter module as described above engaged with the recess.

In some configurations, the apparatus further comprises a valve module as described above.

In some configurations, the valve module is directly coupled with the filter to provide a gas flow path from the valve module to the filter.

Additionally, in accordance with certain features, aspects and advantages of at least one of the embodiments disclosed herein, an apparatus for delivering a flow of gas is disclosed, the apparatus comprising: a housing defining a recess; and a valve module as described above removably received in the recess of the housing.

In some configurations, the valve module is retained in the recess of the housing by fasteners, a snap fit, a releasable snap fit, or the like.

In some configurations, the valve module is as described above, wherein the gases inlet that is fluidly connectable to the gas supply line is movable between a substantially horizontal position and a substantially vertical position, relative to the housing.

Additionally, in accordance with certain features, aspects and advantages of at least one of the embodiments disclosed herein, an apparatus for delivering a flow of gas is disclosed, the apparatus comprising: a housing with a gases outlet for delivering a flow of gas to a patient; and a connector comprising a gases inlet for receipt of a flow of gas from a gas supply line, wherein the gases inlet is fluidly connectable to a gas supply line to receive gas from the gas supply line, wherein the gases inlet of the connector is arranged to move relative to the housing.

In some configurations, the gases inlet of the connector is arranged to rotate relative to the housing.

In some configurations, the gases inlet of the connector is rotatable through up to about 190 degrees relative to the housing, or through up to about 180 degrees relative to the housing, or through up to about 160 degrees relative to the housing, or through up to about 120 degrees relative to the housing, or through up to about 90 degrees relative to the housing, through up to about 60 degrees relative to the housing, or through up to about 45 degrees relative to the housing.

In some configurations, the gases inlet extends substantially transversely relative to an axis of rotation of the gases inlet.

In some configurations, the gases inlet extends substantially perpendicularly relative to the axis of rotation of the gases inlet.

In some configurations, the gases inlet extends substantially perpendicular to a sidewall of the housing.

In some configurations, the axis of rotation is a first axis of rotation of the gases inlet of the connector, and wherein the gases inlet of the connector is additionally arranged to rotate about a second axis that is transverse to the first axis of rotation.

In some configurations, the gases inlet of the connector is arranged to rotate in substantially any direction relative to the valve manifold via a ball and socket arrangement.

In some configurations, the gases inlet of the connector is arranged to translate relative to the housing.

In some configurations, the apparatus is arranged to simultaneously receive pas from the gases inlet and ambient air.

In some configurations, the apparatus is configured such that the gas from the gases inlet and the ambient air are dynamically entrained/mixed in the apparatus prior to being delivered to the gases outlet.

In some configurations, the apparatus comprises a valve module, wherein the connector is part of the valve module.

In some configurations, the valve module is arranged to control a flow of gas from gases inlet into the apparatus.

In some configurations, the connector is arranged to receive a gas supply line via a gas supply line connection.

In some configurations, the gas supply line connection is moveable between a substantially horizontal position and a substantially vertical position, relative to the housing.

Additionally, in accordance with certain features, aspects and advantages of at least one of the embodiments disclosed herein, a combination is disclosed, the combination comprising: a valve module, wherein the valve module comprises a flow control valve, wherein the valve is arranged to control a flow of gas, and wherein the valve module is removably engageable with a housing of an apparatus for delivering a flow of gas; and a filter module, wherein the filter module is removably engageable with the housing of an apparatus for delivering a flow of gas, such that the filter module is accessible from an exterior of the housing, and wherein the filter module is arranged to receive gases from the valve module.

In some configurations, the valve module is arranged to directly couple with the filter module to provide a gas flow path from the valve module to the filter module.

In some configurations, the valve module comprises the valve and a valve manifold to receive gas from the valve, wherein the valve manifold has a valve manifold gases outlet that is arranged to deliver the gas from the flow control valve to the filter module.

In some configurations, the valve module comprises a valve carrier that substantially contains and supports the valve and the valve manifold.

In some configurations, the valve carrier comprises an ambient air inlet.

In some configurations, the valve module comprise a connector with a gases inlet for delivering gases to the valve.

In some configurations, the filter module comprises a filter body, wherein the filter body has a main compartment and at least one sub-compartment at least partly within the main compartment, wherein the main compartment and the at least one sub-compartment are arranged to receive gases from respective gases inlets, and are arranged to deliver gases through respective gases outlets.

In some configurations, the filter module comprises a filter medium associated with the main compartment and the sub-compartment(s), wherein the filter medium is arranged to filter gases in, or exiting, the main compartment and the sub-compartment(s).

In some configurations, the filter medium spans the main compartment gases outlet and the first sub-compartment gases outlet(s).

In some configurations, the valve module is substantially received within the housing and is accessible from an exterior of the housing.

Additionally, in accordance with certain features, aspects and advantages of at least one of the embodiments disclosed herein, an apparatus for delivering a flow of gas is disclosed, the apparatus comprising: a housing with a gases outlet for delivering a flow of gas to a patient, a gases inlet, and a sealed gases path between the gases inlet and the gases outlet, the sealed gases path comprising a filter to filter gases that have been received from the first gases inlet, the filter comprising a filter body, a gases inlet, a gases outlet, and a filter medium that is arranged to filter gases in, or exiting, the filter body.

In some configurations, the filter is a filter module that is removably and sealably engageable with the housing.

In some configurations, the filter module is removable from the housing such that the sealed path is unsealed when the filter module is removed.

Additionally, in accordance with certain features, aspects and advantages of at least one of the embodiments disclosed herein, an apparatus for delivering a flow of gas is disclosed, the apparatus comprising:

a valve module, wherein the valve module comprises a flow control valve, wherein the valve is arranged to control a flow of gas; and a filter module arranged to receive gases from the valve module.

In some configurations, the valve module is arranged to directly couple with the filter module to provide a gas flow path from the valve module to the filter module.

In some configurations, the valve module comprises the valve and a valve manifold to receive gas from the valve, wherein the valve manifold has a valve manifold gases outlet that is arranged to deliver the gas from the flow control valve to the filter module.

In some configurations, the valve module comprises a valve carrier that substantially contains and supports the valve and the valve manifold.

In some configurations, the valve carrier comprises an ambient air inlet.

In some configurations, the valve module comprise a connector with a gases inlet for delivering gases to the valve.

In some configurations, the filter module comprises a filter body, wherein the filter body has a main compartment and at least one sub-compartment at least partly within the main compartment, wherein the main compartment and the at least one sub-compartment are arranged to receive gases from respective gases inlets, and are arranged to deliver gases through respective gases outlets.

In some configurations, the filter module comprises a filter medium associated with the main compartment and the sub-compartments), wherein the filter medium is arranged to filter gases in, or exiting, the main compartment and the sub-compartment(s).

In some configurations, the filter medium spans the main compartment gases outlet and the first sub-compartment gases outlet(s).

Additionally, in accordance with certain features, aspects and advantages of at least one of the embodiments disclosed herein, a valve module for an apparatus for delivering a flow of gas is disclosed, the valve module comprising: a flow control valve, wherein the valve is arranged to control a flow of gas; wherein the valve module is removably engageable with a housing of the apparatus for delivering a flow of gas, such that the valve module is substantially received within the housing and is accessible from an exterior of the housing.

In some configurations, the valve is arranged to control a flow of gas into part of the apparatus. For example, the valve may be arranged to control a flow of gas to a filter. Alternatively, the valve may be arranged to control a flow of gas to another part of the apparatus. The valve and filter may be positioned upstream of a blower of the apparatus. The valve and filter may be positioned downstream of a blower of the apparatus.

In some configurations, part of the valve module is arranged to be substantially flush with an external wall of the housing when the valve module is removably engaged with the housing.

In some configurations, the valve module comprises a valve manifold with a valve manifold gases inlet and a valve manifold gases outlet. In some configurations, the valve manifold has a plurality of valve manifold gases outlets.

In some configurations, the valve is sealingly engaged with the valve manifold.

In some configurations, the valve is arranged to control a flow of gas from the valve manifold gases inlet to the valve manifold gases outlet.

In some configurations, the valve is a solenoid valve, a motor-driven valve, or a piezo-operated valve.

In some configurations, the valve is a proportional solenoid valve. In some configurations, an extent of gas flow through the valve (i.e., the valve opening) is relative to an amount of electrical current supplied to the valve. In some configurations, the valve may be a different type of electrically-actuated valve, such as an electrically actuated solenoid valve.

In some configurations, the valve manifold has a shape that is complementary to the shape of the valve. In some configurations, the valve manifold has a substantially cylindrical body, and the valve has a substantially cylindrical body. Alternatively, the valve manifold and valve may have different shapes.

In some configurations, the valve manifold gases outlet is radially located on the valve manifold. In some configurations, the valve manifold comprises a plurality of valve manifold gases outlets that are radially located about the valve manifold.

In some configurations, the valve manifold gases outlet(s) is/are aeroacoustically shaped to reduce noise. The valve manifold gases outlet(s) may be one, or a combination of, through-holes, frustoconical, or flared in shape.

In some configurations, the valve module comprises a valve carrier that substantially contains and supports the valve and the valve manifold. In some configurations, the valve carrier is removably engageable with the housing of the apparatus.

In some configurations, the valve carrier comprises supporting structure to support the valve and valve manifold. In some configurations, the supporting structure comprises one, two, or more supports to support the valve and valve manifold.

In some configurations, the valve carrier comprises a speaker housing and an audio speaker located in the speaker housing.

In some configurations, a temperature sensor is provided on or in the valve carrier. In some configurations, the temperature sensor comprises a thermistor, a digital temperature sensor, or any other suitable type of temperature sensor. In some configurations, the temperature sensor is configured to provide ambient temperature feedback to a controller of the apparatus.

In some configurations, the valve carrier comprises a first valve carrier part and a second valve carrier part, wherein the valve and valve manifold are secured in place at least partly between the first valve carrier part and the second valve carrier part. In some configurations, the first valve carrier part comprises a lower valve carrier part, and the second valve carrier part comprises an upper valve carrier part. Alternatively, the first valve carrier part may comprise a first side part and the second valve carrier part may comprise a second side part. In some configurations the valve carrier comprises one or more guards.

In some configurations, the valve module comprises an electrical connector to provide an electrical connection between the valve module and the apparatus for delivering a flow of gas. In some configurations, the electrical connector is in electric/electronic communication with the valve, wherein the electrical connector is arranged or adapted to engage with a complementary connector in the apparatus for delivering a flow of gas; for example by plugging into the complementary connector. In some configurations the electrical connector comprises wires to provide the electrical/electronic communication between the valve and the electrical connector. In some configurations the electrical connector comprises a flexible printed circuit board. In some configurations, the electrical connector may additionally comprise grommets. In some alternative configurations, a printed circuit board (PCB) is positioned in a housing of the apparatus for delivering a flow of gas, and the electrical connector in the valve module comprises an edge connector to engage with the printed circuit board. In some configurations, the PCB is in electric/electronic communication with the temperature sensor and speaker if provided.

In some configurations, the electrical connector projects from or is positioned in a top, side, or base of the valve carrier. In some configurations, the complementary connector is provided in a valve module receiving cavity of the apparatus for delivering a flow of gas.

In some configurations, the valve carrier comprises flow guiding structure, wherein the flow guiding structure is arranged to direct gas flow from the valve manifold gases outlet(s) toward a filter when the valve module is removably engaged with the housing. In some configurations, the flow guiding structure comprises an annular housing that surrounds a plurality of valve manifold gases outlets, wherein the flow guiding structure comprises a gases outlet that is in fluid communication with a gases inlet of the filter.

In some configurations, the valve module comprises a connector with a gases inlet, wherein the gases inlet of the connector is fluidly connectable to a gas supply line, and wherein the connector is arranged to provide a fluid connection between the gas supply line and the gases inlet of the valve manifold, wherein the gases inlet of the connector is movable relative to the valve manifold. In some configurations, the connector is a swivel connector, the gases inlet is oriented substantially transversely relative to a longitudinal axis of the valve manifold, and the gases inlet of the swivel connector is arranged to rotate about a longitudinal axis of the valve manifold. In some configurations, the gases inlet of the swivel connector is additionally arranged to rotate about a second axis that is transverse to the longitudinal axis of the valve manifold. In some configurations, the swivel connector is arranged to provide both swivelling and translational movement, so that the gases inlet of the swivel connector may both swivel about one or more axes and may also travel linearly for example. In some configurations, the swivel connector may comprise a ball and socket arrangement or similar, to enable the gases inlet of the swivel connector to rotate in substantially any direction relative to the valve manifold.

In some configurations, the gases inlet of the swivel connector is oriented substantially perpendicularly relative to the longitudinal axis of the valve manifold. In some configurations, the gases inlet could be oriented at a different substantially transverse angle relative to the longitudinal axis of the valve manifold.

In some configurations, the gases inlet of the valve manifold is axially located at or toward an end of the valve manifold.

In some configurations, the gases inlet of the swivel connector is rotatable through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

In some configurations, the valve manifold gases inlet extends substantially transversely relative to a longitudinal axis of the valve manifold, and is fluidly connectable to a gas supply line, and the valve and valve manifold are rotatable relative to the valve carrier about the longitudinal axis of the valve manifold.

In some configurations, the valve manifold gases inlet extends in a substantially perpendicular direction relative to the longitudinal axis of the valve manifold. In some configurations, the valve manifold gases inlet could be oriented at a different substantially transverse angle relative to the longitudinal axis of the valve manifold.

In some configurations, the valve and valve manifold are rotatable relative to the valve carrier through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

In some configurations, the gases inlet of the connector is arranged to translate relative to the valve manifold.

In some configurations, the valve module is arranged to directly couple with a filter to provide a gas flow path from the valve module to the filter.

Additionally, in accordance with certain features, aspects and advantages of at least one of the embodiments disclosed herein, an apparatus for delivering a flow of gas is disclosed, the apparatus comprising: a housing defining a recess; and a valve module as outlined above removably received in the recess of the housing.

In some configurations, the valve module is retained in the recess of the housing by fasteners, a snap fit, or the like.

In some configurations, the gases inlet that is fluidly connectable to the gas supply line is movable between a substantially horizontal position and a substantially vertical position, relative to the housing. In some configurations, the substantially horizontal position is a side, forward, or rearward position. In some configurations, the substantially vertical position is an upward or downward position. In some configurations, the substantially horizontal position is a side position and the substantially vertical position is a downward position.

Additionally, in accordance with certain features, aspects and advantages of at least one of the embodiments disclosed herein, an apparatus for delivering a flow of gas is disclosed, the apparatus comprising: a housing with a gases outlet for delivering a flow of gas to a patient; and a connector comprising a gases inlet for receipt of a flow of gas from a gas supply line, wherein the gases inlet is fluidly connectable to a gas supply line to receive gas from the gas supply line, wherein the gases inlet of the connector is arranged to move relative to the housing.

In some configurations, the gases inlet of the connector is arranged to rotate relative to the housing. In some configurations, the gases inlet of the connector is rotatable through up to about 190 degrees relative to the housing, or through up to about 180 degrees relative to the housing, or through up to about 160 degrees relative to the housing, or through up to about 120 degrees relative to the housing, or through up to about 90 degrees relative to the housing, or through up to about 60 degrees relative to the housing, or through up to about 45 degrees relative to the housing.

In some configurations, the gases inlet extends substantially transversely relative to an axis of rotation of the gases inlet relative to the housing. Therefore, when a gas supply line is fluidly connected to the gases inlet, the gas supply line can extend substantially transversely relative to the axis of rotation.

In some configurations, the gases inlet extends substantially perpendicularly relative to the axis of rotation of the gases inlet. In some configurations, the gases inlet could be oriented at a different substantially transverse angle relative to the axis of rotation of the gases inlet.

In some configurations, the axis of rotation is a first axis of rotation of the gases inlet of the connector, and the gases inlet of the connector is additionally arranged to rotate about a second axis that is transverse to the first axis of rotation.

In some configurations, the gases inlet of the connector is arranged to rotate in substantially any direction relative to the valve manifold via a ball and socket arrangement.

In some configurations, the gases inlet of the connector is additionally or alternatively arranged to translate relative to the housing.

In some configurations, the apparatus is arranged to simultaneously receive gas from the gases inlet and ambient air. In some configurations, the apparatus is configured such that the gas from the gases inlet and the ambient air are dynamically entrained/mixed in the apparatus prior to being delivered to the gases outlet. In some configurations, the apparatus comprises a blower to transfer the gas from the gases inlet and the ambient air, via a gas flow path, to the gases outlet.

In some configurations, the apparatus is arranged to draw in ambient air via suction provided by the blower. In some configurations, the apparatus is arranged to simultaneously draw in gas from the gases inlet. In some alternative configurations, the apparatus is arranged to simultaneously receive pressurised gas from the gases inlet. In some configurations the pressurised gas is received from a pressurised wall supply, gas tank, or other source.

In some configurations, the apparatus comprises a valve module, wherein the connector is part of the valve module. In some configurations, the valve module is arranged to control a flow of gas from gases inlet into the apparatus.

In some configurations, the connector is arranged to receive a gas supply line via a gas supply line connection. In some configurations, the gas supply line connection is moveable between a substantially horizontal position and a substantially vertical position, relative to the housing. In some configurations, the substantially horizontal position is a side, forward, or rearward position. In some configurations, the substantially vertical position is an upward or downward position. In some configurations, the substantially horizontal position is a side position and the substantially vertical position is a downward position.

Additionally, in accordance with certain features, aspects and advantages of at least one of the embodiments disclosed herein, a filter for an apparatus for delivering a flow of gas is disclosed, the filter comprising:

a filter body, wherein the filter body has a main compartment and a sub-compartment at least partly within the main compartment, wherein the main compartment is in fluid communication with a main compartment gases inlet and the sub-compartment is in fluid communication with a sub-compartment gases inlet; and a filter medium associated with both the main compartment and the sub-compartment, and that is arranged to filter gases in, or exiting, the main compartment and the sub-compartment.

In some configurations, the filter body comprises a plurality of sub-compartments located at least partly within the main compartment. In some configurations, the filter body comprises one sub-compartment, two sub-compartments, or three or more sub-compartments.

In some configurations, the sub-compartment(s) are located entirely within the main compartment. Alternatively, in some configurations, the sub-compartment(s) are located partly externally of the main compartment. In some configurations, at least one sub-compartment is located entirely within the main compartment and at least one sub-compartment is located partly externally of the main compartment.

In some configurations, the filter medium covers or spans the main compartment and the sub-compartment(s).

In some configurations, the filter medium is located on an external face of the filter body to filter gases exiting the main compartment and the sub-compartment. Alternatively, in some configurations the filter medium may be positioned at least partly within the main compartment and the sub-compartment to filter gases in the main compartment and the sub-compartment.

In some configurations, the filter is a filter module that is removably and sealably engageable with a housing of an apparatus for delivering a flow of gas. In some configurations, the filter comprises seal(s) about an external periphery of the filter to sealingly engage the filter in the housing of the apparatus. In some configurations, the filter and seal(s) are arranged such that gases entering the apparatus are forced to pass through the filter before entering the gas flow path of the apparatus. In some configurations, the seal(s) comprise(s) O-ring(s) or integrally formed 'wiper' seal(s). The integrally formed wiper seal(s) provide(s) ease of manufacture.

In some configurations, the main compartment is defined by at least one main compartment wall bounding a main compartment volume. In some configurations, the sub-compartment is defined by at least one sub-compartment wall bounding a sub-compartment volume at least partly within the main compartment volume.

In some configurations, the main compartment is arranged to receive oxygen (or other gases) from a valve manifold. In some alternative configurations, the main compartment is arranged to receive ambient air.

In some configurations, the sub-compartment may be arranged to receive oxygen (or other gases) from a top, alternative supply. In some configurations, the sub-compartment may be arranged to receive oxygen (or other gases) from a side or rear alternative supply.

In some configurations, the filter comprises a second sub-compartment at least partly within the main compartment, wherein the second sub-compartment is arranged to receive gas from a second sub-compartment gases inlet.

In some configurations, the second sub-compartment may receive ambient air. In some alternative configurations, the second sub-compartment may receive oxygen (or other gases) from a valve manifold.

In some configurations, the filter medium comprises substantially a same material as the filter body. In some configurations, the filter body comprises polypropylene material or other suitable polymeric material, and the filter medium comprises spun polypropylene or other suitable polymeric or synthetic material(s).

In some configurations, the filter medium is ultrasonically welded to the at least one main compartment wall and the at least one sub-compartment wall. In some configurations, the at least one main compartment wall and the at least one sub-compartment wall are shaped to provide a large ultrasonic weld area. In some configurations, the main compartment wall and the at least one sub-compartment wall comprise one or more of a flange and/or a substantially flattened 'n'-shaped wall formation.

In some alternative configurations, the filter medium may be overmoulded to the at least one main compartment wall and the at least one sub-compartment wall. In some alternative configurations, the filter medium may be adhered to the at least one main compartment wall and the at least one sub-compartment wall, with glue or resin adhesive.

In some configurations, the main compartment is substantially rectangular in profile. In alternative configurations, the main compartment has a different shape in profile, such as round, elliptical, square, or any other suitable shape.

In some configurations, the filter has a filter top panel that is attached or attachable to the filter body. In some configurations, the filter top panel is attachable to the filter body by way of a snap fit, clips, fasteners, or other suitable attachments.

In some configurations, the filter top panel is arranged to be substantially flush with a housing of the apparatus for delivering a flow of gas, when the filter is engaged with the housing.

In some configurations, the filter top panel is made from a same material as an adjacent portion of the housing of the apparatus. In some configurations, the filter top panel is polycarbonate or another suitable polymeric material.

In some configurations, the filter top panel comprises a handling feature to aid in insertion and/or removal of the filter from a housing of the apparatus for delivering a flow of gas.

In some configurations, the filter handling feature comprises a ridge, groove, or grip. In some configurations, the filter handling feature is provided at a periphery of the filter top panel. In some configurations, the filter handling feature is provided elsewhere on the filter top panel. In some configurations, the filter top panel comprises a plurality of filter handling features.

In some configurations, the filter body comprises a gas supply line connector in fluid communication with the sub-compartment. In some configurations, the gas supply line connector comprises a gas supply line retention feature such as a barb at or adjacent an upper end of the gas supply line connector.

In some configurations, the gas supply line connector may be connectable to an oxygen line to receive oxygen from an alternative supply. In some configurations, the filter top panel comprises an opening that exposes and protectively surrounds the gas supply line connector.

In some configurations, the filter comprises a second sub-compartment at least partly within the main compartment, wherein the second sub-compartment is arranged to receive gas from a second sub-compartment gases inlet, and wherein a duct is provided in fluid communication with the second sub-compartment. The duct may be arranged to receive gases from the valve manifold gases outlets, for example via a flow guiding structure on the valve manifold.

In some configurations, the duct is integrally formed with the filter body or is separately formed from the filter body.

Additionally, in accordance with certain features, aspects and advantages of at least one of the embodiments disclosed herein, a filter for an apparatus for delivering a flow of gas is disclosed, the filter comprising:

a filter body, wherein the filter body has a main compartment that is in fluid communication with a main compartment gases inlet and a main compartment gases outlet, wherein the main compartment gases outlet is substantially planar and is spanned by a filter medium, and wherein the main compartment gases inlet and main compartment gases outlet are arranged such that a gas flow direction through the inlet is offset from a gas flow direction through the outlet.

In some configurations, the gas flow direction through the main compartment gases inlet is substantially perpendicular to the gas flow direction through the main compartment gases outlet.

In some configurations, the main compartment is substantially rectangular in profile. In alternative configurations, the main compartment has a different shape in profile, such as round, elliptical, square, or any other suitable shape.

In some configurations, at least a portion of the main compartment tapers inwardly such that a portion of the main compartment spaced further from the main compartment gases inlet has a smaller dimension than a portion of the main compartment adjacent the main compartment gases inlet. Incoming gases may thereby be deflected substantially transversely toward/through the filter medium.

In some configurations, substantially the entire main compartment tapers inwardly. In some configurations, the filter body comprises an angled wall that at least partly defines the main compartment and provides the tapering of the main compartment. The angled wall may be positioned on an opposite face of the main compartment to the filter medium.

In some configurations, only a small part of the main compartment tapers inwardly.

In some configurations, the filter body comprises a sub-compartment at least partly within the main compartment and that is in fluid communication with a sub-compartment gases inlet. In some configurations, the sub-compartment comprises a sub-compartment gases outlet, and the filter medium spans the sub-compartment gases outlet.

In some configurations, the filter body comprises two, three, or more sub-compartments. Each of the sub-compartments may be arranged to deliver a secondary or alternative gas to the apparatus for delivering a flow of gas. For example, one of the sub-compartments may be used to deliver oxygen, and one of the sub-compartments may be used to deliver heliox.

In some configurations, a ratio of the area of the sub-compartment gases inlet to the sub-compartment gases outlet is between about 1:5 and about 1:80, or is between about 1:10 and about 1:40, or is about 1:20.

In some configurations, the filter body comprises a second sub-compartment at least partly within the main compartment, wherein the second sub-compartment is arranged to receive gas from a second sub-compartment gases inlet. In some configurations, the second sub-compartment comprises a second sub-compartment gases outlet, and the filter medium spans the second sub-compartment gases outlet. In some configurations, a ratio of the area of the second sub-compartment gases inlet to the second sub-compartment gases outlet is between about 1:5 and about 1:80, or is between about 1:10 and about 1:40, or is between about 1:20 and about 1:25.

In some configurations, a ratio of the area of the main compartment gases inlet to the area of the main compartment gases outlet is between about 1:10 and about 1:40, or is between about 1:15 and about 1:30, or is between about 1:20 and about 1:25.

In some configurations, the filter comprises any one or more of the features outlined in relation to the other configurations described herein.

In some configurations, filter medium(s) may be provided on two opposing faces of the filter to form two main compartment gases outlets and, depending on the number of sub-compartments, one, two, or more sub-compartment gases outlets. In some configurations, a ratio of the area of the main compartment gases inlet to the total area of the main compartment gases outlets is between about 1:20 and about 1:80, or is between about 1:30 and about 1:60, or is between about 1:40 and about 1:50. In some configurations having a first sub-compartment with two sub-compartment gases outlets, a ratio of the area of the first sub-compartment gases inlet to the total area of the sub-compartment gases outlets is between about 1:10 and about 1:160, or is between about 1:20 and about 1:80, or is about 1:40. In some configurations having a second sub-compartment with two second sub-compartment gases outlets, a ratio of the area of the second sub-compartment gases inlet to the total area of the second sub-compartment gases outlets is between about 1:10 and about 1:160, or is between about 1:20 and about 1:80, or is between about 1:40 and about 1:50.

Additionally, in accordance with certain features, aspects and advantages of at least one of the embodiments disclosed herein, an apparatus for delivering a flow of gas is disclosed, the apparatus comprising:

a housing with a gases outlet for delivering a flow of gas to a patient, the housing defining a recess; and a filter as outlined above engaged with the recess.

In some configurations, the apparatus comprises a valve module as outlined above.

Additionally, in accordance with certain features, aspects and advantages of at least one of the embodiments disclosed herein, an apparatus for delivering a flow of gas is disclosed, the apparatus comprising:

a housing with a gases outlet for delivering a flow of gas to a patient; and a first gases inlet, a second gases inlet, and an ambient air inlet.

In some configurations, the apparatus comprises a filter to filter gases that have been received from the first gases inlet, the second gases inlet, and the ambient air inlet.

In some configurations, the apparatus comprises a how control valve arranged to receive gas from the first gases inlet and to deliver the gas to the filter.

In some configurations, the apparatus comprises a blower arranged to receive gases from the filter and to deliver the gases to the gases outlet.

In some configurations, the apparatus comprises a valve module that is removably engageable with the housing, wherein the valve module comprises the valve and a valve manifold to receive gas from the valve, wherein the valve manifold has a valve manifold gases outlet that is arranged to deliver the gas from the flow control valve to the filter. In some configurations, the valve module comprises a valve carrier that substantially contains and supports the valve and the valve manifold. In some configurations, the ambient air inlet is provided in the valve carrier.

In some configurations, the valve module is arranged to directly couple with the filter to provide a gas flow path from the valve module to the filter.

In some configurations, the first gases inlet is arranged to move relative to the housing.

In some configurations, the filter comprises a filter body, wherein the filter body has a main compartment, a first sub-compartment at least partly within the main compartment, and a second compartment at least partly within the main compartment, wherein the first gases inlet, the second gases inlet, and the ambient air inlet are each in fluid communication with a respective one of the main compartment, the first sub-compartment, and the second sub-compartment. In some configurations, the filter comprises a filter medium associated with all of the main compartment, the first sub-compartment, and the second sub-compartment, wherein the filter medium is arranged to filter gases in, or exiting, the main compartment, the first sub-compartment, and the second sub-compartment. In some configurations, the filter comprises a main compartment gases outlet, a first sub-compartment gases outlet, and a second sub-compartment gases outlet, and the filter medium spans the main compartment gases outlet, the first sub-compartment gases outlet, and the second sub-compartment gases outlet.

In some configurations, the filter is removably engageable with the housing.

In some configurations, the apparatus is a nasal high flow therapy apparatus.

Additionally, in accordance with certain features, aspects and advantages of at least one of the embodiments disclosed herein, there is disclosed the combination of:

a valve module, wherein the valve module comprises a flow control valve, wherein the valve is arranged to control a flow of gas, and wherein the valve module is removably engageable with a housing of an apparatus for delivering a flow of gas, such that the valve module is substantially received within and is accessible from an exterior of the housing; and a filter module, wherein the filter module is removably engageable with the housing of an apparatus for delivering a flow of gas, such that the filter module is accessible from an exterior of the housing, and wherein the filter module is arranged to receive gases from the valve module.

In some configurations, the valve module is arranged to directly couple with the filter module to provide a gas flow path from the valve module to the filter module.

In some configurations, the valve module comprises the valve and a valve manifold to receive gas from the valve, wherein the valve manifold has a valve manifold gases outlet that is arranged to deliver the gas from the flow control valve to the filter. In some configurations, the valve module comprises a valve carrier that substantially contains and supports the valve and the valve manifold. In some configurations, the valve carrier comprises an ambient air inlet.

In some configurations, the valve module comprise a connector with a gases inlet for delivering gases to the valve, wherein the gases inlet is movable.

In some configurations, the filter comprises a filter body, wherein the filter body has a main compartment and at least one sub-compartment at least partly within the main compartment, wherein the main compartment and the at least one sub-compartment are arranged to receive gases from respective gases inlets, and a arranged to deliver gases through respective gases outlets.

In some configurations, the filter comprises a filter medium associated with the main compartment and the sub-compartment(s), wherein the filter medium is arranged to filter gases in, or exiting, the main compartment and the sub-compartment(s). In some configurations, the filter medium spans the main compartment gases outlet and the first sub-compartment gases outlet(s).

It will be appreciated that the filter and the valve module described herein may be used separately in apparatuses for delivering a flow of gas. Alternatively, the filter and the valve module may be used together for improved functionality. The filter and the valve module may be provided together to provide a filter and valve assembly.

Features from one or more embodiments or configurations may be combined with features of one or more other embodiments or configurations. Additionally, more than one embodiment may be used together during a process of respiratory support of a patient.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. This invention may also be said broadly to consist in the parts, elements and features referred to or indicated in the specification of the application, individually or collectively, and any or all combinations of any two or more said parts, elements or features.

BRIEF DESCRIPTION OF THE DRAWINGS

Specific embodiments and modifications thereof will become apparent to those skilled in the art from the detailed description herein having reference to the figures that follow, of which:

FIGS. 20A, 20B, 20C, and 20D are perspective, top, end, and side views respectively of a valve manifold of the first configuration valve module.

DETAILED DESCRIPTION OF SPECIFIC EMBODIMENTS

1. Introduction

Figure 1:
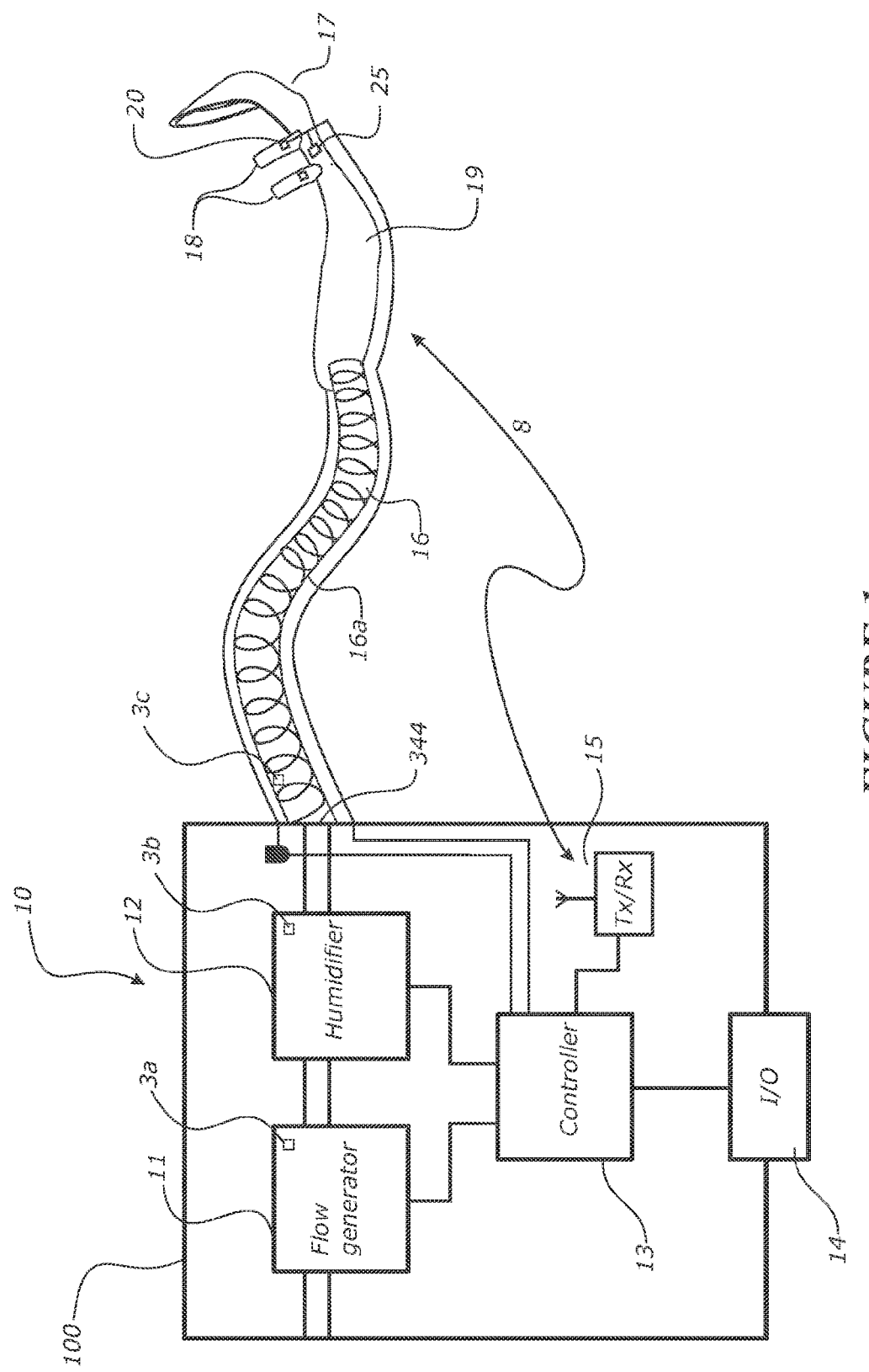
FIG. 1 shows in diagrammatic form a breathing assistance apparatus in the form of a flow therapy apparatus.

A flow therapy apparatus 10 for delivering a flow of gas to a patient is shown in FIG. 1. In general terms, the apparatus 10 comprises a main housing 100, a flow generator 11 in the form of a motor/impeller arrangement, an optional humidifier 12, a controller 13, a user I/O interface 14 (comprising, for example, a display and input device(s) such as button(s), a touch screen, or the like), a filter module 1001, 2001 (FIGS. 15 and 16), 3001 (FIGS. 38 to 40), 11001 (FIG. 46) and a valve module 4001, 5001, 6001, 7001, 8001, 9001 (FIGS. 17 to 37). The controller 13 is configured or programmed to control the components of the apparatus, including: operating the flow generator 11 to create a flow of gas (gas flow) for delivery to a patient, operating the humidifier 12 (if present) to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gas flow output 344 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gas flow, which may be humidified, that is generated by the flow therapy apparatus 10 is delivered to the patient via the patient breathing conduit 16 through the cannula 17. The patient breathing conduit 16 can have a heater wire 16a to heat gas flow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and controls the humidifier 12 if present to humidify the gas flow and/or heat the gas flow to an appropriate level. The gas flow is directed out through the patient breathing conduit 16 and cannula 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with, or can determine, a suitable target temperature of the gas flow.

Operation sensors 3a, 3b, 3c, 20, and 25, such as flow, temperature, humidity, and/or pressure sensors, can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. 'High flow therapy' as used in this disclosure may refer to delivery of gases to an adult patient at a flow rate of greater than or equal to about 10 liters per minute (10 LPM), or to a neonatal, infant, or child patient at a flow rate of greater than or equal to about 1 liters per minute (1 LPM) or 2 liters per minute (2 LPM). In some configurations, for an adult patient 'high flow therapy' may refer to the delivery of gases to a patient at a flow rate of between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. Therefore, a high flow therapy apparatus for us with either an adult patient or a neonatal, infant, or child patient, may deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available for each and every breath, while minimising re-breathing of carbon dioxide, nitrogen, etc.

High flow therapy may be administered to the nares of a user and/or orally, or via a tracheostomy interface. High flow therapy may deliver gases to a user at a flow rate at or exceeding the intended user's peak inspiratory flow requirements. The high flow therapy may generate a flushing effect in the nasopharynx such that the anatomical dead space of the upper airways is flushed by the high incoming gases flow. This can create a reservoir of fresh gas available for each and every breath, while minimizing re-breathing of nitrogen and carbon dioxide.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As shown in FIGS. 2A to 42 and described below, the flow therapy apparatus 10 has various features to assist with the functioning, use, and/or configuration of the apparatus 10.

2. Overview Including Main Housing Description

As shown in FIGS. 2A to 6, the flow therapy apparatus 10 comprises a main housing 100. The main housing 100 has a main housing upper chassis 102 and a main housing lower chassis 202.

The main housing has a peripheral wall arrangement. The peripheral wall arrangement defines a humidifier or liquid chamber bay 108 for receipt of a removable liquid chamber 300. The removable liquid chamber 300 contains a suitable liquid such as water for humidifying gases that will be delivered to a patient.

In the form shown, the main housing lower chassis 202 peripheral wall arrangement comprises a substantially vertical left side outer wall 210 that is oriented in a front-to-rear direction of the main housing 100, a substantially vertical right side outer wall 216, and a substantially vertical rear outer wall 222 that extends between and connects the walls 210, 216. A bottom wall 230 extends between and connects the lower ends of walls 210, 216, 222, and forms a substantially horizontal floor portion 136 of the liquid chamber bay.

In the form shown, the main housing upper chassis 102 peripheral wall arrangement comprises a left side upper wall 114 that extends in front-to-rear direction of the main housing, a right side upper wall 120 that extends in a front-to-rear direction of the main housing, and a rear laterally extending wall 128 that extends between and connects the walls 114, 120.

The floor portion 136 of the liquid chamber bay 108 has a recess to receive a heater arrangement such as a heater plate or other suitable heating element(s) for heating liquid in the liquid chamber 300 for use during a humidification process.

The liquid chamber bay 108 further comprises opposed guide features in the form of left side and right side horizontally extending guide rails 144, 146 which extend toward a centre of the bay 108 from the respective left and right side inner walls 112, 118 to assist with guiding the liquid chamber 300 into position in the bay 108.

The main housing lower chassis 202 is attachable to the upper chassis 102, either by suitable fasteners or integrated attachment features such as clips for example. When the main housing lower chassis 202 is attached to the main housing upper chassis 102, lower edges of the left side upper wall 114, right side upper wall 120, and rear laterally extending wall 128 of the upper chassis engage with the upper edges of the left side outer wall 210, right side outer wall 216, and rear outer wall 222 respectively of the main housing lower chassis.

The apparatus has tongue and groove arrangements between components of the apparatus to reduce water and oxygen ingress into the unit. The apparatus advantageously has tongue and groove arrangements between the upper edges of the lower chassis walls and the lower edges of the upper chassis walls. The tongue and groove arrangements provide a substantially continuous liquid/gas flow-resistant coupling around the periphery of the upper and lower chassis parts 102, 202. For example, the lower chassis walls may be provided with grooves and the upper chassis walls may be provided with complementary tongues that are configured to be at least partly received in the respective grooves when the upper and lower chassis parts are assembled together. The continuous coupling advantageously extends along the front, sides, and at least most of the rear of the chassis parts, as shown, including around any corners between those surfaces.

The described configurations and orientations are examples only, and any suitable combination of the tongue and groove arrangements and/or orientations of the tongue and groove arrangements may be used in the apparatus.

Figure 6:
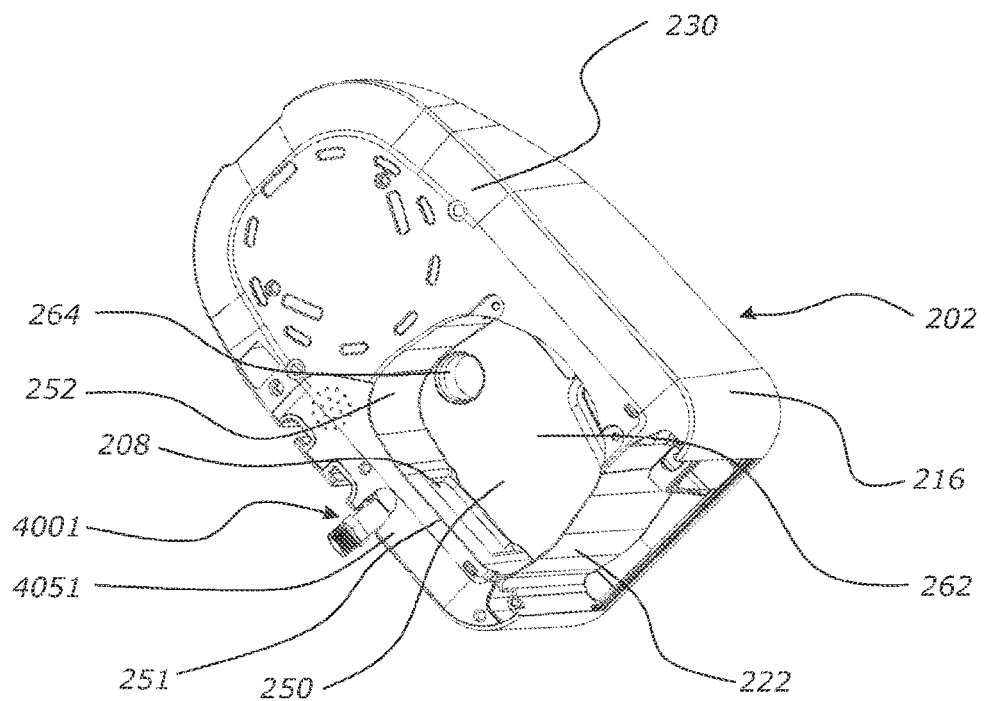
FIG. 6 is an underside perspective view of the lower chassis of the flow therapy apparatus with the valve module and the filter module in place.
Figure 7:
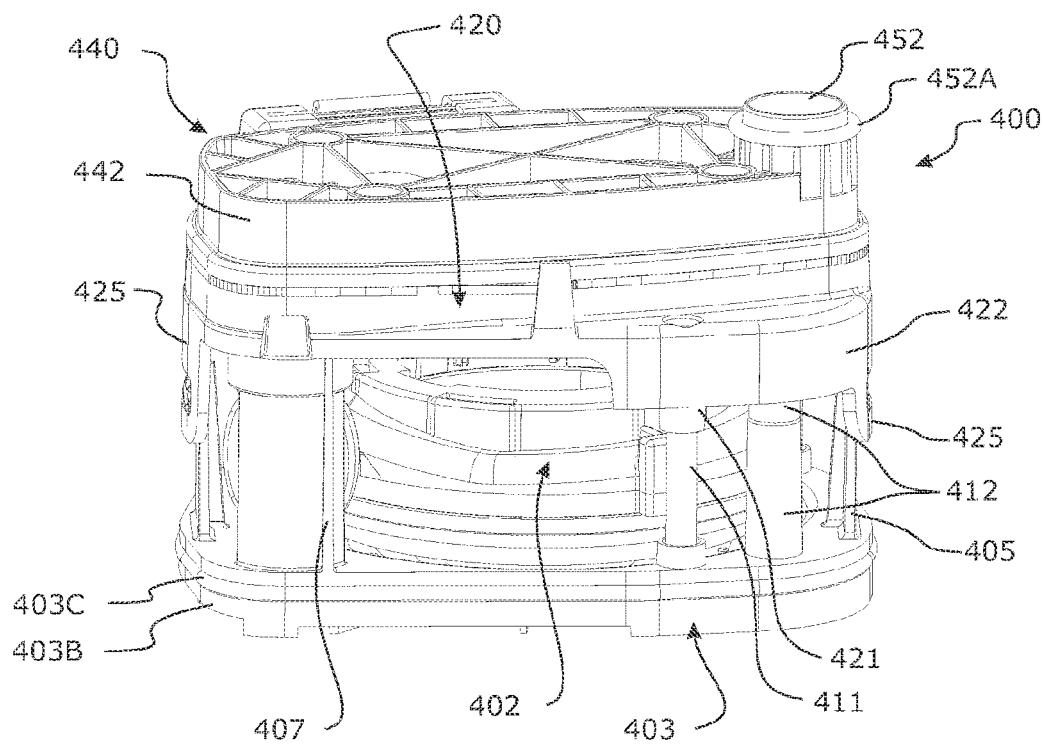
FIG. 7 shows a motor and/or sensor module for use in the apparatus for delivering a flow of gas.
Figure 8:
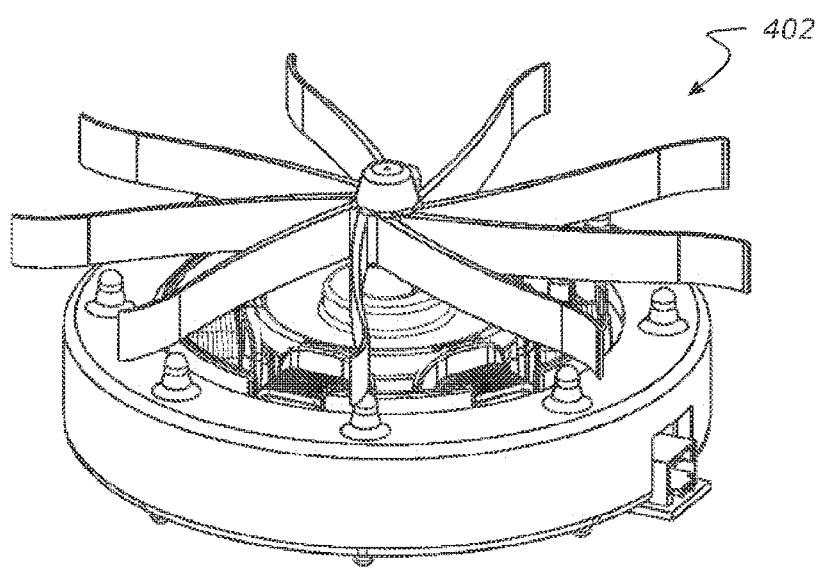
FIG. 8 shows a blower unit for the motor and/or sensor module.
Figure 9:
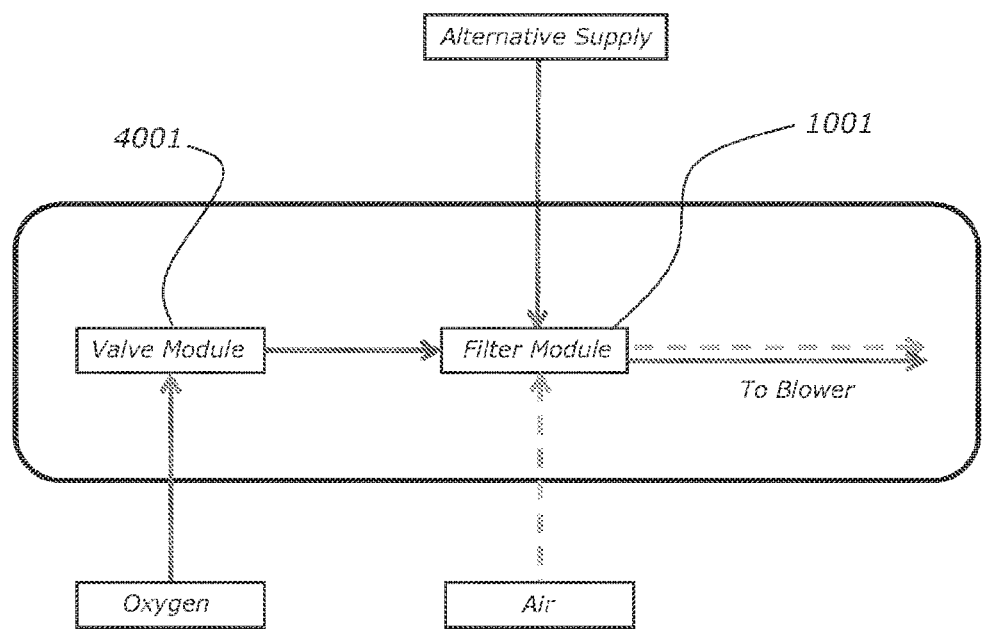
FIG. 9 is a schematic gas flow path diagram for the filter module and the valve module, with the solid line arrows representing the flow of oxygen (or another gas), and the dashed line arrows representing the flow of ambient air.

As shown in FIG. 6, the lower chassis 202 has a motor recess 250 for receipt of a motor and/or sensor module 400 of the apparatus 10, which is shown in FIGS. 7 and 8 and will be described in further detail below. The motor and/or sensor module may be removable or non-removable. A recess opening 251 is provided in the bottom wall 230 adjacent a rear edge thereof, for receipt of the motor/sensor module 400. A continuous, gas impermeable, unbroken peripheral wall 252 or walls is/are integrally formed with the bottom wall 230 of the lower chassis 202 and extend(s) upwardly from the periphery of the opening 251. The upper edge of the peripheral wall 252 terminates at a ceiling 262. All of the walls and the ceiling 262 are continuous, gas impermeable, and unbroken, other than a tube 264 in the ceiling 262 that forms the gas flow passage for gas to exit the motor and/or sensor module 400, and an aperture 208 in the wall 252 for receipt of the gases outlet of a gases filter module 1001, 2001, 3001, 11001. The tube 264 forming the gas flow passage is integrally formed with the ceiling 262, with the ceiling surrounding and extending outwardly from the tube 264. Therefore, the entire motor recess 250 is gas impermeable and unbroken, other than the gas flow passage and the entrance for the filter module gases outlet.

The tube 264 forming the gas flow passage will extend upwardly through a downward outer extension tube or conduit that is integrally formed with a ledge 132 (FIG. 4) of the upper housing chassis 102. The tube 264 extends at least as far as the ledge 132, and may extend to a point where it is vertically higher than the ledge 132. A soft seal such as an O-ring seal (not shown) is located between the exterior of the gas flow passage tube 264 and the interior of the downward outer extension tube, to provide a seal between the components when assembled. In other configurations, the gas flow passage tube 264 and the downward extension tube could be configured to be fitted together via an interference or press fit arrangement while still providing for a seal between the components when assembled. Still other configurations including but not limited to latch/catch-style fittings and bayonet-style fittings between the gas flow passage tube 264 and the downward extension tube are contemplated.

The configuration is such that if there is any leaking of gas from the motor or gas flow path following the motor via any seals, the gas will vent to atmosphere rather than ingressing into the interior of the main housing that contains the control boards and other electrical components. The electrical components and electronics boards in the housing are pneumatically isolated from the gas flow path. The only way for gas to leak into the portion of the main housing 100 that contains the electronics boards and other electrical components will be if there is a physical crack in the housing 100 or another physical component. The pressure in the motor of the motor and/or sensor module 400 upstream of the impeller may be lower than the pressure in the portion of the main housing 100 that contains the electrical/electronic components, which also assists with any gas leaks venting to atmosphere.

There will be a pressure drop in the gas flow as it moves through the system due to the formation of gas turbulence and due to friction (e.g. as gas passes along walls defining the gas passages).

In the motor and/or sensor module 400, the pressure is lower before/upstream of the motor impeller, and the pressure is higher after/downstream of the motor impeller. An electrical connection will be provided for the motor upstream of the motor impeller, in the lower pressure region. If there is a failure in the housing in the portion near the electrical connection, air will be sucked into the low pressure side.

In an alternative configuration, the motor recess 250 may be separately formed from the lower chassis 202. The motor assembly including the recess may be insertable into the recess opening 251 and attachable to the lower chassis 202. Upon insertion of the motor assembly and recess into the lower chassis 202, the gas flow passage tube 264 will extend through the downward extension tube 133 and be sealed by the soft seal.

In the form shown, the recess 250 comprises a recess opening in a bottom wall of the housing. Alternatively, the recess opening could be in a different part of the housing, such as a side, front, or top of the housing.

The described configuration provides a chamber shaped to receive and contain a motor and/or sensor module 400 of the apparatus 10 as described below with reference to FIGS. 7 and 8. The interior wall of the recess 250 (including but not limited to portions of the peripheral wall 252) may be provided with guides and/or mounting features to assist with locating and/or attaching the module 400 in the recess 250. The motor and/or sensor module 400 is a flow generator and comprises a motor 402 with an impeller that operates as a blower to deliver gases to the patient interface 17 via the liquid chamber 300. It will be appreciated that the shape of the chamber can vary depending on the shape of the motor/sensor module 400. However, the chamber will be provided with continuous, gas impermeable, and unbroken walls and a ceiling to isolate the gas flow from electrical and electronic components in the main housing 100.

Figure 3A:
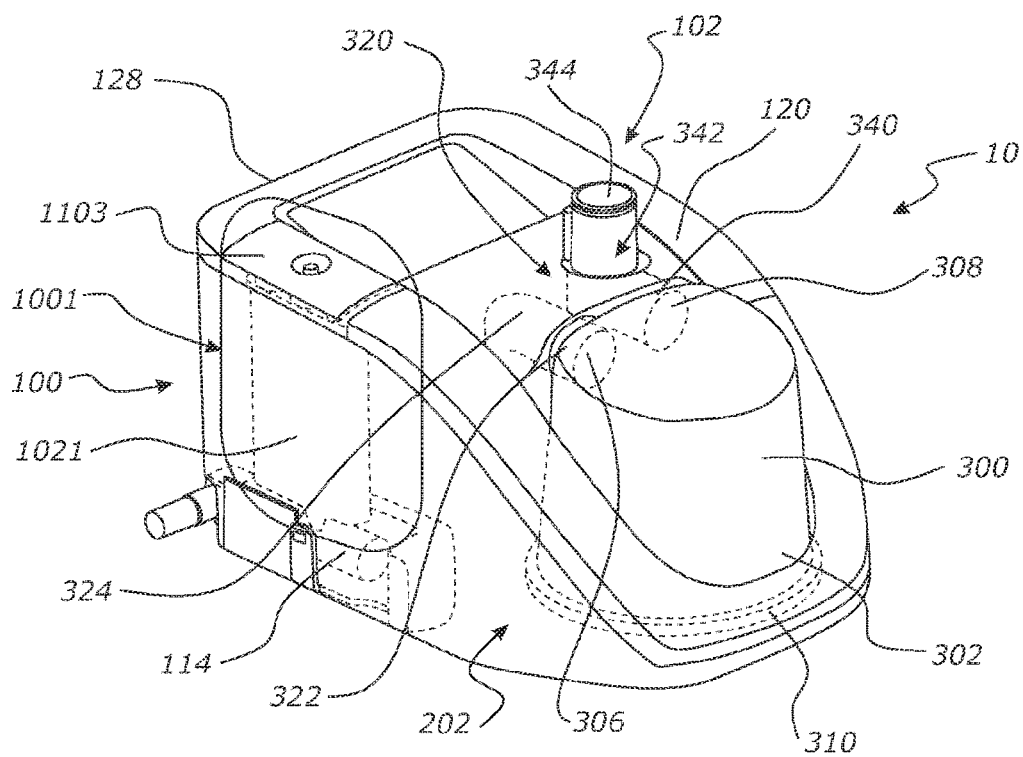
FIG. 3A is a left front perspective view of the flow therapy apparatus with the filter module highlighted.
Figure 3B:
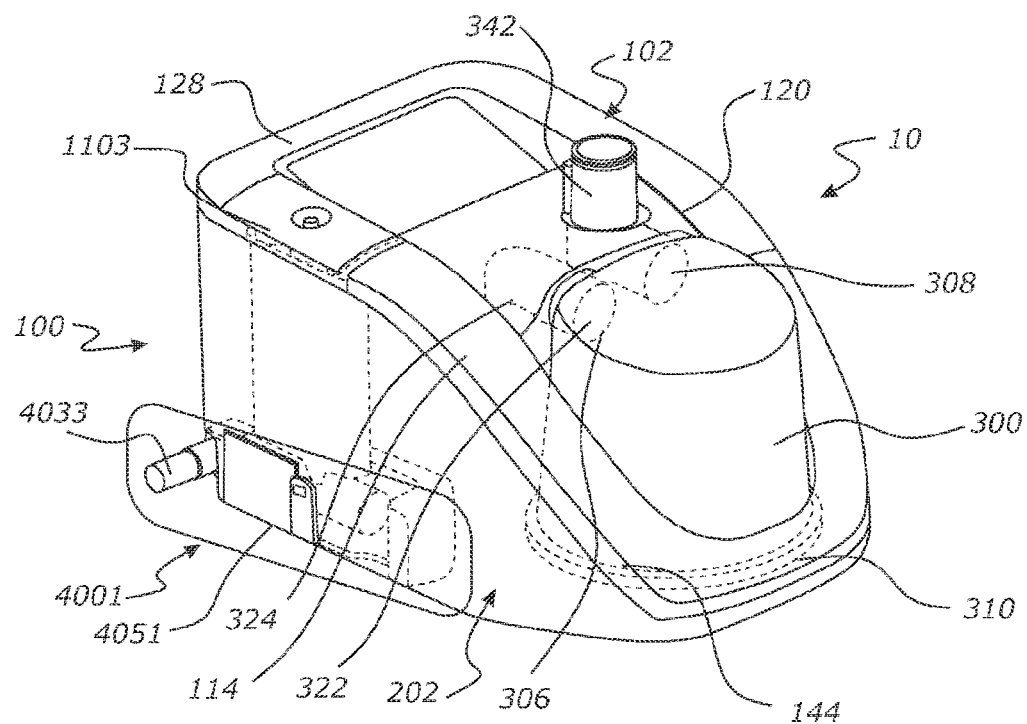
FIG. 3B is a left front perspective view of the flow therapy apparatus with the valve module highlighted.

With reference to FIGS. 3A and 3B, the removable liquid chamber 300 comprises an outer housing 302 defining a liquid reservoir, a liquid chamber gases inlet port 306 in fluid communication with the liquid reservoir, and a liquid chamber gases outlet port 308 in fluid communication with the liquid reservoir. A baffle may be provided internally in the liquid reservoir to define a flow path of gases through the liquid chamber 300. A lower edge of the liquid chamber 300 comprises an outwardly directed annular flange 310 which interacts with opposed guide rails 144 in the chamber bay 108 for locating and retaining the liquid chamber 300 in the chamber bay 108. The flange 310 extends outwardly from the base of a peripheral wall of the liquid chamber 300. A bottom wall of the liquid chamber 300 is heat conducting and is adapted for resting on a heater plate for heating liquid in the liquid chamber 300.

The apparatus 10 comprises a connection manifold arrangement 320 for fluid coupling of the liquid chamber 300 to the apparatus 10. The liquid chamber 300 can be fluidly coupled to the apparatus 10 in a linear slide-on motion in a rearward direction of the liquid chamber 300 into the chamber bay 108, from a position at the front of the housing 100 in a direction toward the rear of the housing 100. The connection manifold arrangement 320 comprises a manifold gases outlet port 322 that is in fluid communication, via a fixed L shaped elbow 324, with the gas flow passage from the motor/impeller unit 402 (FIG. 8). A lower portion of the elbow 324 that forms a gas flow inlet port of the elbow extends downwardly into the interior of the gas flow passage tube 264, preferably to a position below the lower end of the gas flow passage tube 264. A soft seal such as an O-ring seal is provided between the exterior of the lower portion of the elbow and the interior of the gas flow passage tube 264 to seal between those components.

The connection manifold arrangement 320 further comprises a manifold gases inlet port 340 (humidified gases return) that is embodied in a removable elbow 342. The removable elbow 342 is L-shaped, and further comprises a patient outlet port 344 for coupling to the patient breathing conduit 16 to deliver gases to the patient interface 17. The manifold gases outlet port 322, manifold gases inlet port 340, and patient outlet port 344 each comprise soft seals such as O-ring seals, T-seals, or the like to provide a sealed gases passageway between the apparatus 10, the liquid chamber 300, and the patient breathing conduit 16.

The liquid chamber gases inlet port 306 is complementary with the connection manifold gases outlet port 322, and the liquid chamber gases outlet port 308 is complementary with the connection manifold gases inlet port 340. The axes of those ports are preferably parallel to enable the liquid chamber 300 to be inserted into the chamber bay 108 in a linear movement.

Motor and/or Sensor Module

FIGS. 7 and 8 show a motor and/or sensor module or sub-assembly 400 that can be used as a flow generator in the flow therapy apparatus.

The motor and/or sensor module or sub-assembly 400 of the apparatus has been designed as an individual and sealed component. Any seals that are breached will cause gases such as oxygen to leak to the atmosphere rather than into the electronics of the apparatus. The module 400 may be replaceable, so if a sensor fails the entire module can be replaced. The module may only contain electronics relevant to sensing.

The motor and/or sensor module 400 comprises a stacked arrangement of three main components; a base 403 of the sub-assembly 400 (on which is positioned the motor 402 with an impeller that forms a blower), an outlet gas flow path and sensing layer 420 positioned above the base 403, and a cover layer 440. The cover layer 440 and outlet gas flow path and sensing layer 420 will typically be assembled together in use to form the sensing layer. The gases move through the module 400 from a gases inlet, through the blower 402, through the gas flow path and sensing layer 420, and through gases outlet port 452 to be delivered via the fixed elbow 324 to the liquid chamber 300*a* and then via the removable elbow 342 through the patient gases outlet port 344 of the apparatus. An opening formed between the blower 402 and the outlet gas flow path and sensing layer 420 provides a gases inlet into the module and enables the temperature of incoming gases to be measured.

The base 403 comprises a region for receipt of the gas blower motor 402. The region may be concave. The diameter of the concave region is selected to correspond with the shape of the underside of the body of the motor 402. The region guides gas flow to the blower. In an alternative configuration, the region may be a different shape, for example a non-concave shape.

The base 403 comprises a plurality of flexible mounts 411. The flexible mounts act as vibration isolating structures. Engagement plates are retained by the upper casing of the motor/blower 402 body, and provide a slot into which the mounts can slide. Upper ends of the mounts are received in complementary receiving portions such as cups in a body 422 of the outlet gas flow path and sensing layer 420.

The base 403 and the body 422 of the outlet gas flow path and sensing layer 420 are provided with complementary securing features 405, 425 to secure the body 422 to the base 403. Alternatively, a different securing method could be used. The base 403 comprises a plurality of vertically extending members such as posts 407. Body 422 may comprise complementary members to engage with the members 407, to prevent rocking of the body 422 relative to the base 403. The base 403 and/or body 422 also comprise(s) a plurality of locating pins 412 to guide the base and body together during coupling.

A periphery 403B of the base 403 is provided with a recess that receives a soft seal such as an O-ring seal 403C. The seal 403C seals the module 400 against the housing of the apparatus and prevents ambient air entrainment which would bypass the filter. In particular, the seal 403C seals between the base 403 and the peripheral wall of the recess 250 of the apparatus housing. The seal 403C also provides a frictional force between the module 400 and the housing of the apparatus that must be overcome to remove the module 400 from the housing, if the module 400 is removable.

Once gases enter the module 400 via the inlet region, they move to the blower inlet, which is located underneath the blower 402 in, or above, the concave portion of the base 403. Gases entering the module may act to cool the motor. Gases then move through the blower 402 and exit via a blower gases outlet port. Gases exiting the blower gases outlet port enter a coupling tube or cuff (not shown) which couples the blower gases outlet port to a gases inlet port of the outlet gas flow path and sensing layer 420. The cuff directs the gases through an angular change of about 90 degrees from the blower outlet port to the gases inlet port, but over a short horizontal distance, while minimising pressure drop.

It will be appreciated that the cuff can be configured to direct gases through different angles depending on the required configuration. Inlet and outlet ports of the cuff will be sealed to the blower outlet port and gases inlet port using a suitable sealing arrangement; for example, soft seals such as O-ring seals.

The cuff is configured to minimise the pressure drop of the gases passing though the cuff and to isolate blower vibration from the case of the unit in tight space constraints. The cuff is made from a soft flexible material and has localised region(s) that act as a diaphragm and serve as vibration isolators. Some regions of the cuff may be thinned out to provide isolation to prevent or minimise any vibration from being transmitted to structural parts. This could be achieved by moulding thinner section(s) into the cuff. Additionally, or alternatively, a concertina may be provided in the cuff to assist with isolating vibrations from the case of the unit while allowing more movement of the module 400 in the housing.

The gas flow path and sensing layer 420 comprises a gas flow path with one or more sensors, and the gas flow path is arranged to deliver gas to the outlet port of the housing.

A body 422 of the gas flow path and sensing layer 420 defines a lower portion of a sensing and gas flow path. The cover layer 440 has a body 442 that defines an upper portion of the sensing and gas flow path, with the shape of the upper and lower portions of the sensing and gas flow path corresponding substantially to each other.

A sensing printed circuit board (PCB) may be provided in the gas flow path and sensing layer 420. At least part of the PCB overlaps with the gas flow path through the gas flow path and sensing layer 420. The PCB is sandwiched between the gas flow path and sensing layer 420 and cover layer 440. Temperature sensors will be positioned on the portion of the PCB that is within/overlaps with the gas flow path.

Soft seals such as O-ring seals, may be provided to seal between the upper side of the body 422 and the underside of the PCB, and to seal between the lower side of the body 442 and the upper side of the PCB. The soft seals seal the high pressure region of the module, as gases passing through the gas flow path have been pressurised by the blower. The seals prevent gases from escaping and moving towards the electronics of the apparatus. The soft seals could alternatively be co-moulded to the bodies, with a soft layer co-moulded onto the more rigid bodies.

The cover layer 440 may be coupled to the gas flow path and sensing layer 420 using fasteners such as screws. The fasteners sandwich the two sections together, providing a compressive force to seal the soft seals against the PCB board.

Referring to FIGS. 7, 3A, and 3B, once gases have passed through the gas flow path and sensing layer 420, they exit the module 400 via the gas flow outlet port 452 which couples with the gas flow inlet elbow 324. A soft seal such as an O-ring seal 452A may be provided to seal the gas flow outlet port 452 of the module 400. The soft seal 452A seals against an inner wall of a downward outer extension tube or conduit of the upper chassis, or another part of the housing. A soft seal such as an O-ring seal may be provided to seal between the elbow 324 and the inner wall of the downward extension tube of the upper chassis, or another part of the housing. The soft seals function to keep the module 400 sealed and reduce the likelihood of the pressurised gases flowing into the housing of the apparatus. The soft seals may be provided in annular grooves in the gas flow outlet port 452 and the gas flow inlet elbow 324. Alternatively, one of both of those components may be provided with outwardly directed shoulders to provide a resting surface for the soft-seals.

In another configuration, a different type of seal may be provided to seal between the gas flow outlet port 452, the gas flow inlet elbow 324, and/or the outer extension tube. For example, rather than using O-rings, face seal(s), foam, or a bellows seal may be used, which will allow for some relative movement of the components in a direction that is lateral to a gas flow direction through the components without breaking the seal. A seal that enables that movement will not over-constrain the module 400 when it is in place in the lower chassis, but will enable sealing between the upper surface of the gas flow outlet port 452 and the bottom surface of the inlet elbow 324, while enabling some lateral movement between the gas flow outlet port 452 of the module 400 and the inlet elbow 324. If a bellows seal is used to seal between the gas flow outlet port 452 and the inlet elbow 324, that will enable both some lateral and some axial movement between the gas flow outlet port 452 of the module 400 and the inlet elbow 324.

The connection between the gas flow outlet port 452 and gas flow inlet elbow 324 is formed outside the motor and/or sensor module 400 such that any leakage that occurs from this connection will be directed outside the housing of the apparatus. The lower chassis extends up around the outside of the inlet elbow 324, and is formed as a single integral part including the wall(s) and ceiling that define the recess 250 and gas flow tube 264. Therefore, in the case of a leak the gas will follow the path of least resistance, which is to gather outside the leak region and exit to atmosphere via the outside of the inlet elbow 324. It is very unlikely that gases will flow into the housing and via a tortuous path to the electronics of the apparatus.

The apparatus 10 has air and oxygen (or alternative auxiliary gas) inlets in fluid communication with the motor 402 to enable the motor 402 to deliver air, oxygen, or a suitable mixture thereof to the liquid chamber 300 and thereby to the patient. In some configurations, the gas comprises a blend of oxygen and ambient air. The air and oxygen (or other alternative auxiliary gas) may be delivered to the motor and/or sensor module 400 via the filter module and/or valve module configurations described below.

3. Filter Module

Figure 4:
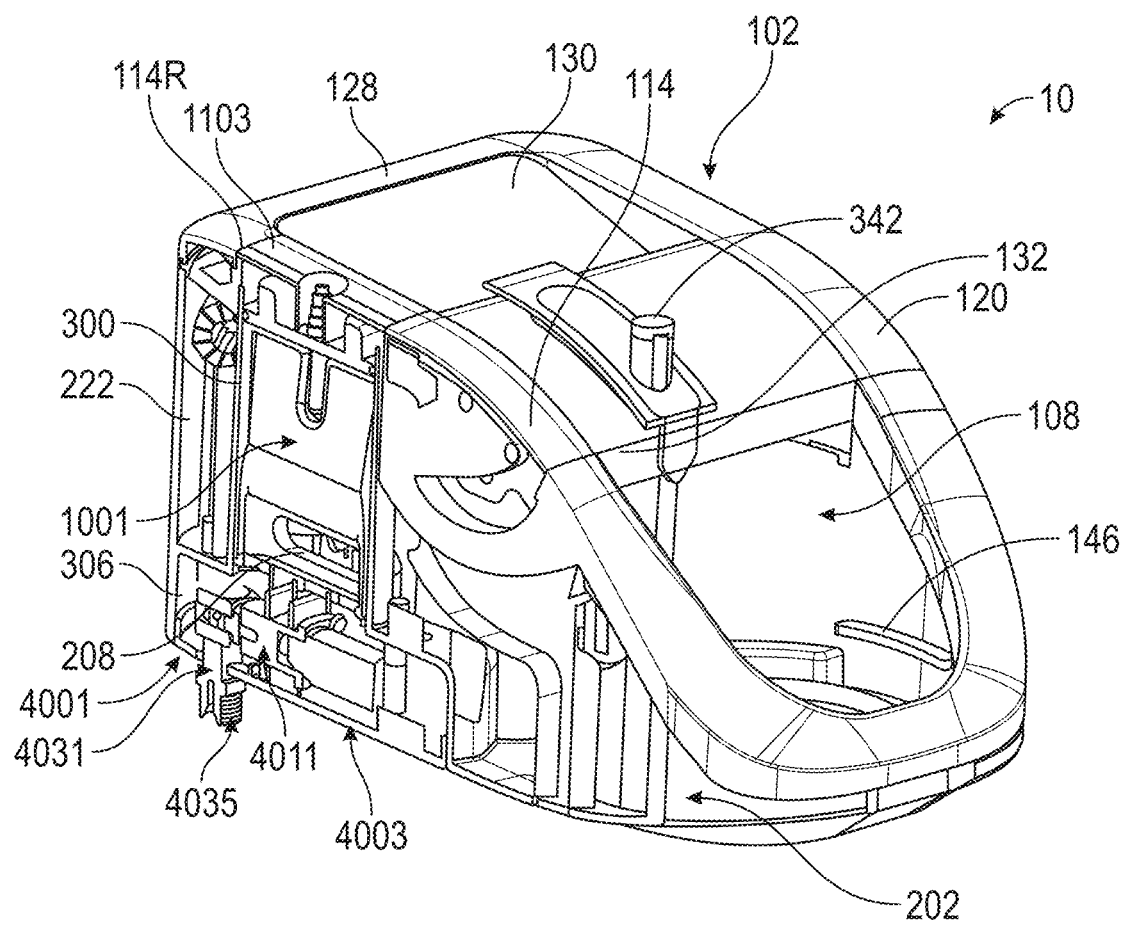
FIG. 4 is a left front perspective partial cutaway view showing the valve module and the filter module.
Figure 5:
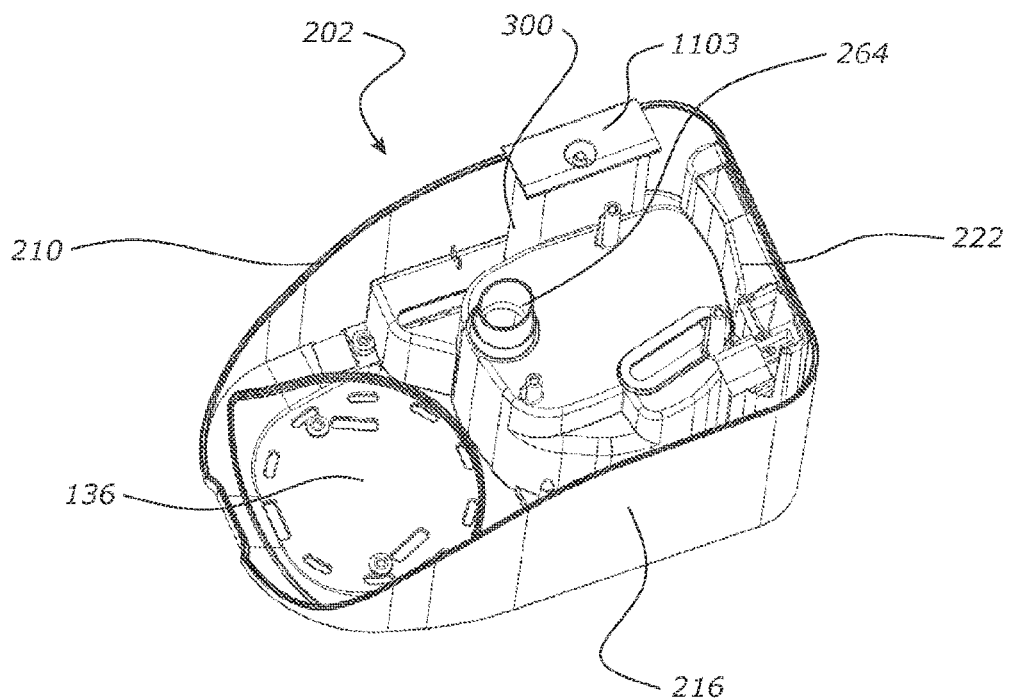
FIG. 5 is a right front overhead perspective view of the lower chassis of the flow therapy apparatus with the valve module and the filter module in place.
Figure 46:
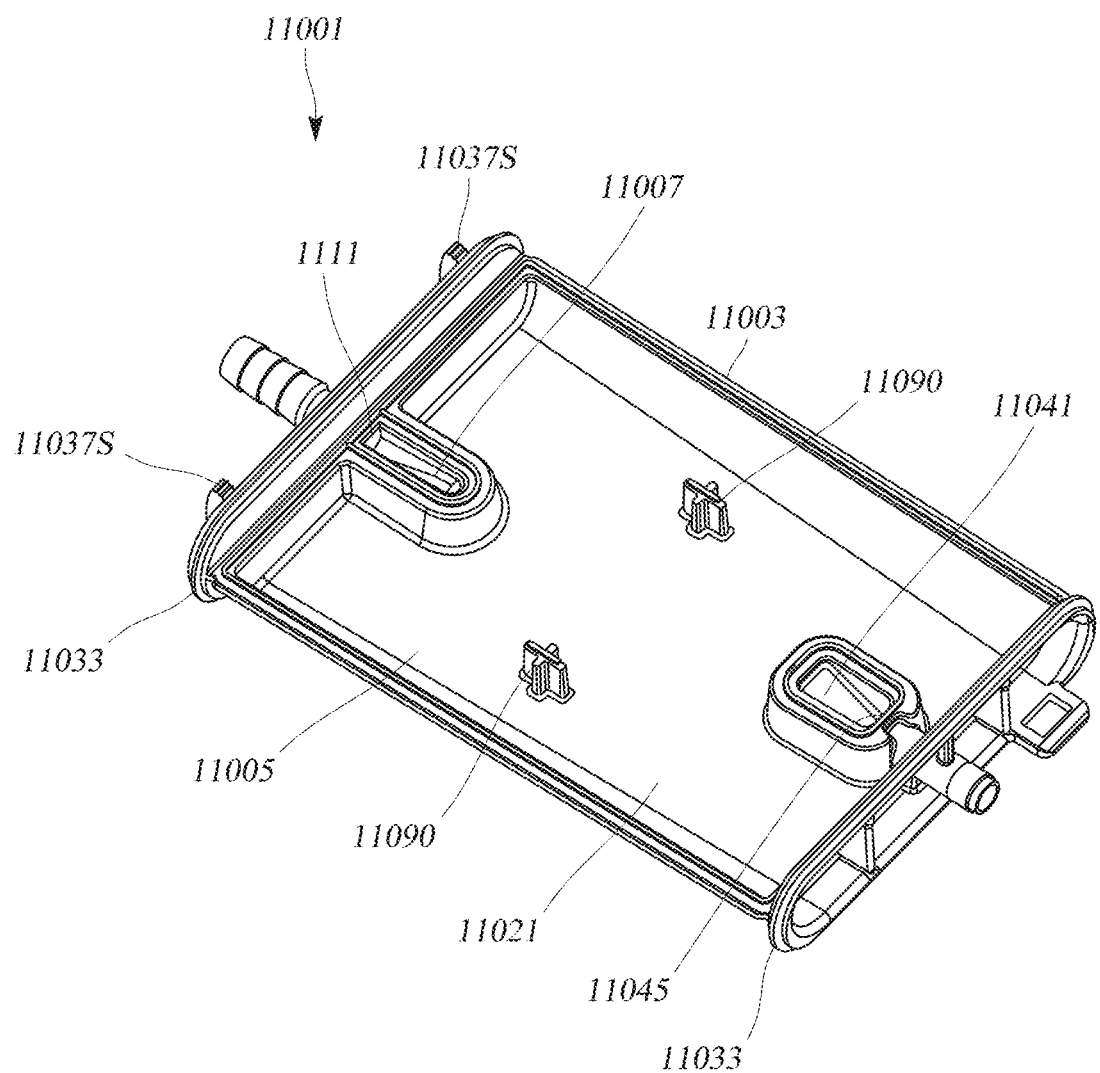
FIG. 46 is a perspective view showing a filter of a fourth configuration filter module.

As shown in FIGS. 4 and 5, the lower chassis 202 has a filter receptacle 300 which defines a cavity for receipt of the filter module 1001, 2001 (FIGS. 15 and 16), 3001 (FIGS. 38 to 40), 11001 (FIG. 46). The filter module is removably and sealably engageable with the main housing of an apparatus, by engaging with the filter receptacle of the housing. The filter module is accessible from an exterior of the main housing. An upper end 302 of the filter receptacle 300 defines an annular groove 304 for receipt of a soft seal 304 such as an O-ring seal or the like. The soft seal 304 is arranged to engage with, and provide a seal against, a surface of the upper chassis 102 of the main housing when the upper chassis and lower chassis are assembled. The lower part of the filter receptacle 300 opens into a valve module housing 306 that forms a recess for receipt of the valve module 4001, 5001, 6001, 7001, 8001, 9001 (FIGS. 17 to 37).

An inner wall of the filter receptacle 300 defines an aperture 208 that is in fluid communication with a gases outlet of the filter module 1001 (FIGS. 10 to 14), 2001, 3001. The aperture 208 directs gases to, or toward, the motor and/or sensor module 400. In one configuration, the aperture 208 directs gases into the motor recess 250, and the gases are received by the motor/impeller 402 from the motor recess. In an alternative configuration, the aperture 208 may be fluidly connected to a gases inlet of the motor and/or sensor module 400 by a fluid coupling such as a conduit or the like.

The filter receptacle 300 may be integrally formed with the lower chassis 202 such as by injection moulding or the like. Alternatively, the filter receptacle may be separately formed and attached to the lower chassis 202.

A first configuration filter module 1001 is shown in FIGS. 10 to 14. In use, the filter module is positioned substantially within the casing of the main housing and is modular for ease of manufacture, servicing, and replacement, and may be sold as a consumable part for repeat sale. The filter module may be configured to be modularly replaceable by a user on an approximately three monthly basis, or any other appropriate time period depending on factors such as the hours per day of operation of the apparatus and the environmental conditions. By replacing only the filter, cost benefits are provided. The filter module 1001 filters all incoming gases including oxygen and ambient air to prevent or minimise bacteria, dust, and particulates from entering the motor and/or sensor module 400.

The filter modules described herein are designed and configured to minimise pressure drop across the filter. At least one way in which this is achieved is by having a large surface area for the gas to pass through; i.e. a gases outlet port.

The filter module comprises a filter body 1003 that is arranged to be received in the filter receptacle 300 by inserting the filter body 1003 vertically downwardly into the receptacle from the exterior of the main housing of the apparatus. The filter module is located in the gas flow path between the valve module (described below) and the motor and/or sensor module 400. The filter body 1003 has a shape that is complementary to the shape of the filter receptacle 300. While those components are shown as substantially rectangular with arcuate ends in plan view, they could alternatively be any other suitable shape such as square or oblong for example. The filter module advantageously has a narrow transverse width so that only a narrow filter receptacle is needed in the apparatus main housing. Therefore, the filter module occupies minimal space while maintaining a large surface area for gas to pass through.

The filter body 1003 has a relatively large main compartment 1005. The main compartment is defined by at least one main compartment wall bounding a main compartment volume. In the form shown, the main compartment 1005 is defined by two substantially vertical main compartment side walls 1013, 1015, a lower wall 1017, and upper wall 1019, and a rear wall 1021 of the filter body 1003. The main compartment is shown as being substantially rectangular in profile shape. However, any suitable shape could be provided. For example, the main compartment could be round, elliptical, square, or any other suitable shape. Depending on the shape of the main compartment, the main compartment may be defined by a rear wall and a single main compartment wall or a plurality of main compartment walls.

The main compartment 1005 is in fluid communication with a main compartment gases inlet 1009. In the form shown, the main compartment gases inlet 1009 comprises an aperture in a lower wall 1017 of the filter body. Alternatively, the main compartment may be in fluid communication with a plurality of gases inlets 1009. The main compartment 1005 will receive gases via the gases inlet(s) 1009. For example, the main compartment 1005 may receive a main or primary gas or gases, such as oxygen, ambient air, a combination of oxygen and ambient air, or another suitable gases or combinations of gases via the gases inlet(s) 1009. The main compartment may receive oxygen and/or ambient air from a valve manifold 4001, 5001, 6001, 7001, 8001, 9001 described in more detail below. In some configurations, oxygen passes through the valve manifold 4001, 5001, 6001, 7001, 8001, 9001 and into the filter, and ambient air passes around the valve/valve manifold and into the filter.

As well as defining the main compartment 1005, the main compartment walls 1013, 1015, 1017, and 1019 also define a substantially planar main compartment gases outlet. The gases outlet of the main compartment is provided by the opening between the walls 1013, 1015, 1017, 1019 opposite to the rear wall 1021. The gases inlet(s) 1009 is/are arranged so that gases enter the main compartment 1005 in a gas flow direction (along a main compartment gas flow inlet axis) that is substantially parallel to the side walls 1013, 1015 of the main compartment, as shown by the large arrow adjacent the gases inlet 1009 in FIG. 10. The gases outlet of the main compartment 1005 is arranged so that gases exit the main compartment 1005 in a gas flow direction (along a main compartment gas flow outlet axis) that is offset from the gas flow inlet axis. The direction of gas flow through the gases outlet may be generally transverse to the direction of gas flow through the gases inlet. In the configuration shown, the gas flow direction through the gas flow outlet is substantially perpendicular to the rear wall 1021 of the filter body 1003. The gas flow outlet could instead be provided in, for example, an end wall of the filter body while still being offset from the gas flow inlet 1009.

Advantages are provided by having the flow turning direction through the filter. The filter module 1001 is able to be inserted into and removed from the top of the apparatus, rather than being clipped onto the side. When the filter module 1001 is installed in the apparatus, the alternative gas supply inlet 1011 is located on the top of the apparatus. The user or medical practitioner may visually observe that an alternative gas supply is connected from substantially any point in a room. The filter module 1001 has a relatively small filter volume and physical size. As a result, the time it takes for gases to pass through the filter module to the blower and sensors is relatively quick. The shorter the flow path, the lesser the lag between the signal provided to the valve (i.e. to adjust the oxygen:air proportions) and the oxygen:air proportions detected by the sensors.

The main compartment may include additional walls, baffles, or the like to direct flow inside the main filter compartment.

The filter body 1003 also has a first relatively small sub-compartment 1007. The sub-compartment 1007 is located at least partly within the main compartment 1005.

The sub-compartment 1007 is defined by at least one main compartment wall bounding a main compartment volume. The sub-compartment 1007 is defined by two substantially vertical sub-compartment side walls 1023, 1025, a lower wall 1027, and a portion of the rear wall 1021 of the filter body 1003. The sub-compartment is shown as being an elongate. However, any suitable shape could be provided. For example, the sub-compartment could be round, elliptical, square, or any other suitable shape. Depending on the shape of the sub-compartment, the sub-compartment may be defined by a rear wall and a single sub-compartment wall or a plurality of sub-compartment walls.

The sub-compartment 1007 is in fluid communication with a first sub-compartment gases inlet 1011, which forms an alternative gas supply inlet. That alternative gas supply inlet may receive a secondary or alternative gas such as oxygen, or any other gas or gases, from, for example: a tube/line from a hospital (or other medical facility) wall supply rotameter; a tube/line from a nearby gas tank; a tube/line from an oxygen concentrator. By providing sub-compartment(s) in the filter, the use of a plurality of separate filters can be avoided. A single, replaceable filter module can be used to filter gases from multiple sources.

Figure 50:
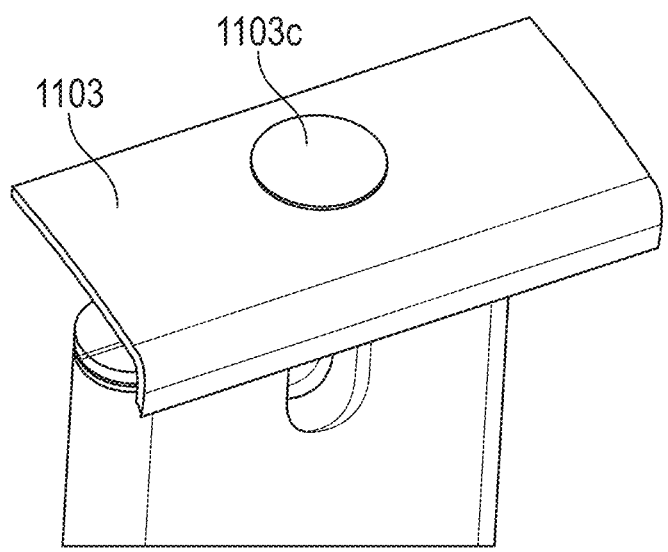
FIG. 50 is a partial overhead view of a valve module with a cap or lid.
Figure 51:
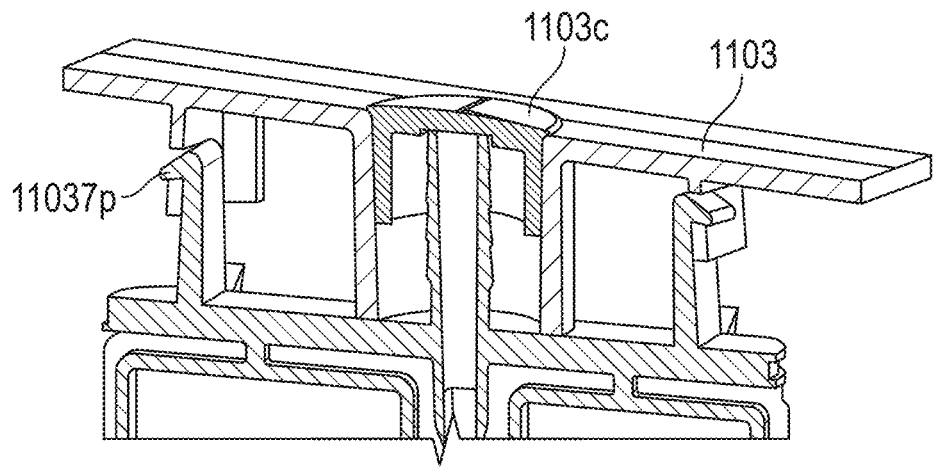
FIG. 51 is a partial sectional view through a valve module.

By connecting to the alternative gas supply inlet 1011, the gas supply is not regulated by the valve module. This is practical where the user or medical practitioner wants to manually control the supply of oxygen (or other gas). When not in use, the alternative gas supply inlet may be closed with a cap/lid 1103C that is arranged to be substantially flush with the panel portion 1103 FIG. 50). If there is nothing connected to the alternative supply inlet 1011, and it is not closed with a cap/lid, ambient air may also be drawn into the alternative gas supply inlet 1011.

When the filter module 1001 is installed in the apparatus 10, the alternative gas supply is located on the top of the apparatus. The user or medical practitioner may visually observe that an alternative gas supply is connected from substantially any point in a room. Additionally, it will be visually apparent to a user whether the filter is installed in the apparatus or missing.

It should be appreciated that, in alternative configurations, the alternative pas supply inlet 1011 may be accessible from the side or rear of the apparatus.

In the form shown, the first sub-compartment gases inlet 1011 comprises an aperture that extends through the upper wall 1019 of the filter body and through an inlet connector 1039. Alternatively, the sub-compartment 1007 may be in fluid communication with a plurality of gases inlets 1011. The sub-compartment 1007 may receive gases from an alternative supply to that of the main compartment, via the gases inlet 1011 and connector 1039. For example, the sub-compartment 1007 may receive oxygen or another suitable gases or combinations of gases. The first sub-compartment gases inlet 1011 may receive gases that have not come from a valve module 4001, 5001, 5001, 7001, 8001, 9001, so the gases received from the first sub-compartment gases inlet 1011 are not regulated by the apparatus. For example, the first sub-compartment gases inlet 1011 may receive oxygen from a wall supply rotameter that can be manually adjusted by a user. When an alternative oxygen supply is not connected to the first sub-compartment gases inlet 1011, ambient air may be drawn through the first sub-compartment gases inlet.

The sub-compartment may be provided in an upper part of the filter body, or may be provided in a different part of the filter body such as a side or lower part of the filter body.

Figure 14:
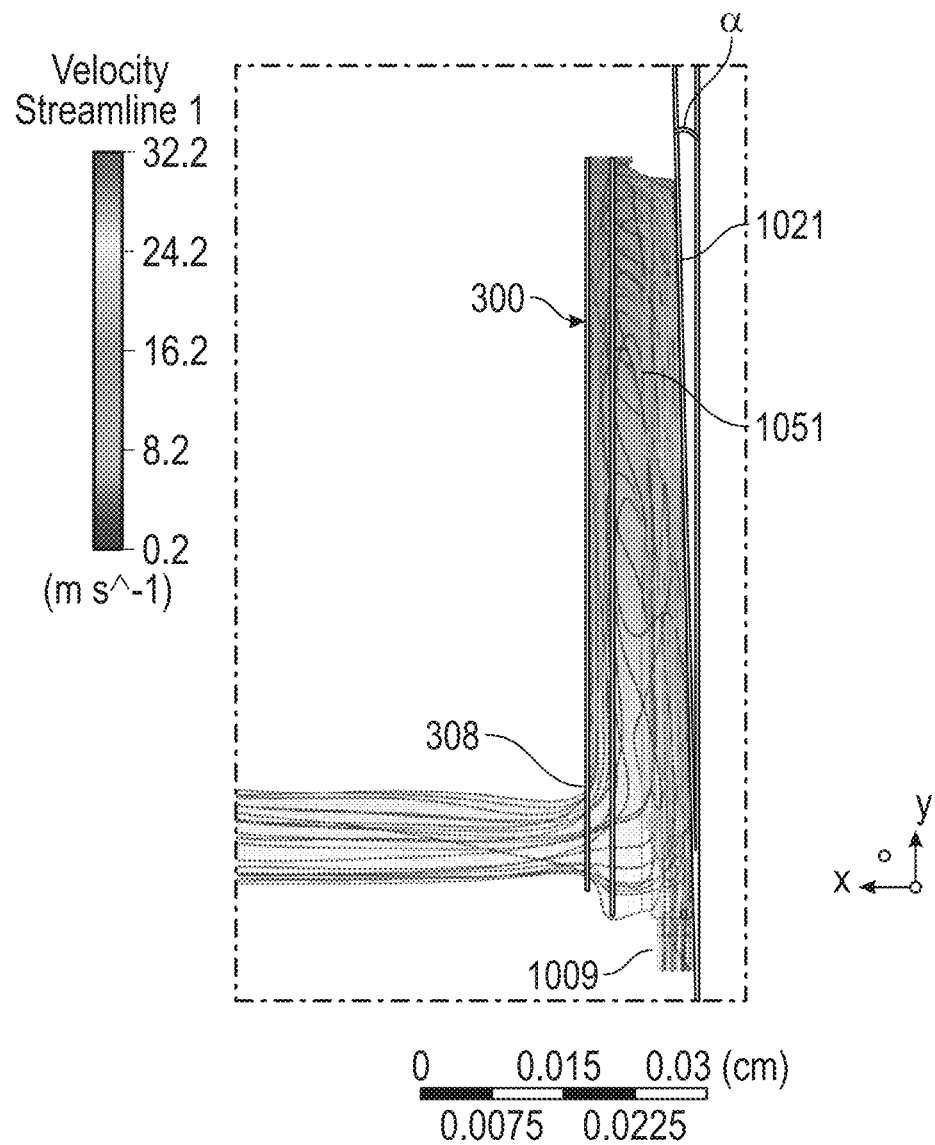
FIG. 14 is a fluid model showing gases flow through the tapered filter module.

As well as defining the first sub-compartment 1007, the sub-compartment walls 1023, 1025, 1027, also define a substantially planar sub-compartment gases outlet. The gases outlet of the sub-compartment is provided by the opening between the walls 1023, 1025, 1027, 1019 opposite to the rear wall 1021. The gases inlet(s) 1011 is/are arranged so that gases enter the first sub-compartment 1007 in a gas flow direction (along a first sub-compartment gas flow inlet axis) that is substantially parallel to the side walls 1023, 1025 of the sub-compartment, as shown by the top downward directed arrow in FIG. 10. The gases outlet of the first sub-compartment 1007 is arranged so that gases exit the sub-compartment 1007 in a gas flow direction (along a first sub-compartment gas flow outlet axis) that is offset from the gas flow inlet 1011 axis. The direction of gas flow through the gases outlet may be generally transverse to the direction of gas flow through the gases inlet. In the configuration shown, the gas flow direction through the gas flow outlet of the sub-compartment is substantially perpendicular to the rear wall 1021 of the filter body 1003 and is substantially parallel to the gas flow direction through the gas flow outlet of the main compartment. When viewed from the position of FIG. 12A, the gas flow direction is out of the page. FIG. 12B is a perspective view showing the direction of gas flow out of the filter. FIG. 14 is a fluid model showing gases flow through the tapered filter module.

The sub-compartment gas flow outlet could instead be provided in, for example, an end wall of the filter body while still being offset from the first sub-compartment gases inlet 1011.

The sub-compartment walls 1023, 1025, 1027, provide a barrier to direct all gases from the gases inlet 1011 through the sub-compartment gases outlet and through the filter medium 1051 (described below). Without the sub-compartment 1007, it would be possible for some gases from the first sub-compartment gases inlet 1011 to pass through the main compartment 1005 and cut the inlets 1009 (against the flow of incoming main compartment gases), without passing through the filter medium 1051. With the configuration with the sub-compartment, once cases have passed from the sub-compartment through the filter medium 1051, they may then only escape the system if they were to pass back through the filter medium 1051 (against the flow of gases passing through the filter medium) and out the inlets 1009, 1011. Therefore, the sub-compartment 1007 substantially enhances the retention and subsequent entrainment of gases in the system by directing all gases from the sub-compartment gases inlet 1011 through the filter medium which ensures all gases are filtered. When the gases entering the system via the sub-compartment gases inlet comprise oxygen, that enhances entrainment of oxygen in the system.

In some configurations, the filter body 1003 may comprise a plurality of sub-compartments located at least partly within the main compartment 1005. In some configurations, the filter body comprises one sub-compartment, two sub-compartments, or three or more sub-compartments. In some configurations, the filter body 1003 may only have a main compartment 1005 and may not have any sub-compartments. The different sub-compartments may be used to deliver different secondary or alternative gases to the apparatus 10. By way of example only, one of the sub-compartments may deliver oxygen and one of the sub-compartments may deliver heliox to the apparatus 10. Another example is that one of the sub-compartments may deliver oxygen and one of the sub-compartments may deliver ambient air to the apparatus 10.

Figure 10:
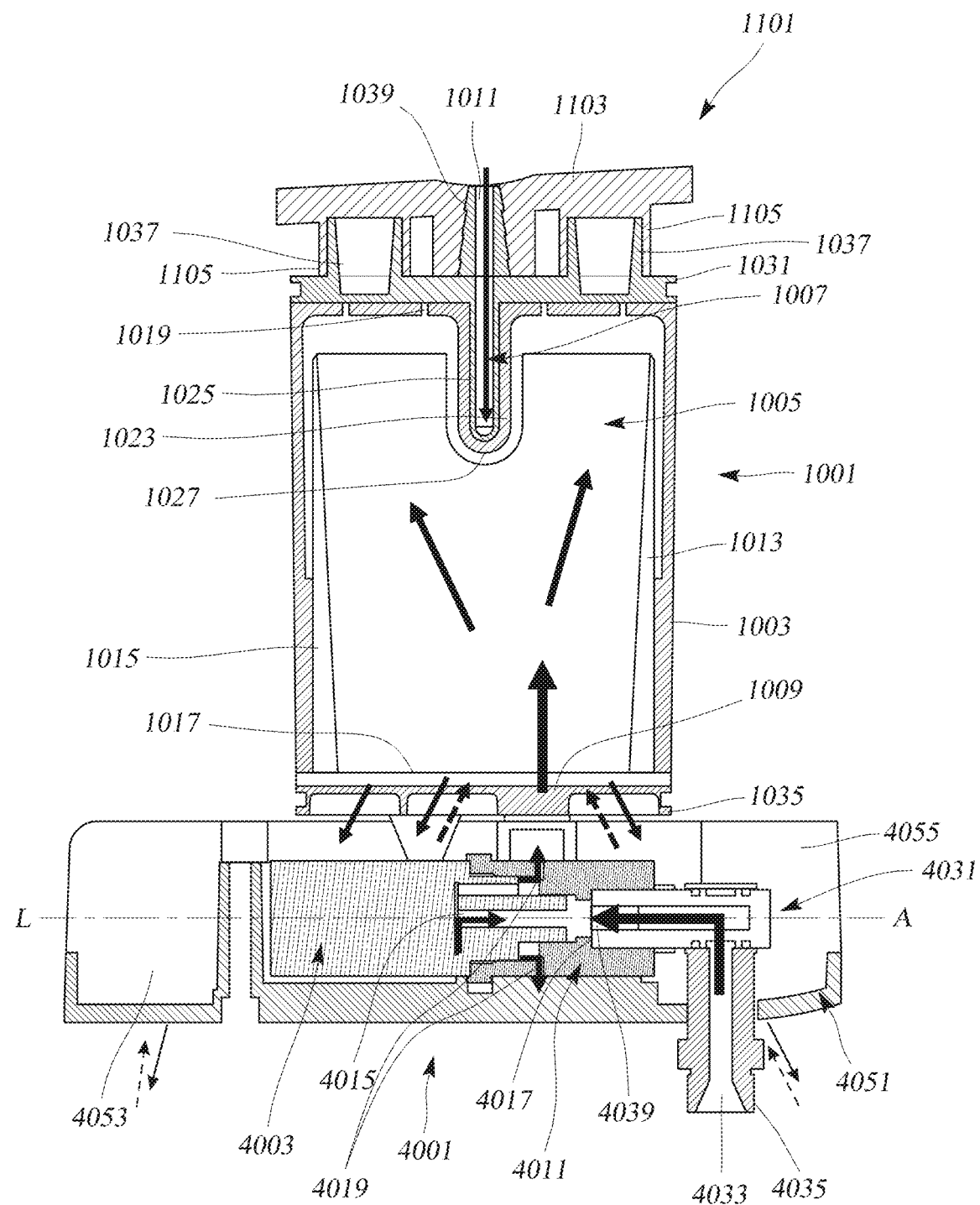
FIG. 10 is a sectional view showing the gas flow path through the filter module and the valve module.
Figure 11A:
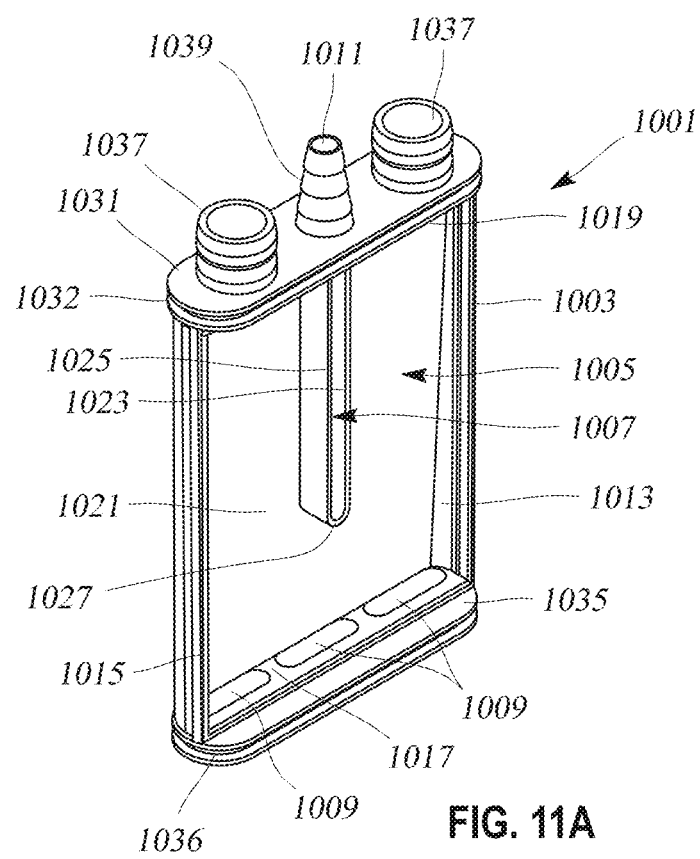
FIG. 11A is a front right overhead perspective view of a filter body of a first configuration filter module.

In some configurations, such as that shown for filter 1001 in FIGS. 10 and 11A, the sub-compartment(s) 1007 is/are located entirely within the main compartment 1005. Alternatively, in some configurations, the sub-compartment(s) 1007 is/are located partly externally of the main compartment 1005. In some configurations, at least one sub-compartment is located entirely within the main compartment 1005 and at least one sub-compartment is located partly externally of the main compartment 1005.

The filter module 1001 seal(s) about an external periphery of the filter body 1003 to sealingly engage the filter module in the housing of the apparatus. The seals and filter module 1001 are arranged such that gases entering the apparatus are forced to pass through the filter before entering the gas flow path of the apparatus (i.e. before passing to the motor and/or sensor module 400). That is, the housing has a gases outlet for delivering a flow of gas to the patient, a gases inlet, and a sealed gases path between the gases inlet and the gases outlet, where the sealed gases path comprises the filter to filter gases that have been received from the first gases inlet. It will be understood that the filter comprises the filter body, the gases inlet, the gases outlet, and the filter medium that is arranged to filter gases in, or exiting, the filter body.

An upper part of the filter body comprises a transverse upper body portion 1031. An underside of the transverse upper body portion 1031 provides the wall 1019. An annular recess 1032 is provided around the periphery of the upper body portion 1031 and is arranged to receive a soft seal such as an O-ring seal or 'wiper' seal 1033. The wiper seal may be integrally formed with the upper body portion 1031. For example, the wiper seal 1033 may be formed as an outwardly projecting flange of the body portion material of the filter. The thin material allows sufficient flexibility to form the wiper seal. As another example, the upper body portion 1031 may comprise a compliant material that is overmoulded onto the remainder of the filter body, and that comprises the seal 1033 and optionally the components 1037 and 1039. As another example, the seal 1033 may comprise a compliant material that is overmoulded onto the upper body portion 1031. In some configurations, the wiper seal 1033 may taper outwardly; i.e., an outward portion of the wiper seal 1033 may be thinner than a more inward portion of the wiper seal. The soft seal seals between the upper body portion 1031 and the wall of the filter receptacle 300 when the filter body is positioned in the filter receptacle 300, to provide sealing engagement between the filter and the filter receptacle and to inhibit bacteria entry into the filter.

A lower part of the filter body comprises a transverse lower body portion 1035. An upper side of the transverse lower body portion 1035 provides the wall 1017. An annular recess 1036 is provided around the periphery of the lower body portion 1035 and is arranged to receive a soft seal such as an O-ring seal or 'wiper' seal. The wiper seal may be integrally formed with the lower body portion 1035. For example, the lower wiper seal may be formed as an outwardly projecting flange of the body portion material of the filter. The thin material allows sufficient flexibility to form the wiper seal. As another example, the lower body portion 1035 may comprise a compliant material that is overmoulded onto the remainder of the filter body, and that comprises the seal. As another example, the seal may comprise a compliant material that is overmoulded onto the lower body portion 1035. In some configurations, the lower wiper seal may taper outwardly; i.e., an outward portion of the lower wiper seal may be thinner than a more inward portion of the wiper seal. The soft seal seals between the lower body portion 1035 and the wall of the filter receptacle 300 when the filter body is positioned in the filter receptacle 300, to provide sealing engagement between the filter and the filter receptacle and to inhibit bacteria entry into the filter.

As can be seen from FIG. 11B, the upper and lower body portions 1031, 1035 are deeper than the portion of the body that houses the main compartment 1005 and sub-compartment 1007, so that space is provided between the gases outlet ports of the main compartment 1005 and the sub-compartment 1007 and filter medium 1051 (described in more detail below) and the wall of the filter receptacle 300. That enables gases to flow out of the main compartment 1005 and sub-compartment 1007 and through the filter medium 1051, in the filter receptacle 300, and out through the aperture 208 to be delivered to the motor and/or sensor module 400.

Figure 2A:
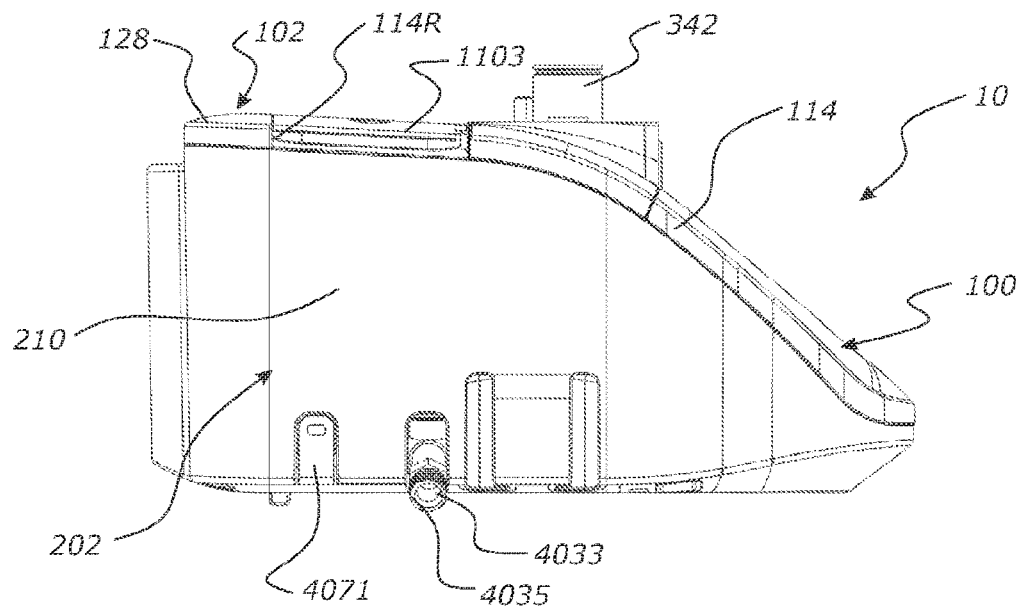
FIG. 2A is a left side view of the flow therapy apparatus showing an exemplary location of the valve module and the filter module.

The filter module comprises a filter module top panel 1101 with a panel portion 1103. The filter module top panel is attached or attachable to the filter body. As shown in FIG. 2A, the left side upper wall 114 of the upper chassis 102 of the main housing comprises a recess 114R to receive the panel portion 1103 of the filter module top panel.

The upper body portion 1031 comprises a plurality of snap-fit connectors 1037 for permanently engaging with complementary snap-fit connectors 1105 on the filter module top panel 1101. The filter body 1003 and the top panel 1101 are moulded separately and then permanently assembled together. The connectors 1037 are arranged to be received within the connectors 1105 of the top panel 1101 as shown in FIG. 10, and the snap-fit connectors 1105, 1037 are provided with positive engagement features such as annular projections and/or recesses to enable the snap-fit between the connectors. The snap-fit connectors 1105 extend downwardly from the underside of the panel portion 1103 of the top panel 1101. In some configurations, the filter top panel is attachable to the filter body by way of a snap flit, clips, fasteners, or other suitable attachments. Alternatively, the filter top panel 1101 may be integrally moulded with the filter body 1003.

As shown in FIGS. 3A and 4, the panel portion 1103 of the filter top panel 1101 is arranged to be substantially flush with the main housing of the apparatus, and in particular with the left side wall 114, when the filter 1001 is engaged with the housing.

The filter top panel 1101 is made from the same material as an adjacent portion of the housing of the apparatus, for example as the left side wall 114 of the upper chassis. In some configurations, the filter top panel 1101 and the left side wall 114 of the upper chassis is made of polycarbonate or another suitable polymeric material.

In some configurations, the filter top panel 1101 comprises a handling feature to aid in insertion and/or removal of the filter module 1001 from the filter receptacle 300 of the housing of the apparatus, such as when lifting the filter 1001 out of engagement with the filter receptacle 300. In some configurations, the filter handling feature comprises a ridge, groove, or grip. The filter handling feature may be provided at a periphery of the panel portion 1103 of the filter top panel 1101. For example, the filter handling feature may be provided at a portion of the panel portion 1103 of the filter top panel that is adjacent the angled upper chassis surface 130 that is shown in FIG. 4, to provide access to the handling feature. However, the filter handling feature may be provided elsewhere on the filter top panel 1011. In some configurations, the filter top panel comprises a plurality of filter handling features.

An alternative gas supply connector 1039 is in fluid communication with the sub-compartment and projects upwardly from the upper body portion 1031 of the filter body 1003 and provides an alternative gas supply inlet into the filter body 1003.

That alternative gas supply inlet may receive oxygen, or any other gas, from, for example: a tube/line from a hospital (or other medical facility) wall supply rotameter; a tube/line from a nearby gas tank; a tube/line from an oxygen concentrator.

By connecting to the alternative gas supply inlet, the gas supply is not regulated by the valve module. This is practical where the user or medical practitioner wants to manually control the supply of oxygen or other gas. When not in use, the alternative gas supply inlet may be closed with a closure such as a cap or lid (not illustrated).

If there is nothing connected to the alternative supply inlet, and it is not closed with a closure, ambient air may also be drawn into it.

When the filter module 1001 is installed in the apparatus, the alternative gas supply is located on the top of the apparatus. The user or medical practitioner may visually observe that an alternative gas supply is connected from any point in a room.

It should be appreciated that, in alternative configurations, the alternative gas supply inlet may be accessible from the side or rear of the apparatus.

The connector 1039 comprises a through-passage that provides the gases inlet 1011 for the first sub-compartment 1007. The alternative gas supply inlet connector 1039 is arranged to be fluidly connected to an alternative gas supply line. In the form shown, the connector 1039 is an elongate tapering connector suitable for releasably connecting semi-rigid gas supply tubes which do not have a complementary end connector. Such an elongate tapering connector may include one or more gas supply line retention enhancement features. For example, the connector may comprise a barb at or adjacent and upper end of the gas supply line connector. One example is 'Christmas tree' type connector with a plurality of barbs, for example. The connector could alternatively be a different configuration. In the event that the connector 1039 breaks (i.e. due to excessive force being applied to the alternative gas supply line), the filter module 1001 is advantageously replaceable without having to service the whole apparatus.

Figure 11B:
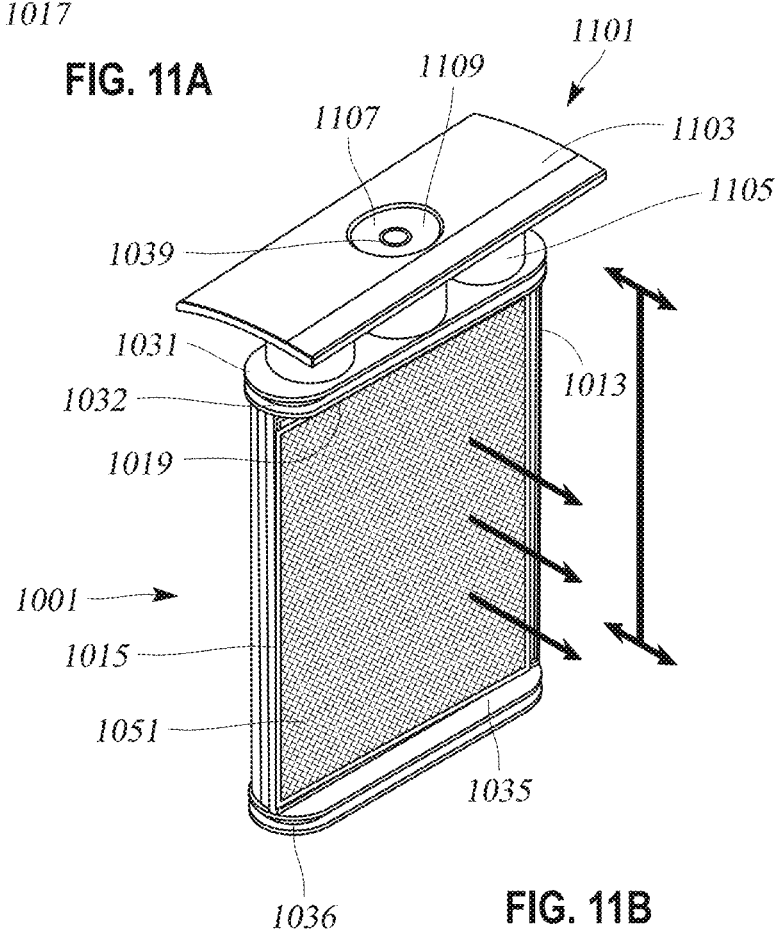
FIG. 11B is a front right overhead perspective view of the first configuration filter comprising the filter body, filter medium, and filter top plate.
Figure 11C:
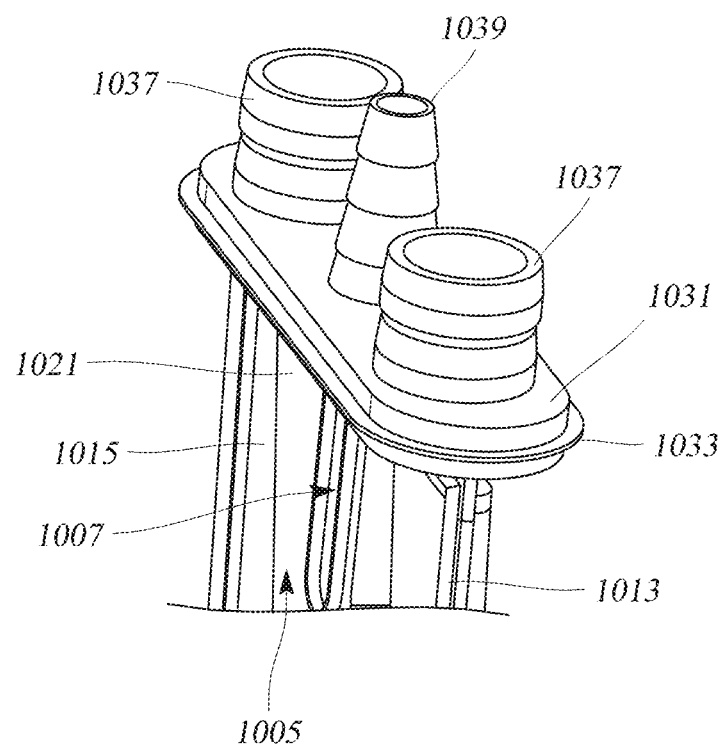
FIG. 11C is an overhead perspective view of an upper portion of the filter body.
Figure 11D:
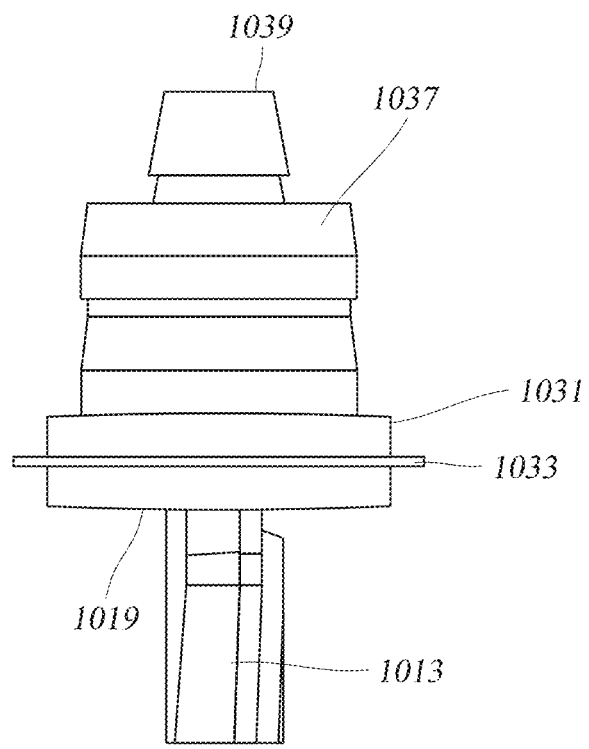
FIG. 11D is an end view of the upper portion of the filter body.

As shown in FIG. 11B, the filter top panel 1101 comprises an annular wall 1107 that extends downwardly from the panel portion 1103 and that forms an opening 1109 that exposes and protectively surrounds the gas supply line connector 1039.

Figure 41:
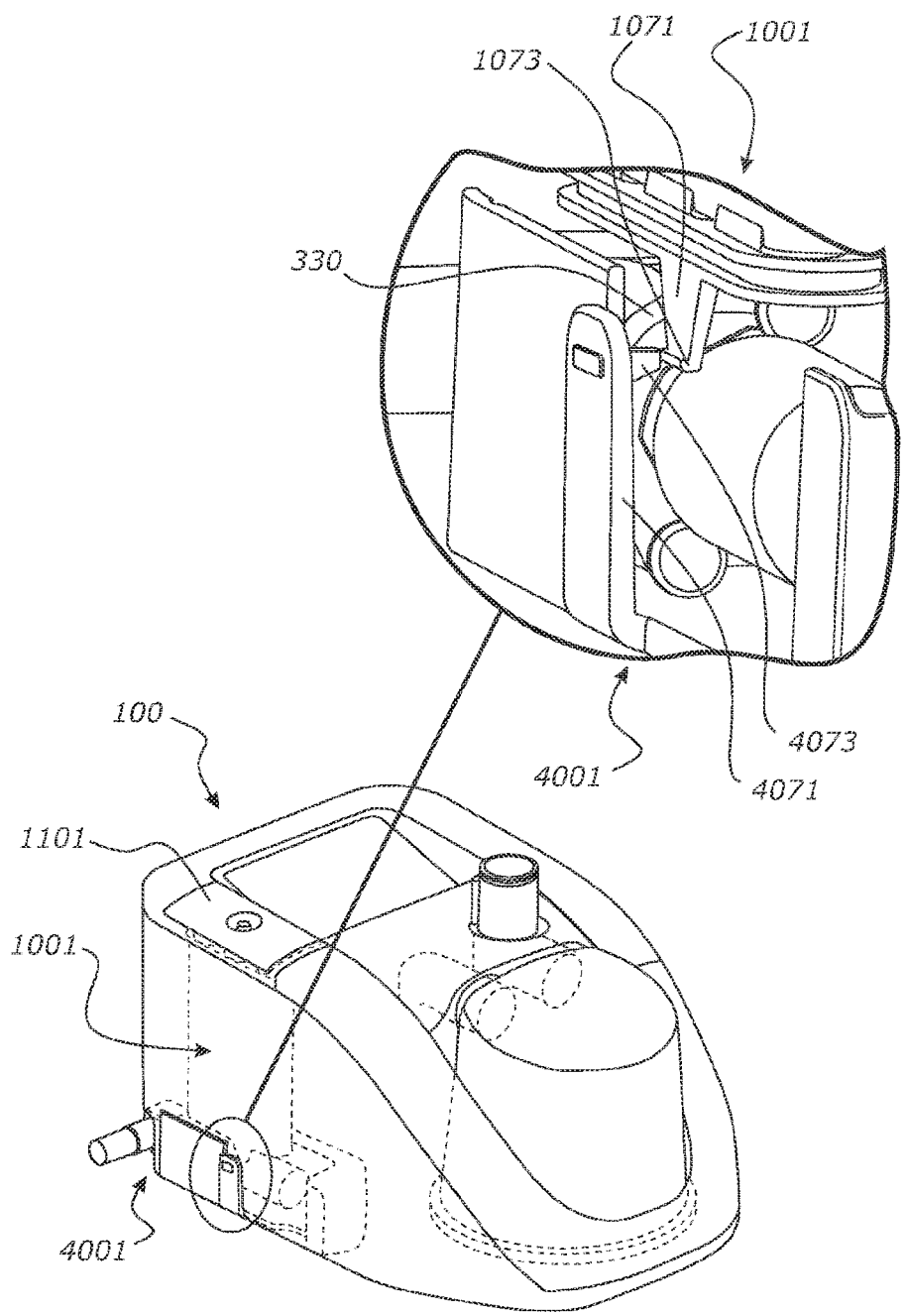
FIG. 41 is a front left overhead perspective view of an apparatus for delivering a flow of gas, showing a filter retention/release feature for one of the filter modules.
Figure 53:
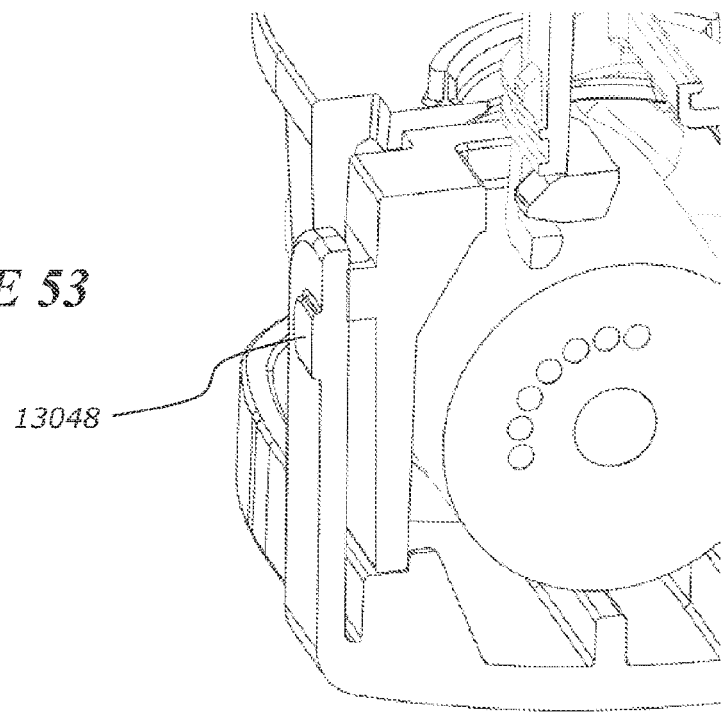
FIG. 53 is a cutaway view of a release tab.
Figure 54:
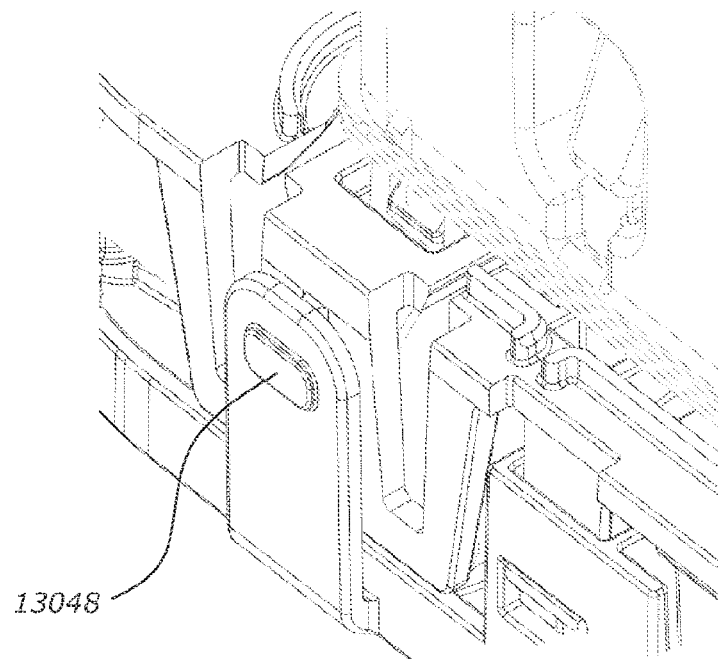
FIG. 54 is a partial perspective view of the release tab.
Figure 55:
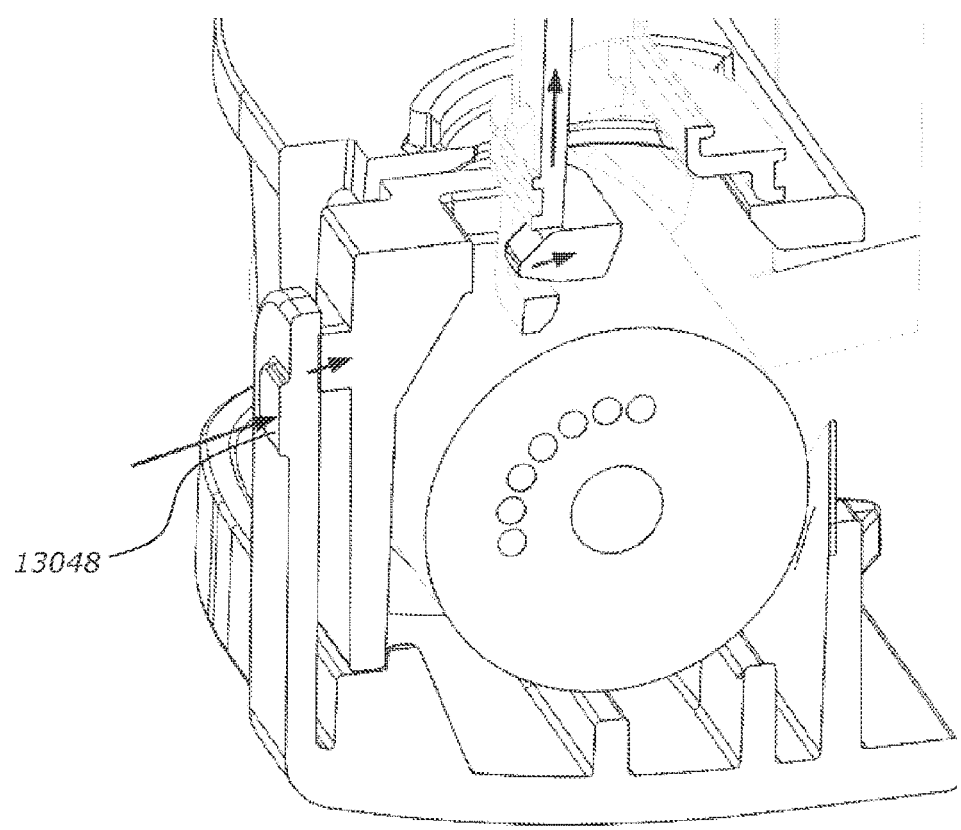
FIG. 55 is a cutaway view of the release tab.
Figure 56:
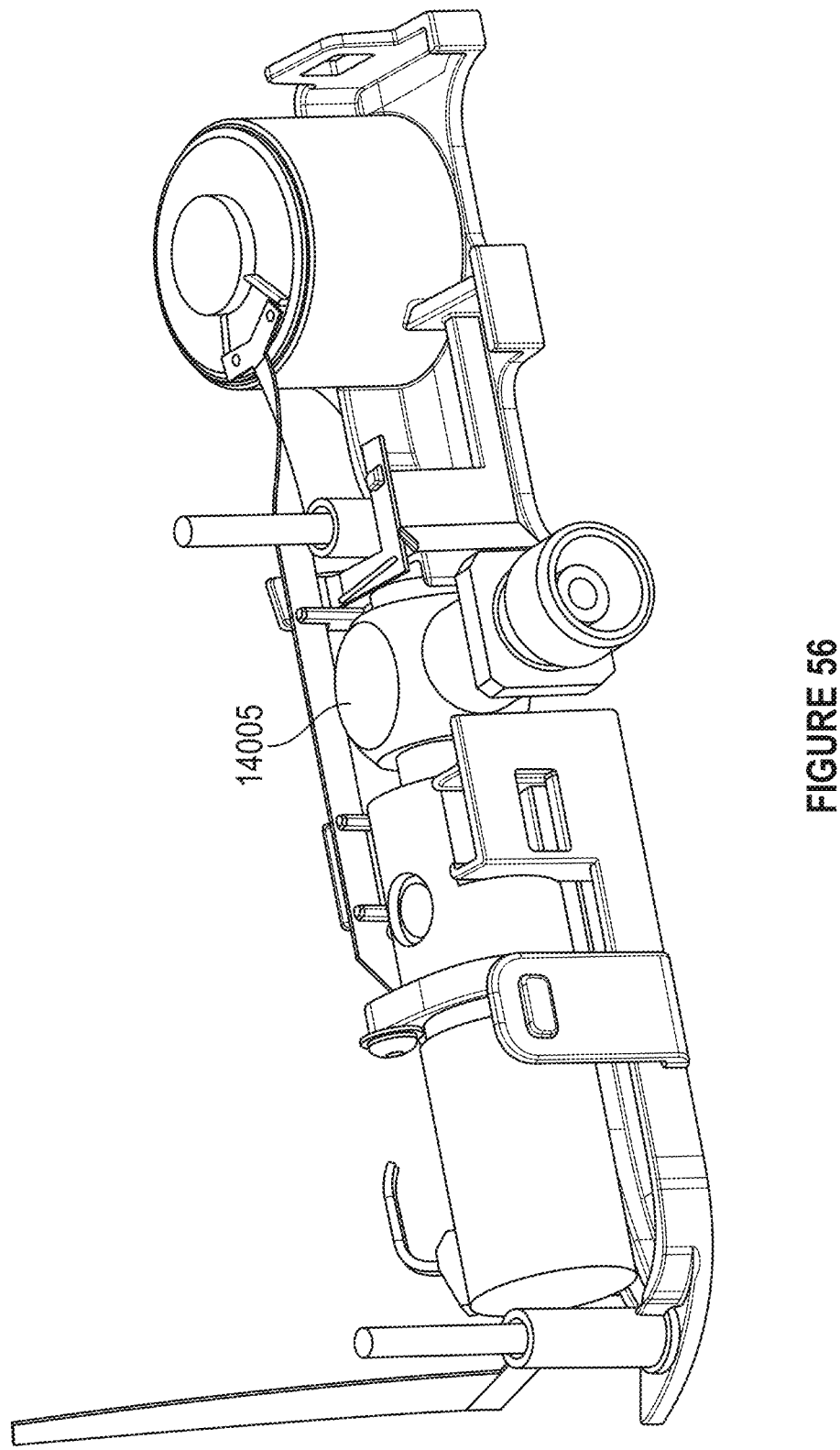
FIG. 56 is a perspective view of another valve module.

As shown in FIG. 41, a filter engagement tab 1071 with a projection 1073 extends from the bottom of the filter body 1003. When the filter 1001 is engaged in the filter receptacle 300, the engagement tab 1071 engages a retention block 330, which is integrally formed in the lower chassis 202 as shown in FIG. 41. The filter engagement tab 4071 secures the filter module in place in the apparatus. The securement is such that the filter module will not be accidentally removed from the apparatus if a gas line attached to the alternative gas supply connector 1039 is pulled. A release tab 4071 with a projection 4073, provided on the valve carrier 4051 that is described in more detail below with FIGS. 17, 18, and 19, may be pressed to displace the engagement tab 1071 from the retention block 330 and allow removal of the filter module from the filter receptacle 300. Therefore, the filter module release features can be formed as part of the filter module and valve module, without requiring additional components. With reference to FIGS. 53 to 55, the filter is released by pushing a release tab 13048 (also feature 4071 of FIG. 41).

The filter body may be made from polypropylene or any other suitable material.

Figure 12:
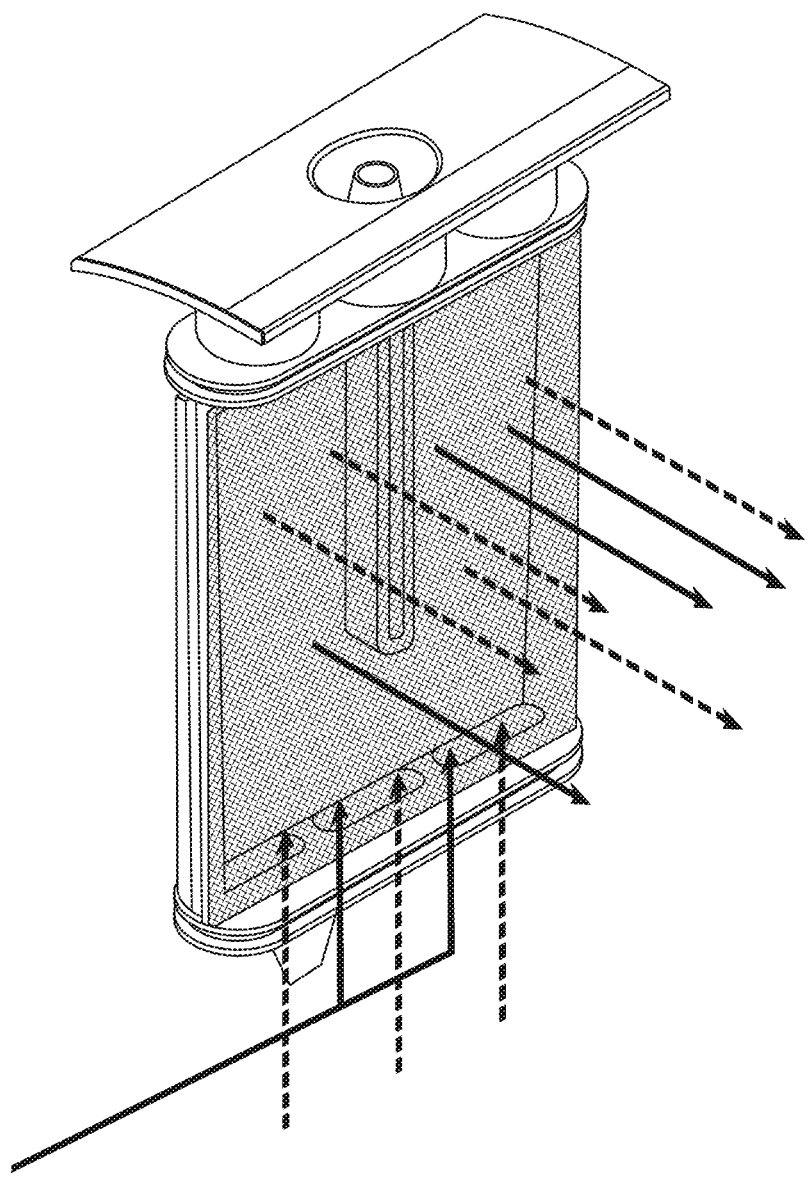
FIG. 12 is a schematic side view of the first configuration filter module, showing gas flow paths through the filter module, with the solid line arrows representing the flow of oxygen (or another gas), and the dashed line arrows representing the flow of ambient air.
Figure 12A:
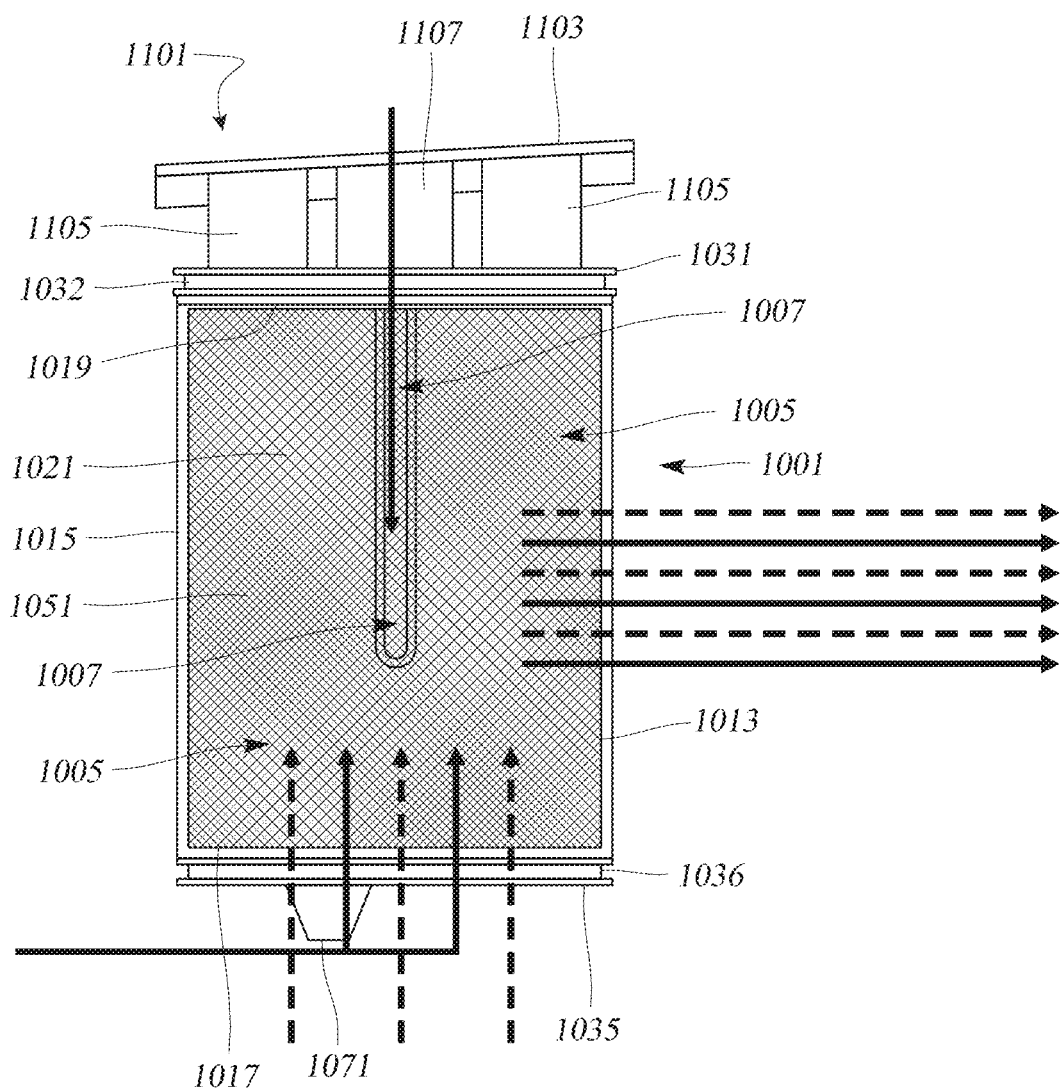
FIG. 12A is a schematic perspective view of the first configuration filter module, showing gas flow paths through the filter module, with the solid line arrows representing the flow of oxygen (or another gas), and the dashed line arrows representing the flow of ambient air.

Referring to FIGS. 11B and 12, a filter medium 1051 is associated with both the main compartment 1005 and the sub-compartment 1007, and is arranged to filter gases in, or exiting, the main compartment 1005 and the sub-compartment 1007. In the form shown, the filter medium 1051 covers or spans the main compartment 1005 and the sub-compartment 1007. In configurations with a plurality of sub-compartments, the filter medium may span the main compartment and the plurality of sub-compartments.

In the configuration shown, the filter medium 1051 is located on an external face of the filter body to filter gases exiting the main compartment 1005 via the main compartment gases outlet, and the sub-compartment 1007 via the sub-compartment gases outlet. Alternatively, in some configurations the filter medium 1051 may be positioned at least partly within the main compartment 1005 and the sub-compartment(s) 1007 to filter gases in the main compartment and the sub-compartment(s).

The filter medium may be an electrostatic filter medium. The electrostatic filter medium may be formed from a synthetic material such as spun polypropylene which develops an electrostatic charge as air/gas passing over the filter fibres creates friction. The electrostatic charge attracts dust, particulates, pollen, dust, mold spores etc—so is particularly suitable for effectively capturing respiratory irritants. Alternatively, other synthetic electrostatic filter medium material(s), other than polypropylene, may be employed.

During the ultrasonic welding process, the filter medium and the filter body both melt into each other to create the sealed edge. The materials may be the same (i.e. polypropylene), or could have different polymeric materials, such as polyethylene or polyester filters.

Alternatively, non-electrostatic filter medium material(s) may be employed. Non-electrostatic filters remove contaminant by a simple mechanical sieving effect—where a contaminant particle will not pass through openings smaller than the size of the contaminant particle itself.

In some configurations, the filter medium 1051 comprises substantially the same material as the filter body 1003. In some configurations, the filter body 1003 comprises polypropylene material or other suitable polymeric or synthetic material(s), and the filter medium 1051 comprises spun polypropylene or other suitable polymeric or synthetic material(s).

In some configurations, the filter medium 1051 comprises a different material to the material of the filter body 1003. In some configurations, the filter medium 1051 comprises wool fibres. The wool may act as an electrostatic filter medium, as described above. When using a natural fibre, such as wool or cotton, the filter medium does not melt, and instead it would be largely the filter body melting into the filter medium.

Figure 13:
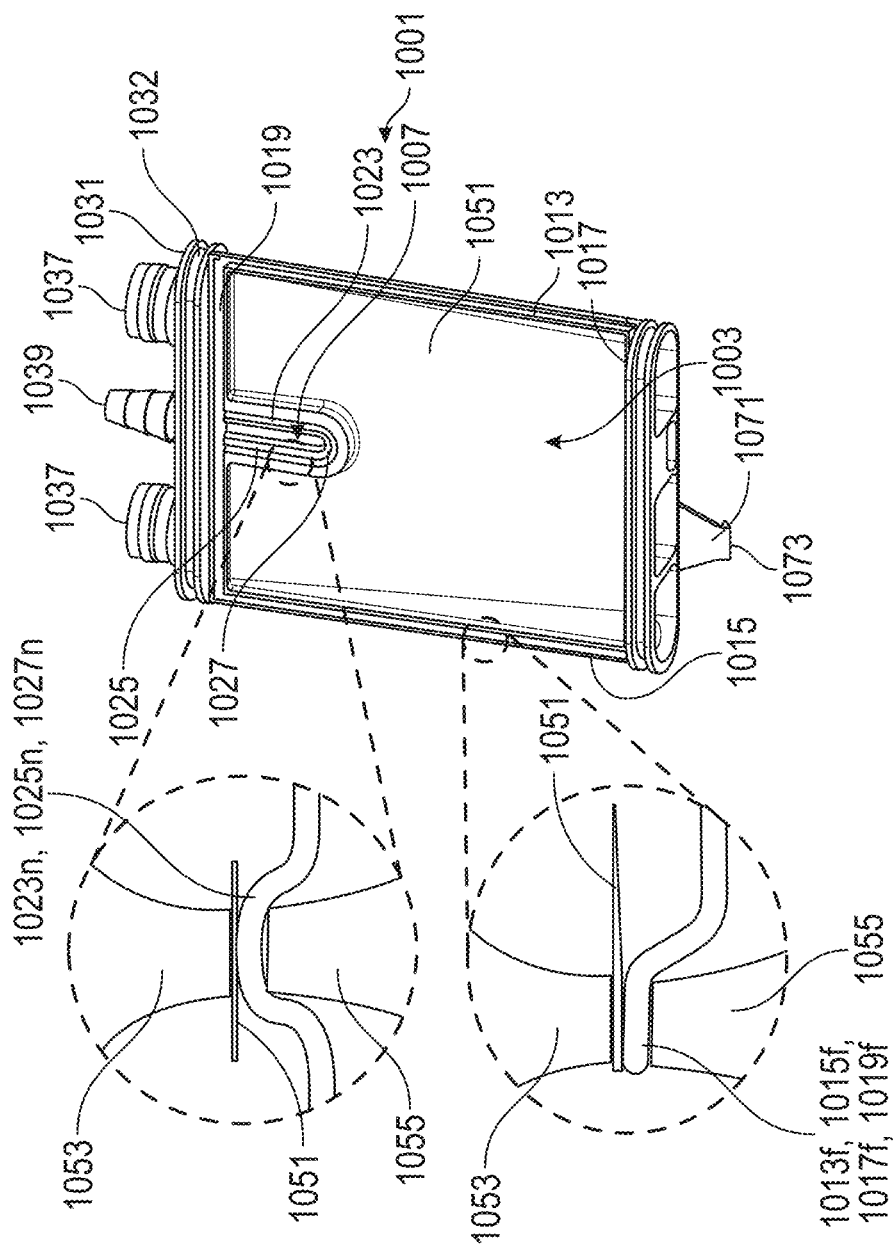
FIG. 13 is a view of the first configuration filter module, showing ultrasonic weld regions on wall portions of the filter body.

When suitable compatible materials are used, the filter medium 1051 may be ultrasonically welded to the filter body 1003, as shown schematically in FIG. 13. The examples given above (spun polypropylene, polyethylene or polyester filters, wool fibres, and cotton fibres) are examples of suitable materials of the filter medium 1051 that may be ultrasonically welded to the filter body 1003. The filter medium is ultrasonically welded to the at least one main compartment wall 1013, 1015, 1017, 1019 and the at least one sub-compartment wall 1023, 1025, 1027. The main compartment wall(s) 1013, 1015, 1017, 1019 and the sub-compartment wall(s) 1023, 1025, 1027 are shaped to provide a large ultrasonic weld area to provide a stable base for the ultrasonic weld and an increased area for the ultrasonic weld, provide enhanced strength of the ultrasonic weld, and avoid gaps between the filter medium and the filter body. The weld area is larger than an area provided by only the perimeter of the filter body. The top left portion of FIG. 13 shows the filter medium 1051 being ultrasonically welded to a substantially flattened 'n'-shaped wall formation 1023n, 1025n, 1027n of the walls 1023, 1025, 1027 of the sub-compartment, between an ultrasonic sonotrode 1053 and anvil 1055. The bottom left portion of FIG. 13 shows the filter medium 1051 being ultrasonically welded to a flange portion 1013f, 1015f, 1017f, 1019f of the walls 1013, 1015, 1017, 1019 of the main compartment, between an ultrasonic sonotrode 1053 and anvil 1055. If the same material is used for the filter medium and the filter body, the bond formed during ultrasonic welding is strong due to both bodies having a common molecular structure. Ultrasonic welding is advantageous to ensure that the filter medium is sealed with the filter body without gaps. It also avoids the bulk of mechanical clips or fasteners, and avoids the use of adhesives.

Rather than being ultrasonically welded to the filter body 1003, the filter medium could be permanently attached to the filter body in a different way, such as by using adhesive or mechanical fasteners for example. Alternatively, the filter medium may be releasably attached to the filter body by means of mechanical fasteners, releasable clips, or the like. Alternatively, the filter medium may be overmoulded onto the filter body.

At least a portion of the main compartment 1005 tapers inwardly such that a portion of the main compartment spaced further from the main compartment gases inlet 1009 has a smaller dimension than a portion of the main compartment adjacent the main compartment gases inlet 1009. Incoming gases may thereby be deflected substantially transversely toward/through the filter medium 1051. Substantially the entire main compartment 1051 may taper inwardly. In the form shown in FIGS. 13 and 14 for example, the rear wall 1021 of the filter body 1003, which is positioned on an opposite face of the main compartment to the filter medium, is angled at an angle α relative to the plane of the main compartment gases outlet and the filter medium 1051, to provide the tapering of the main compartment. In some configurations, the angle α may be more than 0° and up to about 45°, or may be more than 0° and up to about 40°, or may be more than 0° and up to about 30°, or may be more than 0° and up to about 20°, or may be more than 0° and up to about 10°, or may be more than 0° and up to about 5°, or may be between about 1° and about 4°, or may be between about 2° and about 3°. The angled wall deflects incoming gases toward the filter medium and may aid in providing even distribution of gases across the filter medium. In an alternative configuration, only a small part of the main compartment tapers inwardly. For example, in that configuration, part of the rear wall 1021 may be parallel to the filter medium, and part of the rear wall may be angled relative to the filter medium. In an alternative configuration, the main compartment may not be tapered.

The rear wall of the main compartment of the filter may optionally angle inwardly from bottom to top. The angled wall deflects incoming oxygen and/or air toward the filter medium.

Without the angled rear wall 1021 some oxygen and/or air may enter the main compartment 1005 from the inlets 1009, deflect off the top and side walls of the main compartment and recirculate back down toward the inlets 1009. Therefore, the angled rear wall 1021 may aid in the retention and subsequent entrainment of gases in the system by reducing or preventing recirculation, and subsequent loss, of gases from the main compartment 1005. The angled rear wall 1021 may additionally aid in directing incoming air and oxygen evenly across the surface area of the filter.

In an embodiment having sub-compartment(s), at least a portion of the sub-compartment spaced further from the sub-compartment gases inlet 1011 may have a smaller dimension than a portion of the sub-compartment adjacent the sub-compartment gases inlet 1011, to deflect gases substantially transversely toward/through the filter medium 1051. When the sub-compartment gases inlet 1011 is positioned opposite to the main compartment gases inlet 1009, the angles of taper of the sub-compartment and main compartment may be opposite to each other. Alternatively, the sub-compartment gases inlet may be positioned such that the rear wall of the sub-compartment may be co-incident to or co-planar with the rear wall of the main housing. The options outlined above for the main compartment also apply to the sub-compartment(s).

The filter module 1001 is also configured to minimise pressure drop by having one or more of: small gases inlets area to large gases outlets area; radiuses/rounded edges in the gases inlets and main compartment to smooth flow, particularly around the smallest gases inlet(s).

Figure 15:
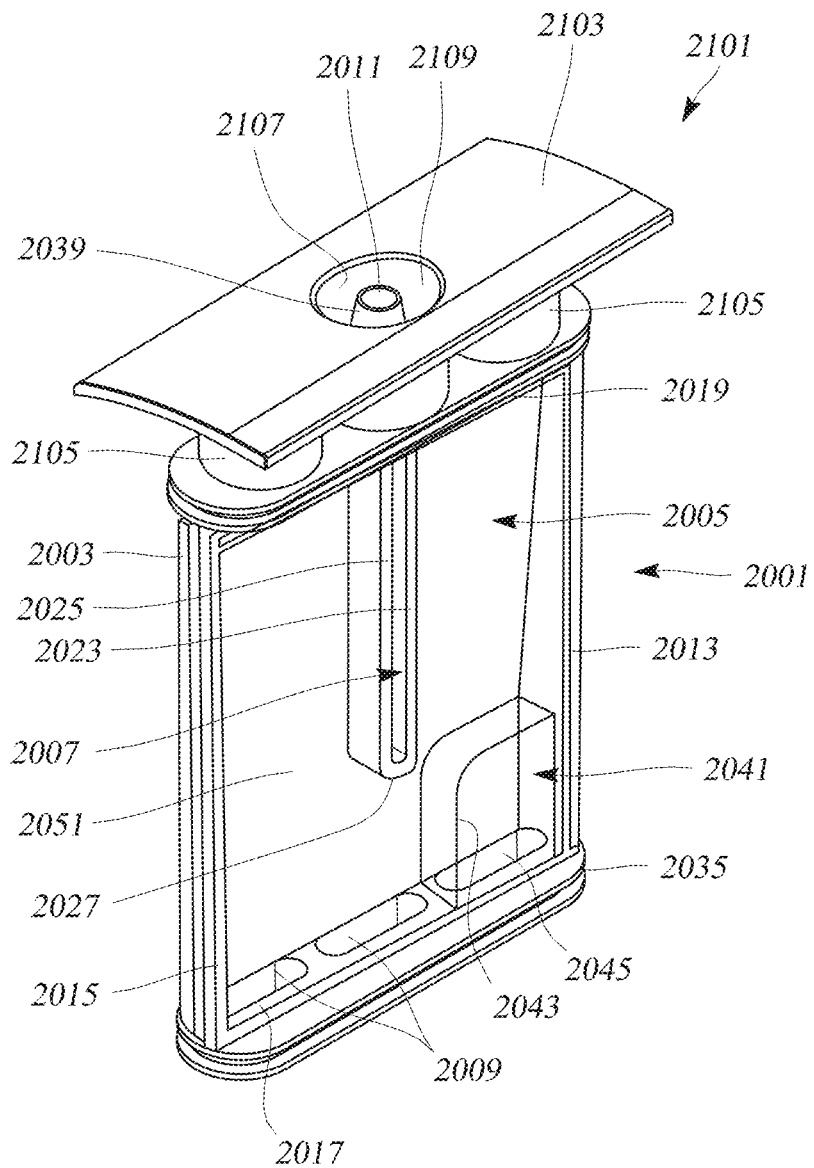
FIG. 15 is a front right overhead perspective view of a second configuration filter module.
Figure 16:
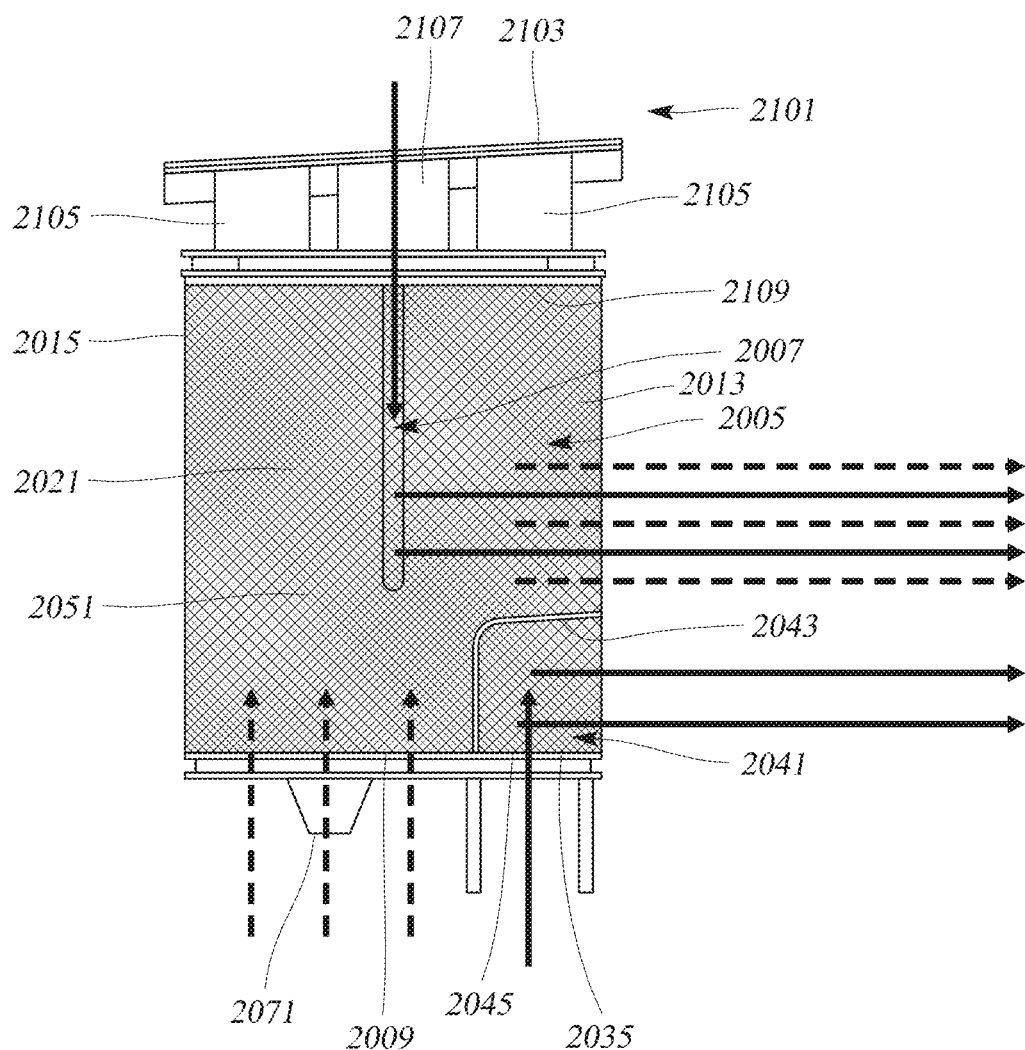
FIG. 16 is a side view of the second configuration filter module, showing gas flow paths through the filter module, with the solid line arrows representing the flow of oxygen (or another gas), and the dashed line arrows representing the flow of ambient air.
Figure 17:
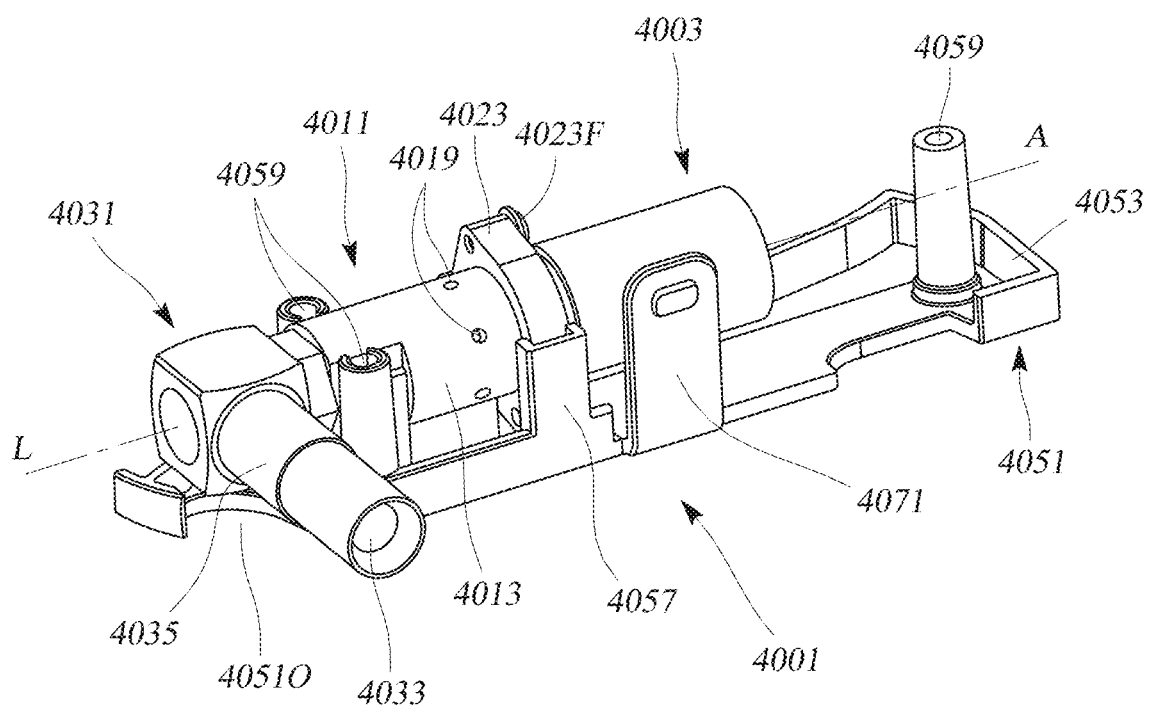
FIG. 17 is a rear side overhead perspective view of a first configuration valve module.
Figure 18:
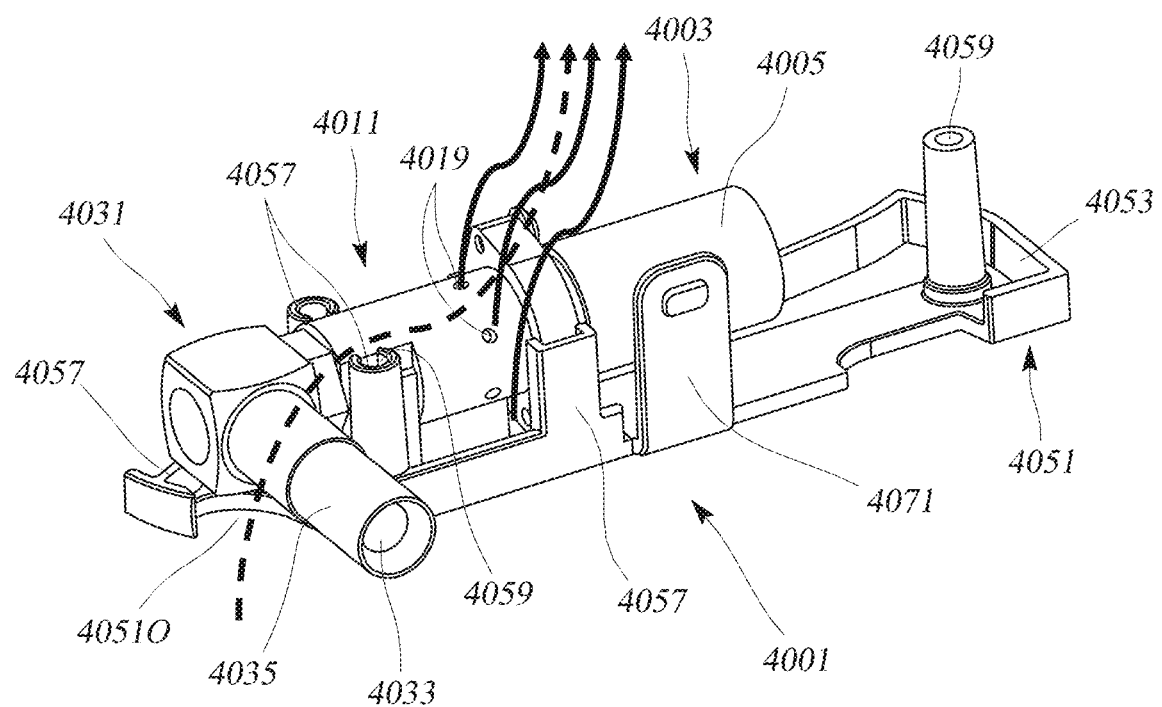
FIG. 18 is a rear side overhead perspective view showing the gas flow paths through the first configuration valve module, with the solid line arrows representing the flow of oxygen (or another gas), and the dashed line arrow representing the flow of ambient air.
Figure 19:
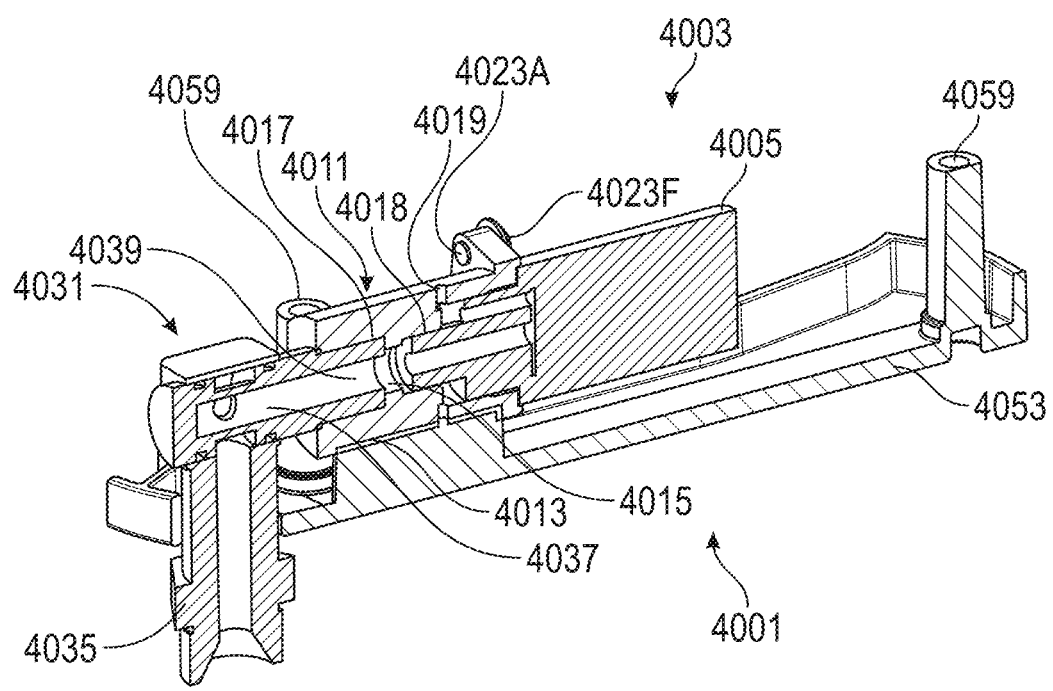
FIG. 19 is a sectional view through the first configuration valve module.

FIGS. 15 and 16 show a second configuration filter module 2001. Unless described below, the features, functionality, options, and advantages are all as outlined above for the first configuration, and like reference numerals indicate like parts with 1000 added to each numeral.

This filter module comprises a second sub-compartment 2041 at least partly within the main compartment 2005. In this configuration, the main compartment 2005 forms a first compartment, the first sub-compartment 2007 forms a second compartment, and the second sub-compartment 2041 forms a third compartment. The second sub-compartment 2041 is arranged to receive gas from a second sub-compartment gases inlet 2045 in a lower portion 2035 of the filter body 2003; for example, oxygen from the valve module. In this configuration, the main compartment 2005 may receive ambient air.

The wall(s) 2043, 2013, 2017 of the second sub-compartment form a substantially planar gases outlet from the second sub-compartment, through which gases can exit the second sub-compartment in a direction that is substantially parallel to the gas flow direction through the gases outlets of the main compartment 2005 and the first sub-compartment 2007. The filter medium 2051 spans the gases outlet of the second sub-compartment. The second sub-compartment may have a tapered configuration as described for the first sub-compartment.

Figure 28:
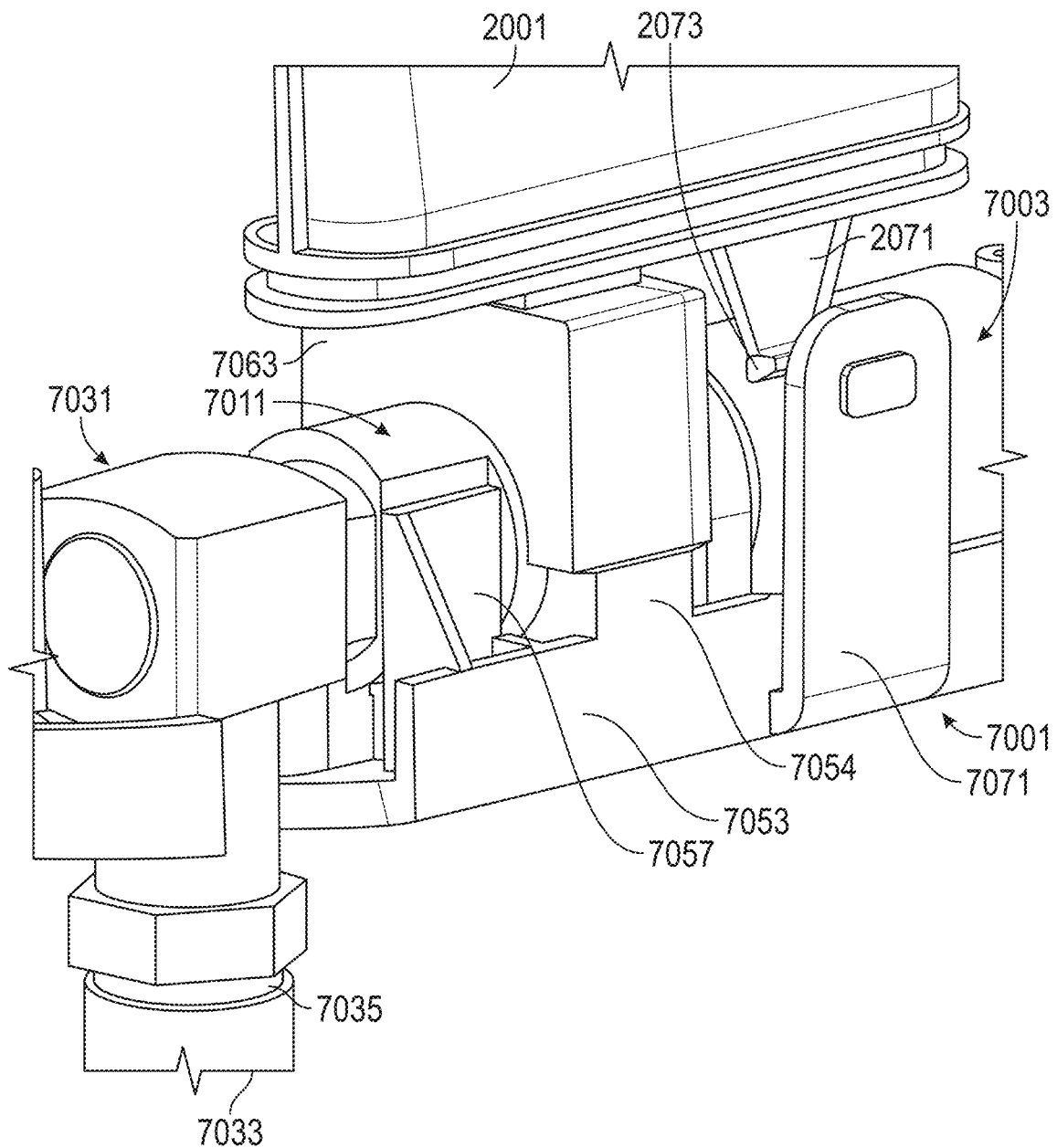
FIG. 28 is a rear side overhead perspective view of a fourth configuration valve module.
Figure 29:
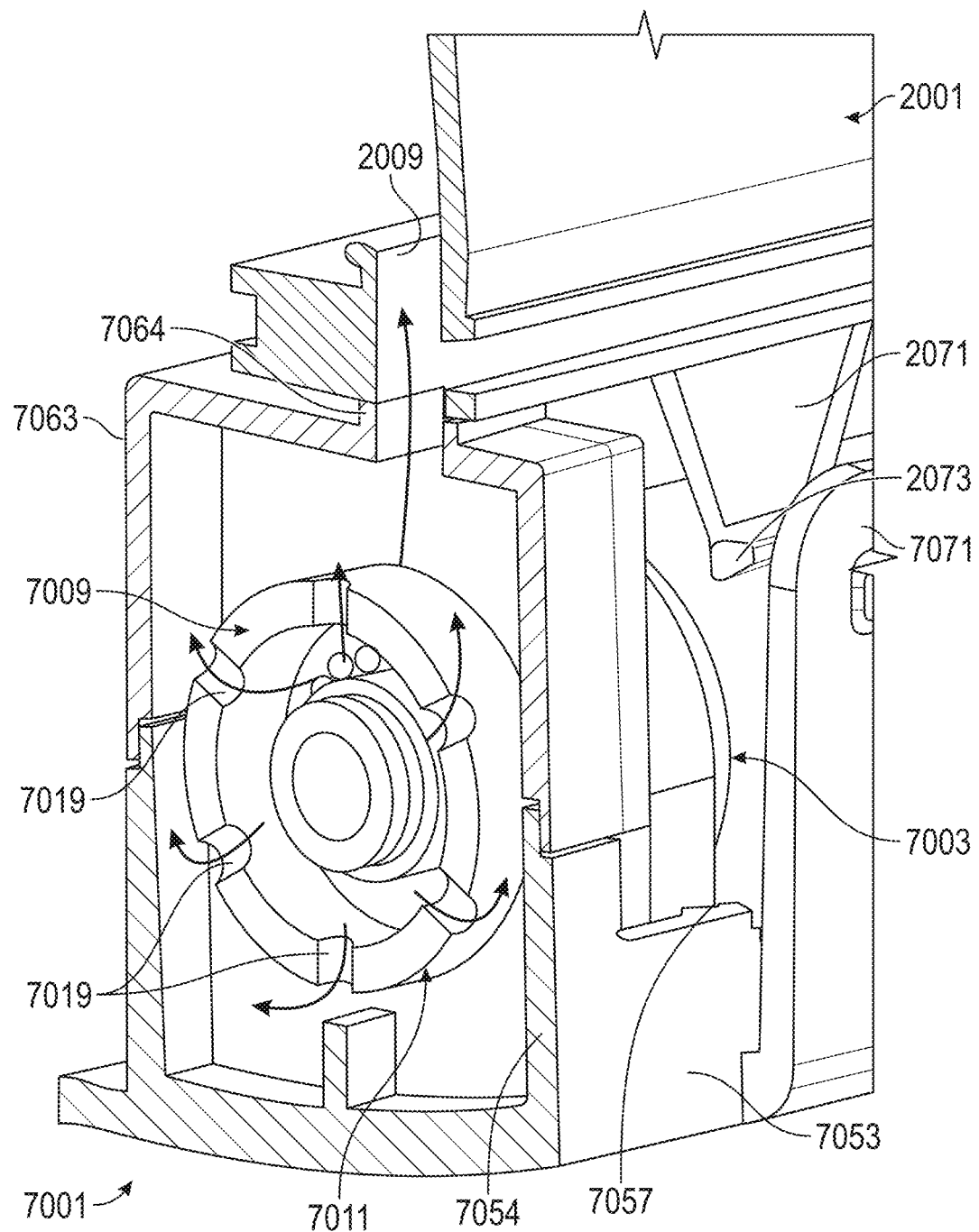
FIG. 29 is a cutaway view showing the valve manifold gases outlets and flow duct to direct gas flow from the gases outlets of the fourth configuration valve module to the second configuration filter module.
Figure 30:
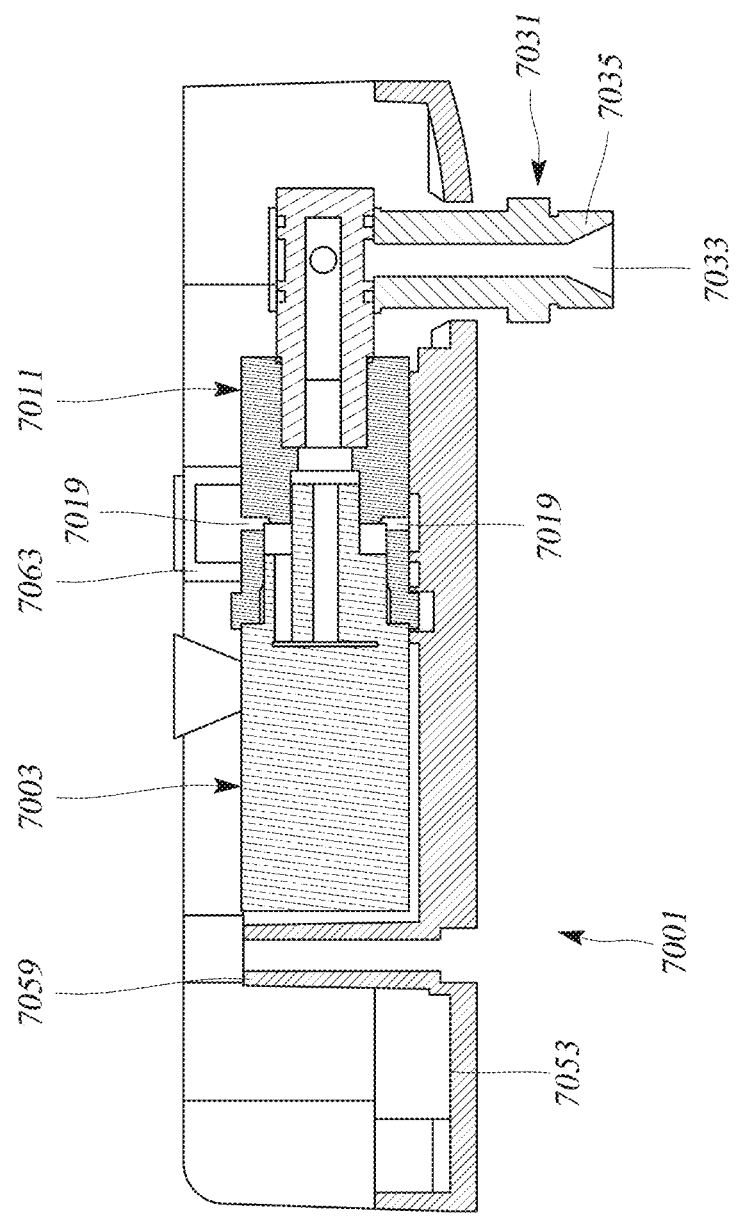
FIG. 30 is sectional view showing the coupling of the valve and valve manifold of the fourth configuration valve module.

The filter module 2001 of the second configuration is suitable for use with a valve module 7001 such as that shown in FIGS. 28 to 30 that has an oxygen hood/duct 7063 which, in use, is in fluid communication with the gases inlet 2045. The oxygen hood/duct directs substantially all oxygen or other gases from the valve manifold outlet(s) 7019 of the valve module 7001 directly into the second sub-compartment, thereby reducing or preventing the loss of oxygen and enhancing entrainment efficiency.

The walk 2043 of the second sub-compartment provide a barrier to direct all oxygen or other gases from the oxygen hood/duct 7063 through the filter medium 2051.

The features, functioning, and options for the second sub-compartment 2041 may be the same as the first sub-compartment 1007, 2007.

Air and oxygen are entrained together after passing through the filter medium 2051, which spans the main compartment 2005, first sub-compartment 2007, and second sub-compartment 2041.

Without the second sub-compartment, it would be possible for some portion of oxygen from the valve module 7001 to pass into the main filter compartment 2005, deflect off the top and side walls of the main filter compartment 2005, recirculate back down toward and out the inlets (against the flow of incoming air), without passing through the filter medium 2051. With the configuration shown, once oxygen has passed from the second sub-compartment through the filter medium 2051, it may then only escape the system if it was to pass back through the filter medium 2051 (against the flow of gases passing through the filter medium) and out the gases inlets.

Therefore, the second sub-compartment substantially enhances the retention and subsequent entrainment of oxygen in the system by directing all oxygen from the oxygen hood/duct 7063 through the filter medium 2051. The second sub-compartment therefore enhances the reliability and consistency of the oxygen entrainment.

The slope/angle/taper of the rear wall of the second sub-compartment may be coincident with that of the rear wall 2021 of the main compartment 2051. Alternatively, the rear wall of the second sub-compartment may be parallel with the filter medium.

Figure 38:
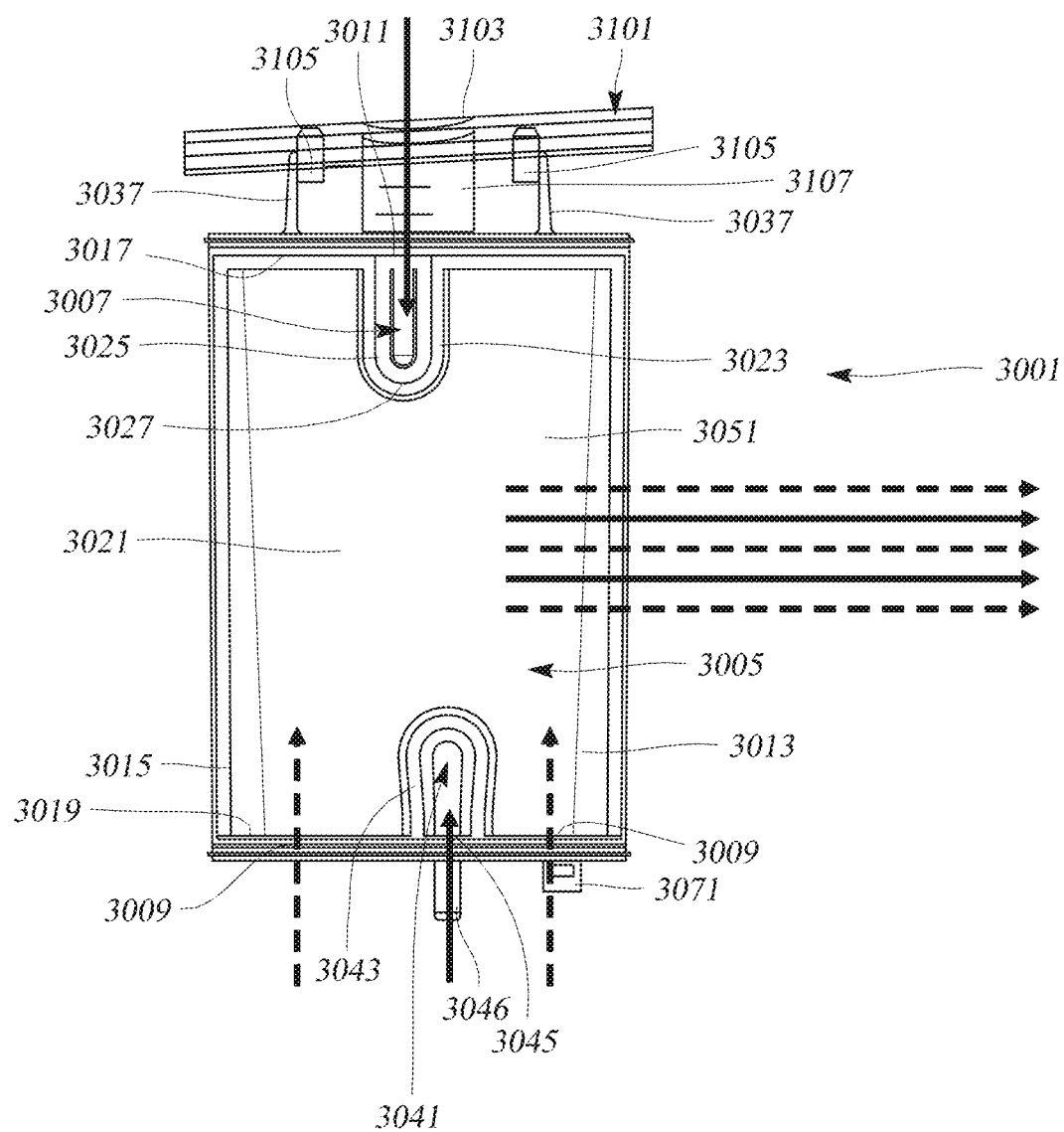
FIG. 38 is a side view showing gas flow paths through the third configuration filter module, with the solid line arrows representing the flow of oxygen (or another gas), and the dashed line arrows representing the flow of ambient air.
Figure 39:
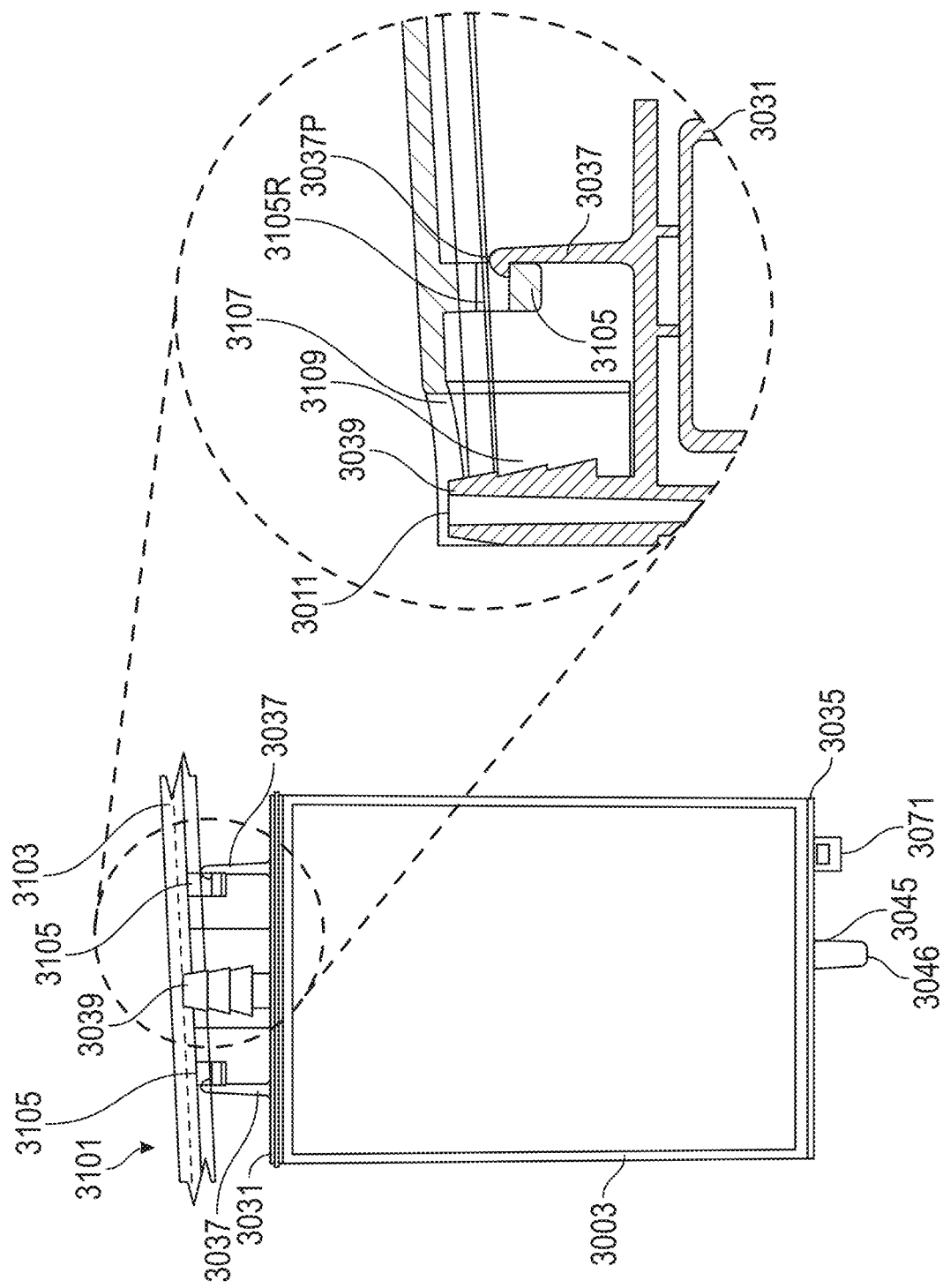
FIG. 39 is a side view showing engagement details of the third configuration filter module.
Figure 40:
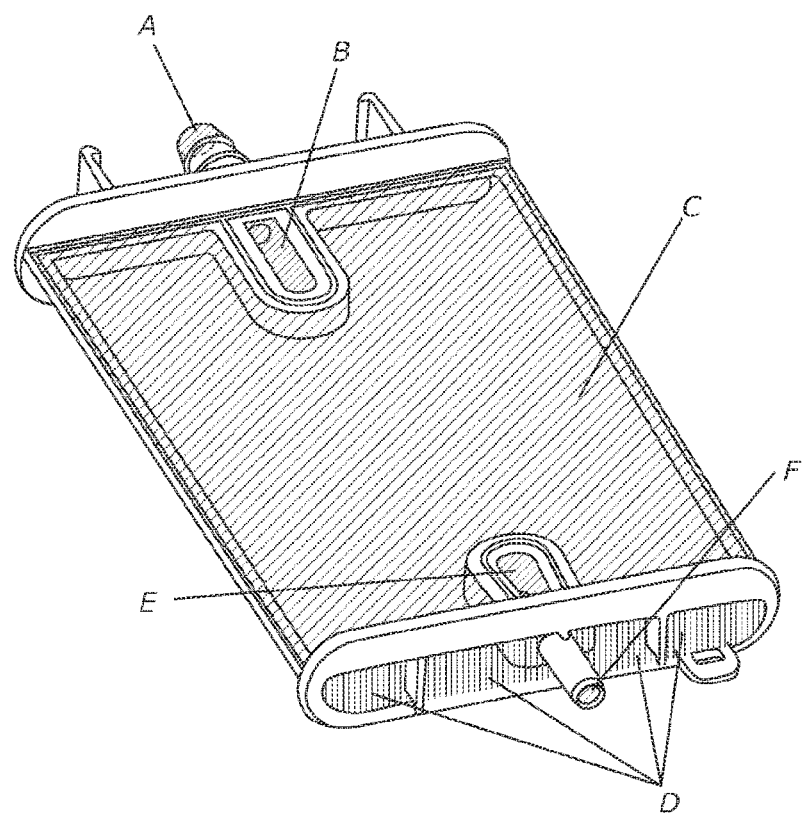
FIG. 40 is a perspective view showing exemplary areas of gases inlets and gases outlets of the third configuration filter module.

FIGS. 38 to 40 show a third configuration filter module 3001. Unless described below, the features, functionality, options, and advantages are all as outlined above for the second configuration, and like reference numerals indicate like parts with 1000 added to each numeral.

The third configuration filter module 3001 includes all the features of the second configuration 2001, including a second sub-compartment 3041 located within the main filter compartment 3005. The second sub-compartment is in fluid communication with a filter extension duct 3046 that extends from the base of the filter body 3003. The duct 3046 may be integrally formed with the filter body 3003 or is separately formed from the filter body 3003. The duct 3046 defines the second sub-compartment gases inlet 3045.

The third configuration filter module 3001 is suitable for use with a valve module 9001 configured to sealingly and fluidly engage the filter extension duct 3046, such as that shown in FIGS. 33 to 37D for example. The filter extension duct 3046 receives all oxygen or other gas from the valve manifold gases outlet 9019, to which it is sealingly engaged. In this configuration, the sub-compartment 3041 is sized relative to the main filter compartment 3005 to maximise the area for the ambient air to pass through filter. As the valve module 9001 sealingly and fluidly engages the filter extension duct 3046, the area of the sub-compartment 3041 can be smaller than if the valve module was not sealingly engaged with the filter extension duct.

The walls 3043 of the second sub-compartment 3041 provide a barrier to direct all oxygen from the filter extension duct 3046 through the filter medium 3051. Air and oxygen is entrained together after passing through the filter medium.

Without the second sub-compartment 3041, it would be possible for some portion of oxygen from the valve module 9001 to pass into the main filter compartment, deflect off the top and side walls of the main filter compartment, recirculate back down toward and out the inlets (against the flow of incoming air), without passing through the filter medium 3051.

With the configuration shown, once oxygen has passed from the second sub-compartment 3041 through the filter medium 3051, it may then only escape the system if it was to pass back through the filter medium (against the flow of gases passing through the filter medium) and out the inlets.

Therefore, the second sub-compartment 3041 substantially enhances the retention and subsequent entrainment of oxygen in the system by directing all oxygen received via the filter extension duct through the filter medium 3051. The second sub-compartment therefore further enhances the reliability and consistency of the oxygen entrainment.

The slope/angle/taper of the rear wall of the second sub-compartment 3041 may be coincident with that of the rear wall 3021 of the main compartment 3005. Alternatively, the rear wall of the third compartment may be parallel with the filter medium.

This configuration also differs in that the snap-fit connectors 3105, 3037 provide a non-permanent attachment of the filter body 3003 to the filter top panel 3101. In this configuration the snap-fit connectors 3037 comprise resilient upstands with inwardly-directed projections 3037P, and the projections are configured to be received in complementary recesses 3105R. The engagement between the snap-fit connectors 3105, 3037 will be adequate to allow the filter module 3001 to be removed from the filter receptacle 300 by lifting via the top panel 3101. However, when the filter module is not engaged with the filter receptacle 300, the upstands can be flexed to disconnect the filter body 3003 from the filter top panel 3101, so the filter body can be replaced without requiring replacement of the filter top panel.

FIG. 46 shows a filter body 11003 of a fourth configuration filter module. The other components of the fourth configuration filter module are not shown in the drawings, but include all the features of the third configuration. The filter body 11003 of the fourth configuration filter module includes all the features of the filter body 3003 of the third configuration filter module 3001, including a second sub-compartment 11041 located within the main filter compartment 11005.

In this configuration, at least a portion of the first sub-compartment 11007 tapers inwardly such that a portion of the first sub-compartment 11007 spaced further from the first sub-compartment gases inlet 1111 has a smaller dimension than a portion of the first sub-compartment 11007 adjacent the first sub-compartment gases inlet 1111. With reference to FIG. 46, a depth of the first sub-compartment 11007 spaced further from the first sub-compartment gases inlet 1111 is shallower than a portion of the first sub-compartment 11007 adjacent the first sub-compartment gases inlet 1111. At least a portion of the second sub-compartment 11041 tapers inwardly such that a portion of the second sub-compartment 11041 spaced further from the second sub-compartment gases inlet 11045 has a smaller dimension than a portion of the second sub-compartment 11041 adjacent the second sub-compartment gases inlet 11045. With reference to FIG. 46, the depth of the second sub-compartment 11041 spaced further from the second sub-compartment gases inlet 11045 is shallower than a depth of the second sub-compartment 11041 adjacent the second sub-compartment gases inlet 11045. These tapers decrease the pressure drop and noise of the gas (for example, oxygen) as it flows through the sub-compartments 11007, 11041.

In this configuration, the snap-fit connectors 11037 provide a non-permanent attachment of the filter body 11001 to the filter top panel. In this configuration the snap-fit connectors 11037 comprise resilient upstands with outwardly-directed projections 11037P, and the projections are configured to be received in complementary recesses. The engagement of the snap-fit connectors 10037 will be adequate to allow the filter module 11001 to be removed from the filter receptacle 300 by lifting via the top panel, in a similar manner to the third configuration of the filter module.

Adjacent each snap-fit connectors 11037 is a spacer 11037S. The spacers 11037S ensure the position of the filter is correct so that the filter is not squeezed over to one side with the seal being broken or leaking on the other side.

The rear wall 11021 of the filter body 11003 has a pair of projections 11090 that provide an area for attaching the filter medium to the filter body 11003. The projections are preferably ultrasonic weld features that provide increased surface area for attaching the filter medium 11003. The projections 11090 are positioned generally centrally along the length of the filter body 11003 and are spaced apart from each other across the width of the filter body 11003. The projections 11090 are shaped as a cross. The projections 11090 support the filter medium to help achieve a consistent filter height. The projections 11090 are integrally moulded with the filter body 11003. The projections 11090 may be placed elsewhere on the filter body 11003, there may be only one moulded projection, there may be three or more moulded projections, the moulded projections may have other shapes. Other shapes include circles or rectangles, for example. The projections have been described as providing ultrasonic weld features. However, the projections may also be used with other attachment mechanisms, such as adhesive.

As described in relation to the first configuration filter module, the fourth configuration filter module may have a seal 11033 comprising a compliant material that is overmoulded onto the upper body portion 11031. In some configurations, the wiper seal 11033 may taper outwardly; i.e., an outward portion of the wiper seal 11033 may be thinner than a more inward portion of the wiper seal. The soft seal seals between the upper body portion 11031 and the wall of the filter receptacle 300 when the filter body is positioned in the filter receptacle 300, to provide sealing engagement between the filter and the filter receptacle and to inhibit bacteria entry into the filter.

A lower part of the filter body comprises a transverse lower body portion 11035. An upper side of the transverse lower body portion 11035 provides the wall 11017. An annular recess 11036 is provided around the periphery of the lower body portion 11035 and is arranged to receive a soft seal such as an O-ring seal or 'wiper' seal. The wiper seal may be integrally formed with the lower body portion 11035. For example, the lower wiper seal may be formed as an outwardly projecting flange of the body portion material of the filter. The thin material allows sufficient flexibility to form the wiper seal. As another example, the lower body portion 11035 may comprise a compliant material that is overmoulded onto the remainder of the filter body, and that comprises the seal. As another example, the seal may comprise a compliant material that is overmoulded onto the lower body portion 11035. In some configurations, the lower wiper seal may taper outwardly; i.e., an outward portion of the lower wiper seal may be thinner than a more inward portion of the wiper seal. The soft seal seals between the lower body portion 11035 and the wall of the filter receptacle 300 when the filter body is positioned in the filter receptacle 300, to provide sealing engagement between the filter and the filter receptacle and to inhibit bacteria entry into the filter.

The following outlines exemplary areas of gases inlets and gases outlets of the third configuration filter module 3001, with reference to FIG. 40.

In some configurations, a ratio of the area A of the first sub-compartment 3007 gases inlet 3011 to the area B of the first sub-compartment gases outlet may be between about 1:5 and about 1:80, may be between about 1:10 and about 1:40, and may be about 1:20. For example, area A may be 15 square millimetres and area B may be 75 square millimetres, or area A may be 4 square millimetres and area B may be 320 square millimetres, or area A may be 7 square millimetres and area B may be 140 square millimetres.

In some configurations, a ratio of the area D of the main compartment 3005 gases inlet 3009 to the area C of the main compartment 3005 gases outlet may be between about 1:10 and about 1:40, may be between about 1:15 to about 1:30, may be between about 1:20 and about 1:25, and may be about 1:22.7. For example, area D may be 400 square millimetres and area C may be 4000 square millimetres, or area D may be 150 square millimetres and area C may be 6000 square millimetres, or area D may be 220 square millimetres and area C may be 5000 square millimetres.

In some configurations, a ratio of the area F of the second sub-compartment 3041 gases inlet 3045 to the area E of the second sub-compartment 3041 gases outlet may be between about 1:5 and about 1:80, may be between about 1:10 and about 1:40, may be between about 1:20 and about 1:25, and may be about 1:23.3. For example, area F may be 12 square millimetres and area B may be 60 square millimetres, or area F may be 3 square millimetres and area E may be 240 square millimetres, or area F may be 4.5 square millimetres and area E may be 105 square millimetres.

While these exemplary areas and ratios are described with reference to the third configuration filter module 3001, they are also applicable to the other configuration filter modules described herein. By providing filters 1001, 2001, 3001, 11001 with relatively large gases outlets and relatively small gases inlets, pressure drop across the filter(s) is minimised.

In some configurations, the filter may be a double-sided filter, with opposed gases outlets on opposite sides of the filter body. Filter medium(s) may be provided on two opposing faces of the filter to filter gases exiting the two opposed gases outlets from the compartments/sub-compartments. Air and/or gases may exit the filter body on the opposing sides/of the filter module. This may further reduce pressure loss and increase the filter life due to the increased filter surface area. In some configurations, the ratios may be double those described above.

In the configurations shown, a 'sheet' of filter medium is provided on a face of the filter body. Alternatively, the filter medium may be pleated to provide additional filter medium surface area.

In the form shown, a main compartment and a second compartment are provided in the filter body. A function of the second compartment is to prevent oxygen from the alternative oxygen supply inlet from passing out the inlets in the bottom of the main compartment of the filter body. The compartments also function to dampen noise generated by turbulence (i.e. as gases pass through the valve manifold or filter module inlets etc) by directing the gases through the filter medium.

Alternatively, a non-closed compartment, baffle(s), barriers, channels, or the like, may be employed within the main compartment to redirect or recirculate incoming oxygen from the alternative supply inlet to a similar effect.

The described filters 1001, 2001, 3001, 11001 are able to filter gases from multiple sources, which avoids the use of multiple filters for different sources. Filter configurations having gases inlet ports located in different parts of the filter (e.g. the top and bottom of the filter body) provide particular versatility by enabling coupling of gases sources from above and below the apparatus housing.

4. Valve Module

FIGS. 2A, 2B, 3B, 4, 6, 10, and 17 to 22 show a first configuration valve module 4001. The valve module 4001 controls the flow of oxygen and/or other gases entering the gas flow path of the apparatus 10, and enables the apparatus 10 to regulate the proportion of oxygen entrained in the airflow. The valve module is formed as a modular unit for ease of manufacture, assembly, servicing, or replacement, for example in the event of malfunction, routine maintenance, or future upgrade/improvement.

The valve module 4001 inserts vertically in an upward direction into the valve module receptacle 306 in the lower chassis 202 of the main housing. In alternative configurations, the valve module may be insertable in a different direction into the housing, such as a forward direction, downward direction, rearward direction, or side direction. The valve module 4001 is removably engageable with the main housing of the apparatus, such that the valve module 4001 is substantially received in the housing and is accessible from the exterior of the housing. Part of the valve module 4001 is arranged to be substantially flush with an external wall of the housing when the valve module is removably engaged with the housing.

Because the valve module is modular and is accessible from the exterior of the housing, the valve module can be replaced without significant disassembly of the apparatus 10 and without compromising seals of the housing of the apparatus. Because the valve module 4001 is substantially received within the housing, when the valve module is engaged with the housing it becomes integrated with the housing and does not increase the size or bulk of the housing. Additionally, the components of the valve module such as the valve 4003 and valve manifold 4011 described below are protected in use because they are positioned within the valve carrier 4051 and main housing of the apparatus in use. This configuration significantly reduces the likelihood of damage of the valve module and valve module components if the apparatus 10 is inadvertently knocked or dropped.

The valve module comprises a flow control valve 4003 that is arranged to control a flow of gas through a valve manifold 4011. The valve is arranged to control a flow of gas into part of the apparatus. For example, the valve may be arranged to control a flow of gas to a filter module 1001, 2001, 3001, 11001. Alternatively, the valve 4003 may be arranged to control a flow of gas to another part of the apparatus. The valve module 4001 and filter module 1001, 2001, 3001, 11001 are positioned upstream of the blower 402 and motor and/or sensor module 400. In some embodiments, the valve module 4001 and filter module 1001, 2001, 3001, 11001 are positioned downstream of the blower 402.

The valve 4003 comprises a cylindrical body 4005 and a valve member in the body.

The flow control valve could be a solenoid valve, could be motor-driven, or could be piezo-operated for example.

In a solenoid valve, the valve member is actuated between open and closed positions. The solenoid valve may be a proportional valve. The extent of gas flow through the valve (i.e. due to the size of the valve opening) is relative to the electrical current supplied to the valve.

Alternatively, the solenoid valve may be controlled with a modulated input signal, so that the valve is modulated between open and closed positions.

The valve 4003 could be a needle valve, plunger valve, gate valve, ball valve, butterfly valve, globe valve, etc. The valve may be of the pressure compensated type.

In some configurations, the valve is a normally-closed valve; that is, the valve is closed when powered off. That will prevent a connected gas supply line continuously releasing oxygen or other gas when the apparatus is powered off. In some alternative configurations, the valve is a normally-open valve.

In some configurations, the valve 4003 is an electrically actuated proportional solenoid valve. For example, the valve may be a µProp valve available from Staiger GmbH & Co. KG of Erligheim, Germany, may be an Asco 202 series Preciflow valve available from Emerson/Asco Valves of New Jersey, or may be any other suitable type of valve.

The valve may have a coaxial inlet-outlet configuration.

The valve module 4001 comprises a valve manifold 4011 which has a body 4013 defining a gas flow path 4015 between a valve manifold gases inlet 4017 and one or more valve manifold gases outlets 4019. The gases inlet 4017 of the valve manifold is axially located at or toward an end of the valve manifold. In some configurations the valve manifold 4011 has a single gases outlet 4019, which is radially located on the valve manifold. In some configurations, the valve manifold 4011 comprises a plurality of valve manifold gases outlets 4019 that are radially located about the valve manifold. The valve manifold outlets 4019 are arranged to deliver gases from the valve manifold gases inlet 4017 to a gases inlet of the filter module 1001, 2001, 3001, 11001. The radial arrangement of outlet(s) 4019 assists with directing oxygen (or other gas) towards the filter module, minimising loss of oxygen and enhancing entrainment efficiency. The valve 4003 is arranged to control a flow of gas from the valve manifold gases inlet 4017 to the valve manifold gases outlet(s) 4019. When the valve is 'closed', gas flow from the gases inlet 4017 to the gases outlet(s) 4019 is prevented. When the valve is 'open', gas flow from the gases inlet 4017 to the gases outlet(s) 4019 is enabled.

An end 4018 of the valve manifold 4011 opposite to the gases inlet receives and sealingly engages with the valve 4003 such that the valve and valve manifold are in fluid communication. Referring to FIG. 20, the end 4018 comprises a flange 4023 to mount to the valve. The flange 4023 has apertures 4023A to receive fasteners 4023F to fasten the manifold to the valve 4003. O-ring(s) may be provided about the periphery of the interface between the valve 4003 and the valve manifold 4011 to sealingly engage the valve with the valve manifold.

The valve manifold 4011 has a shape that is complementary to the shape of the valve 4003. In some configurations, the valve manifold 4011 has a substantially cylindrical body, and the valve 4003 has a substantially cylindrical body. Alternatively, the valve manifold and valve may have different shapes, such as block, square, rectangular, or non-cylindrical. The configuration shown is lighter and cheaper to manufacture than a heavy block manifold. For example, the substantially cylindrical manifold body may be formed from a continuous cylindrical rod that is fed into an automatic production machine. The valve manifold may be made using any suitable technique, such as CNC lathe or mill production for example.

The valve manifold 4011 directs/disperses oxygen from the valve via radially located gases outlets 4019. In some embodiments, a single gases outlet 4019 is provided in the valve manifold. As oxygen passes through the outlet(s), noise is generated. Because the apparatus may be used in medical and/or home environments in close proximity to the patient, it is desirable to minimise the noise produced.

Figure 21:
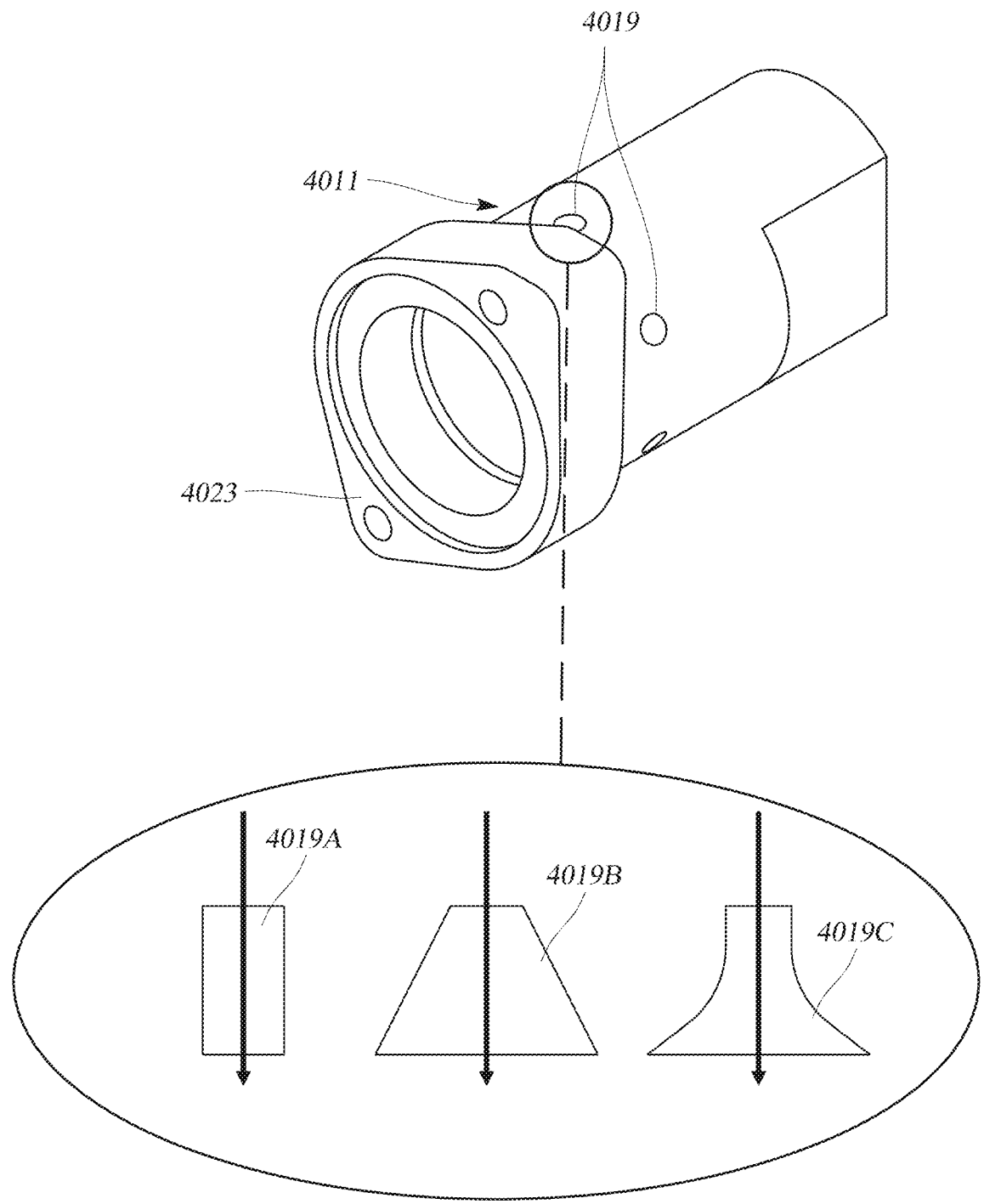
FIG. 21 shows exemplary aeroacoustic shapes for the valve manifold gases outlets.
Figure 22:
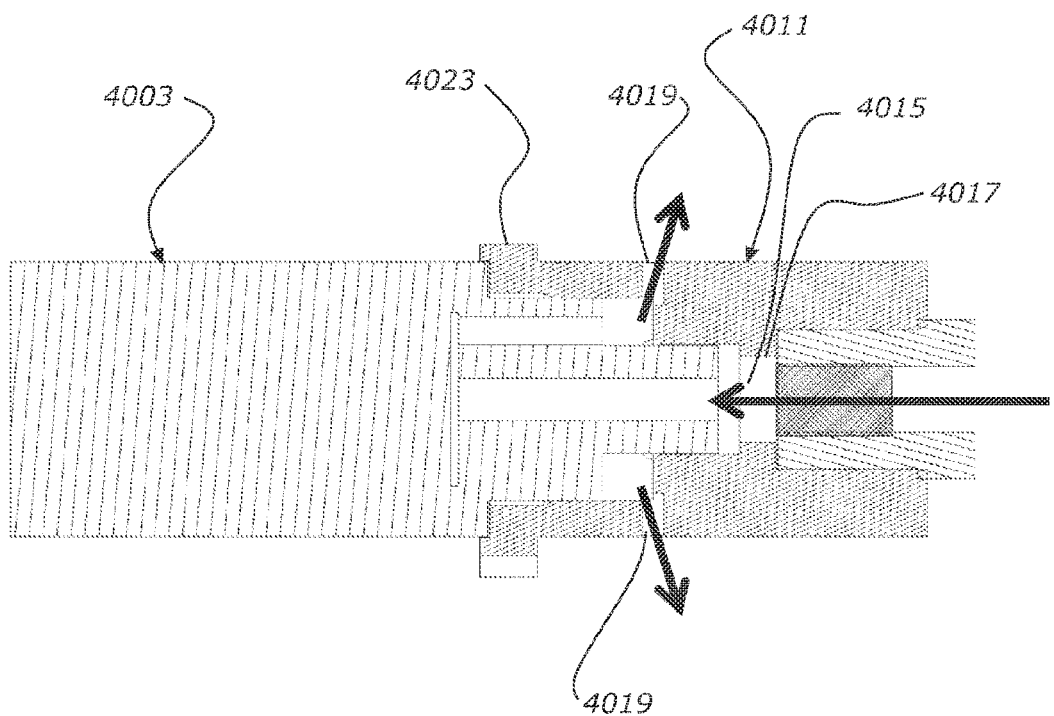
FIG. 22 is a sectional view showing the coupling of, and gas flow path through, the valve and valve manifold of the first configuration valve module.
Figure 23:
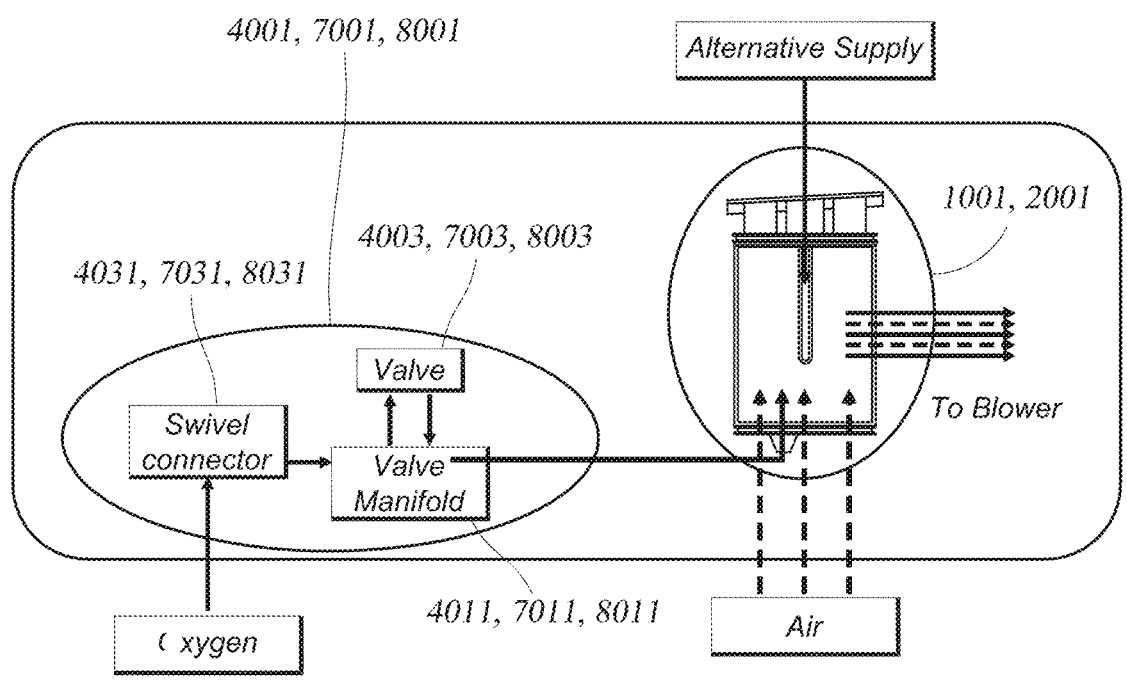
FIG. 23 is a schematic gas flow path diagram for the first, fourth, and fifth configuration valve modules and the first and second configuration filter modules, with the solid line arrows representing the flow of oxygen (or another gas), and the dashed line arrows representing the flow of ambient air.

Sound frequency and volume depend on the shape and number of oxygen outlets and the relationship therebetween. The radial valve manifold gases outlet(s) 4019 may be aeroacoustically shaped to reduce noise. For example, as shown in FIG. 21, the valve manifold gases outlet(s) may be one or, or a combination of, cylindrical through-holes 4019A, frustoconical 4019B, or flared 4019C in shape. The frustoconical and flared shapes may be such that the cross-sections enlarge in the direction of gas flow through the outlet(s) 4019.

Additionally, or alternatively, a hood, duct, or channel may be formed around, in proximity to, or in fluid communication with the valve manifold outlet(s) 4019 in order to reduce noise. Additionally and/or alternatively, foam, or the like, may be placed around the valve manifold, in proximity to the valve manifold outlets, to reduce noise.

A small filter may be provided inside the valve manifold gases inlet 4017 inlet to prevent the introduction of dust or particulates into the valve.

An end of the valve manifold corresponding to the gases inlet 4015 is arranged to receive and connect to a connector 4031. In the form shown, the connector 4031 is a swivel connector. Alternatively, the connector 4031 may be arranged such that a gases inlet 4033 of the connector can move in a different way, such as a translational movement or pivoting movement for example.

The valve manifold and swivel connector may be threaded to engage the components together. The swivel connector 4031 has a gases inlet 4033 that is oriented substantially transversely relative to a longitudinal axis LA of the valve manifold, and that is in fluid communication, by a gas flow path 4037, with a swivel connector gases outlet 4039. The gases inlet 4033 of the swivel connector is formed in a transversely extending conduit/coupling 4035 that is fluidly connectable to a gas supply line. For example, the conduit/coupling 4035 may connect to a gas supply line connector to deliver gases such as oxygen to the valve manifold. The gas supply line connector can be chosen depending on the country of use; for example, DISS and NIST medical gas connectors would typically be used in USA and Europe respectively. The swivel connector 4031 is arranged to provide a fluid connection between the gas supply line and the gases inlet 4017 of the valve manifold.

With reference to FIG. 10, the portion of the swivel connector carrying the gases inlet 4033 is arranged to rotate about the portion of the swivel connector carrying the gases outlet 4039, about the longitudinal axis LA of the valve manifold 4011. The swivelling structure is self-contained in the swivelling connector. Suitable bearings, seals, and aperture are provided between the two portions of the swivel connector to enable that rotation to occur.

The gases inlet 4033 of the swivel connector may be oriented substantially perpendicularly relative to the longitudinal axis LA of the valve manifold as shown. Alternatively, the gases inlet 4033 could be oriented at a different substantially transverse angle relative to the longitudinal axis LA of the valve manifold.

In some configurations, the gases inlet of the swivel connector is rotatable through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

In some configurations, the gases inlet 4033 that is fluidly connectable to the gas supply line is movable between a substantially horizontal position and a substantially vertical position, relative to the housing. In some configurations, the substantially horizontal position is a side, forward, or rearward position. In some configurations, the substantially vertical position is an upward or downward position. In some configurations, the substantially horizontal position is a side position and the substantially vertical position is a downward position.

Figure 2B:
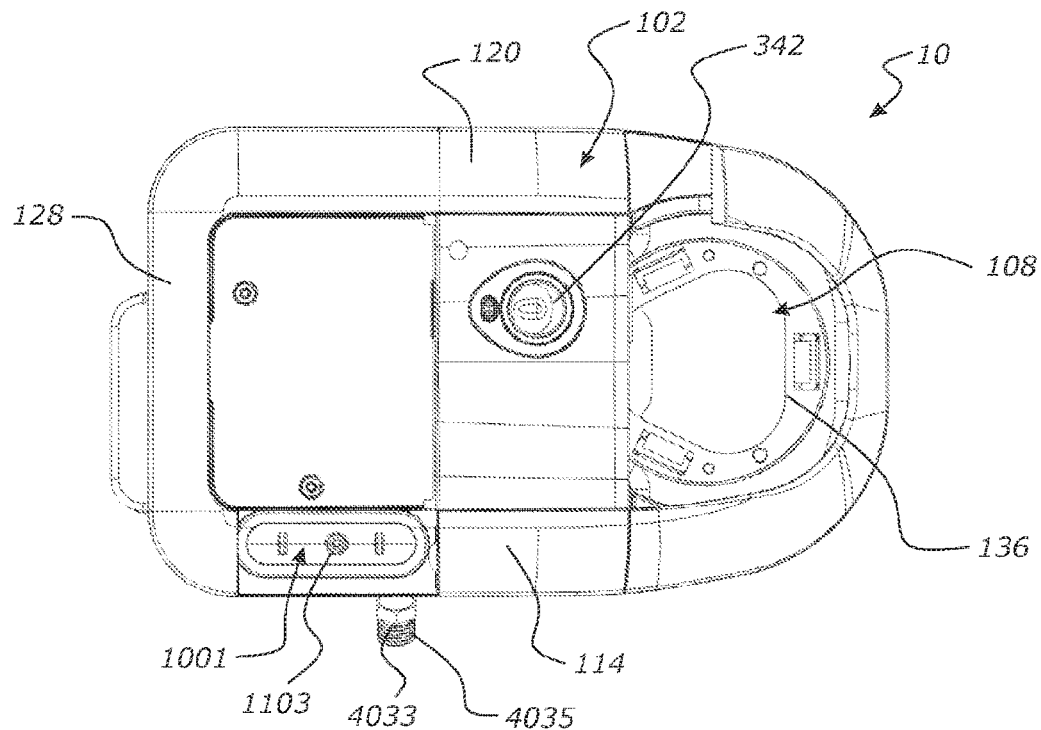
FIG. 2B is a top view of the flow therapy apparatus showing an exemplary location of the valve module and the filter module.

As shown in FIGS. 2A, 2B, and 4 for example, when the valve module 4001 is mounted in the lower chassis 202, the conduit/coupling 4035 may project from the side or bottom of the lower chassis 202, or anywhere therebetween. The swivel connector 4031 allows for easier positioning of the gas supply line (i.e. when the apparatus 10 is on a medical stand such that the inlet may be best positioned vertically or on a bench top such that the inlet may be best positioned horizontally). As a result, the swivel connector 4031 may prevent bending of the gas supply line. It will be appreciated that the valve module 4001 could be provided in a different part of the apparatus housing, such as in a top, side, rear, or front of the housing for example.

The swivel connector additionally reduces the force exerted on the apparatus housing by the connected gas supply line. For example, when the apparatus is mounted on a pole, the weight of the hanging tube may place a strain on the apparatus. The swivel connector enables the gas supply line to be directed out of the way and secured to the pole.

Figure 43:
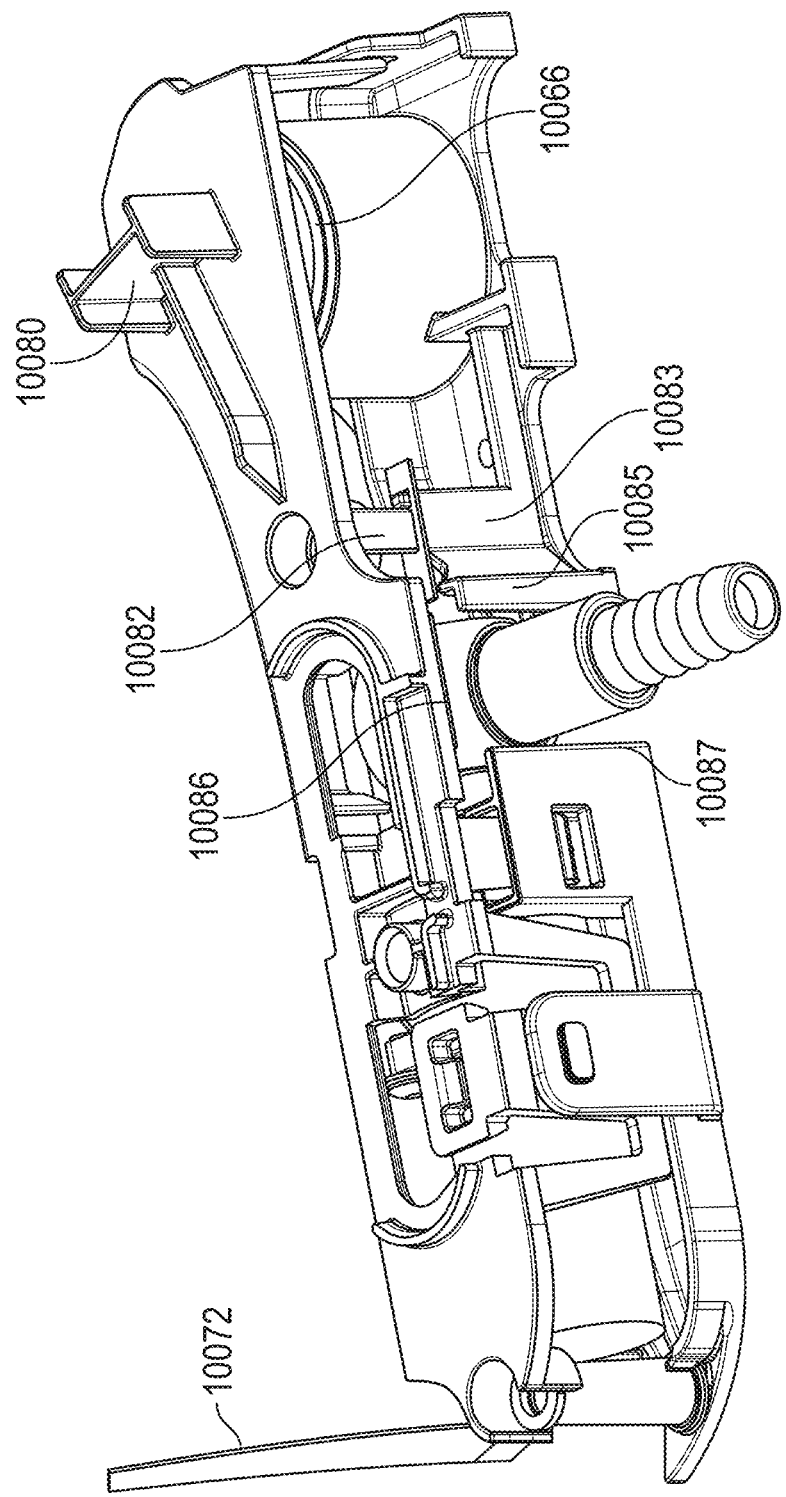
FIG. 43 is a rear side overhead perspective view of the seventh configuration valve module.

In the event of a sudden knock to the coupling 4035 or snag to the gas supply line connected thereto, for example, the swivel connector would most likely rotate before transferring force to the valve module and housing. As a result, the swivel connector assists with avoiding damage to the apparatus. In addition, the valve carrier may have one or more guards 10085, 10086, 10087 to prevent damage to the main apparatus housing. FIG. 43 shows the valve carrier having three guards 10085, 10086, 10087 that extend along the edges of the valve carrier that the swivel might strike, preventing the swivel striking the main apparatus housing. The guards 10085, 10086, 10087 are shown as integral features of the valve carrier parts. Alternatively, the guards 10085, 10086, 10087 may be separate features that are attached to the valve carrier.

In the event of damage to the valve module, the valve module is replaceable without requiring disassembly of the overall apparatus.

The valve module 4001 is located at the start of the flow path of the apparatus. If the valve 4003 was to be obstructed (i.e. by dust, particulate, etc.) such that it would be held open, excess pressurised oxygen or other gas would 'dump' out ambient air entry opening(s) in the valve carrier 4051 (e.g. the opening shown beneath the swivel connector in FIG. 18). This would prevent any excess pressure reaching the patient. As such, the system may be considered inherently pressure limited without the use of a pressure relief valve.

The valve module 4001 comprises a valve carrier 4051 that substantially contains and supports the valve 4003, the valve manifold 4011, and the swivel connector 4031. The valve carrier 4011 is removably engageable with the housing of the apparatus. An exterior part of the valve carrier is arranged to be substantially flush with an external wall of the apparatus housing when the valve module is removably engaged with the housing.

The valve carrier 4051 may be sacrificial, so that in instances of excessive stress, the valve carrier fails before the main apparatus housing.

The valve carrier 4051 comprises a first, lower valve carrier part 4053 and optionally, a second, upper valve carrier part. The valve, valve manifold, and swivel connector are secured in place at least partly between the first valve carrier part 4053 and the second valve carrier part and are fixed relative to the valve carrier (other than the swivelling gases inlet 4033). In an alternative configuration, the first valve carrier part may comprise a first side part and the second valve carrier part may comprise a second side part. In an alternative configuration, the valve, valve manifold, and swivel connector may be coupled to, and in secured in place by, the lower valve carrier part 4053.

The valve carrier 4051 may be retained in the recess of the housing by fasteners, a permanent or temporary snap-fit, or any other suitable way.

The valve carrier comprises supporting structure 4057 to support the valve, valve manifold, and swivel connector. The supporting structure may comprise, one, two, or more supports to support the valve, valve manifold, and swivel connector.

The valve carrier comprises sleeves 4059 to receive fasteners to fasten the first and second valve carrier parts 4053 together and/or to fasten the valve carrier to the main housing of the apparatus. In the form shown in FIGS. 17 and 20, the sleeves also receive flattened surfaces 4021 of the valve manifold 4011 to prevent rotation of the valve manifold 4011 in the valve carrier, which could otherwise be caused by rotation of the swivel connector 4031.

Additional or alternative supporting structure could be provided, such as integrally moulded ribs and/or other features to provide structural support to the valve carrier—particularly against movement of an oxygen or gas line or hose attached to the swivel connector.

Opening(s) 4051O are provided in the valve carrier 4051 to allow ambient air to be drawn in to the gas flow path of the apparatus. The ambient air flow path passes near or adjacent to the valve. In the form shown, the opening 4051O is located around the gases inlet of the swivel connector. Additionally, or alternatively, the opening may be located elsewhere in the valve carrier. When the blower motor 402 of the apparatus is operated, that will create suction through the filter module and valve module, to suck ambient air into the apparatus. The ambient air flow path passes through the valve module and allows ambient air to be entrained with the flow of gas from the flow control valve. The ambient air flow path has a gas outlet adapted to deliver ambient air such that it flows past one or more temperature sensors of the apparatus for delivering a flow of gas.

The apparatus may simultaneously draw in gas from the gases inlet of the valve manifold and ambient air, or the pressurisation of gas from the gases inlet may force that gas through the filter. The gases will exit the valve module and enter the gases inlets in the filter. The apparatus may be configured such that the gas from the gases inlet and the ambient air are dynamically entrained/mixed in the apparatus prior to being delivered to the gases outlet of the apparatus.

The valve module may be configured to minimise pressure drop across the valve module by having one or more of: the large opening 4051O for ambient air located around the swivel connector and/or elsewhere; radiuses/rounded/sloped edges in the flow path (i.e. inside the valve manifold, for example) to minimise turbulence and smooth flow.

This valve module 4001 and the other valve modules 5001, 6001, 7001, 8001, 9001 described herein are arranged to directly couple with the filters 1001, 2001, 3001, 11001 to provide a gas flow path from the valve module to the filter. A hose connection is not required between the valve module and the filter module. This minimises the size of the components and makes it easy to connect and disconnect the modular valve module and filter module.

Figure 24:
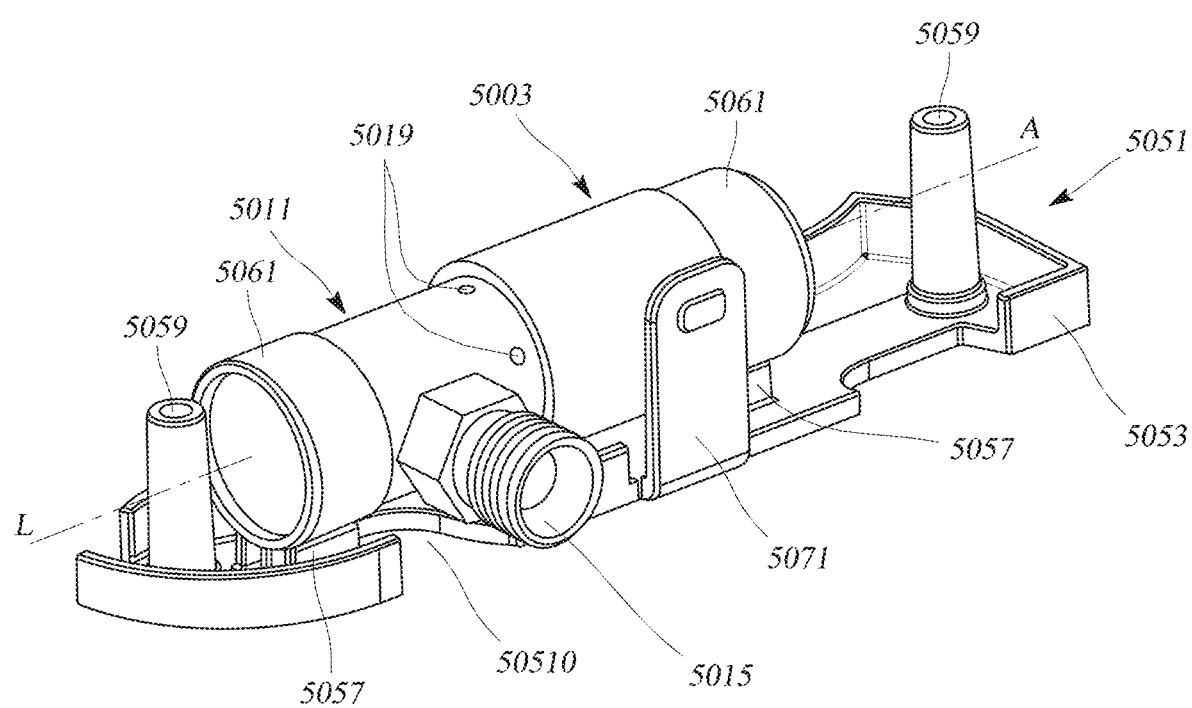
FIG. 24 is a rear side overhead perspective view of a second configuration valve module.
Figure 25:
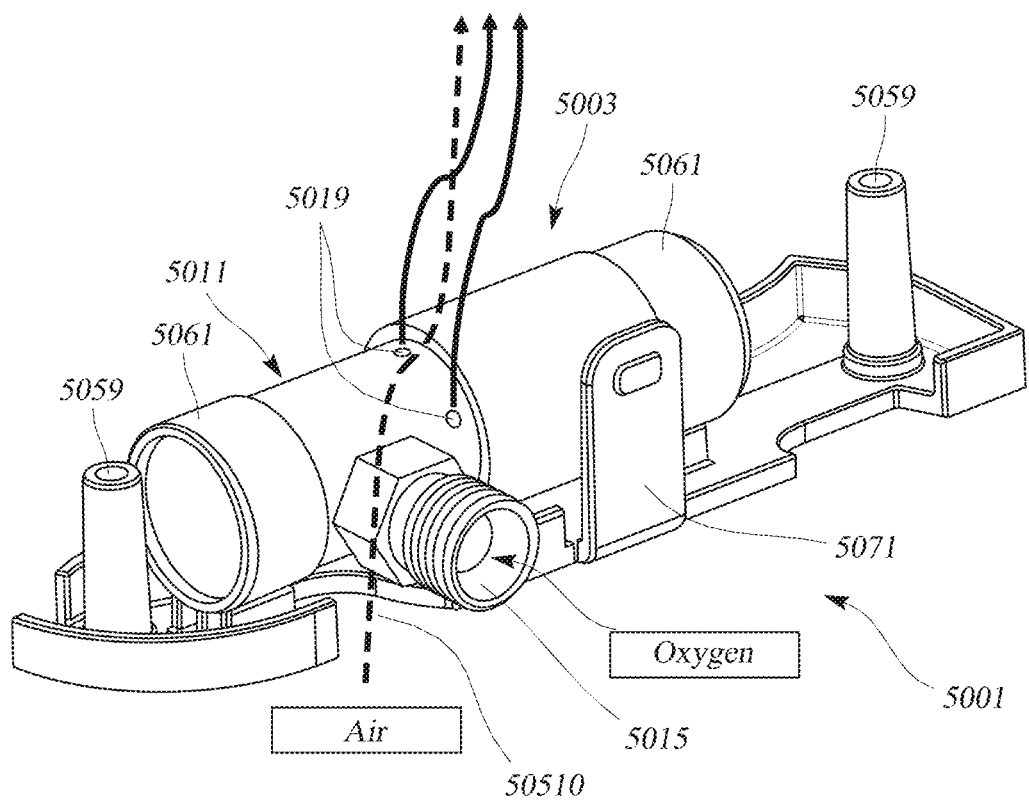
FIG. 25 is a rear side overhead perspective view showing the gas flow paths through the second configuration valve module, with the solid line arrows representing the flow of oxygen (or another gas), and the dashed line arrow representing the flow of ambient air.

FIGS. 24 and 25 show a second configuration valve module 5001. Unless described below, the features, functionality, options, and advantages are all as outlined above for the first valve module configuration above, and like reference numerals indicate like parts with 1000 added to each numeral.

The above first configuration valve module 4001 utilises a fixed valve manifold 4011 with a swivel connector 4031 attached. This second configuration valve module 5001 differs in that the valve manifold 5011 swivels/rotates within the valve carrier 5051, the valve 5003 is rotatable with the valve manifold 5011, and a gas supply line may connect directly to the gases inlet 5015 of the valve manifold. The valve manifold 5011 and valve 5003 are rotatable inside swivel bearings 5061 that are provided between the valve and valve manifold and the valve carrier 5051. Alternatively, the valve manifold 5011 and valve 5003 may be configured to rotate within, and may be supported and/or held in place by, ribs or other integrally moulded support features in the valve carrier 5051.

The valve manifold gases inlet 5015 extends substantially transversely relative to a longitudinal axis of the valve manifold, and is fluidly connectable to a gas supply line, and the valve and valve manifold are rotatable relative to the valve carrier about the longitudinal axis LA of the valve manifold 5011.

The valve manifold gases inlet 5015 may extend in a substantially perpendicular direction relative to the longitudinal axis LA of the valve manifold. In some configurations, the valve manifold gases inlet could be oriented at a different substantially transverse angle relative to the longitudinal axis of the valve manifold.

In some configurations, the valve 5003 and valve manifold 5011 are rotatable relative to the valve carrier through up to about 190 degrees about the longitudinal axis of the valve manifold, or through up to about 180 degrees about the longitudinal axis of the valve manifold, or through up to about 160 degrees about the longitudinal axis of the valve manifold, or through up to about 120 degrees about the longitudinal axis of the valve manifold, or through up to about 90 degrees about the longitudinal axis of the valve manifold, or through up to about 60 degrees about the longitudinal axis of the valve manifold, or through up to about 45 degrees about the longitudinal axis of the valve manifold.

This configuration eliminates the need for a separate swivel connector. As a separate swivel connector is not required, the gas flow path has fewer disturbances—such as at the point at which the separate swivel connector connects to the valve manifold. As a result, the rotating or swivelling valve manifold 5011 provides a simpler flow path inside the valve manifold 5011.

Figure 26:
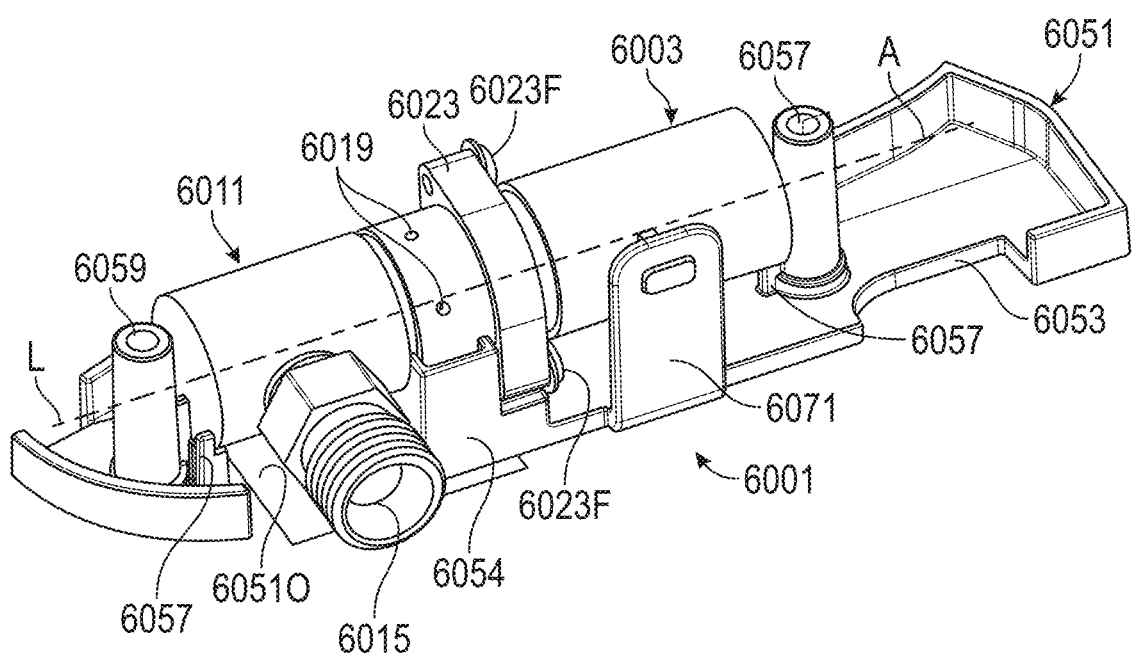
FIG. 26 is a rear side overhead perspective view of a third configuration valve module.
Figure 27:
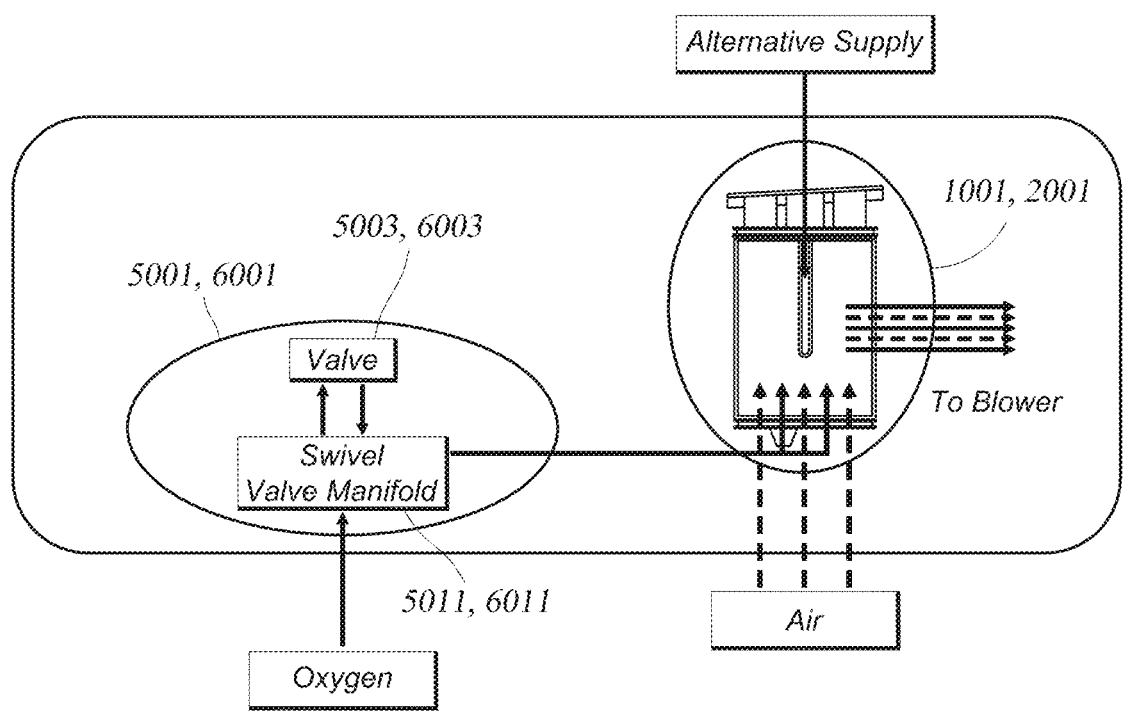
FIG. 27 is a schematic gas flow path diagram for the second and third configuration valve modules and the first and second configuration filter modules, with the solid line arrows representing the flow of oxygen (or another gas), and the dashed line arrows representing the flow of ambient air.

FIG. 26 shows a third configuration valve module 6001. Unless described below, the features, functionality, options, and advantages are all as outlined above for the second valve module configuration above, and like reference numerals indicate like parts with 1000 added to each numeral.

In this configuration, the valve manifold 6011 swivels/rotates within the valve carrier 6051. The valve 6003 is rotatable with the valve manifold 6011. A gas supply line may connect directly to the gases inlet 6015 of the valve manifold. The valve carrier 6051 includes flow channels 6054 adjacent the valve manifold outlets 6019 to direct flow upward toward a flow channel duct, which may be in the form of a housing similar to that shown in the configuration of FIGS. 28 and 29 and described in more detail below.

The valve manifold 6011 is configured to swivel or rotate within, and may be supported and/or held in place by, ribs or other integrally moulded support features in the valve carrier 6051.

This configuration eliminates the need for a separate swivel connector. As a separate swivel connector is not required, the gas flow path has fewer disturbances—a such as at the point at which the separate swivel connector connects to the valve manifold. As a result, the rotating or swivelling manifold provides a simpler flow path inside the valve manifold 6011.

The flow channels that direct oxygen or other gases upward from the manifold gases outlets 6019 upward toward the filter 1001, 2001, 3001, 11001 reduce or prevent the loss of oxygen from the system. As a result, oxygen entrainment efficiency is enhanced.

The flow channels 6054 and flow channel duct are examples of flow guiding structure that can be used in the valve modules described herein. The flow guiding structure is arranged to direct gas flow from the valve manifold gases outlet(s) toward a filter when the valve module is removably engaged with the apparatus housing. In some configurations, the flow guiding structure comprises an annular housing that surrounds a plurality of valve manifold gases outlets, wherein the flow guiding structure comprises a gases outlet that is in fluid communication with a gases inlet of the filter.

FIGS. 28, 29, and 30 show a fourth configuration valve module 7001. Unless described below, the features, functionality, options, and advantages are all as outlined above for the first valve module configuration above, and like reference numerals indicate like parts with 3000 added to each numeral.

In this configuration, the valve manifold 7011 remains fixed stationary, and a gas supply line connects to the valve manifold 7011 via a swivel connector 7031. The valve carrier includes flow guiding structure that is arranged to direct gas flow from the valve manifold gases outlet(s) toward a filter when the valve module is removably engaged with the apparatus housing. In particular, flow channels 7054 adjacent the valve manifold outlets 7019 direct flow upward toward a flow channel oxygen hood duct 7063, to direct oxygen from the flow channels upward toward the filter 2001. The flow channels 7054 are provided in the lower valve carrier part 7053 and the duct 7063 is provided separately from the lower valve carrier part but couples to the flow channels 7054. In some configurations, the duct 7063 could be provided by a housing in an upper carrier part of the valve carrier 7051. The duct 7063 engages with the upper ends of the flow channels 7054. The upper opening of the flow channel duct 7064, in use, abuts or seals against the filter body inlet(s) 2009 to direct substantially all oxygen from the valve module 7001 into the filter module 2001. This aids in preventing loss of oxygen in the system—subsequently enhancing oxygen entrainment efficiency.

In this configuration, oxygen entrainment in the air flow is enhanced by the flow channels 7054 and duct 7063 directing oxygen flow upward toward the filter.

Figure 31:
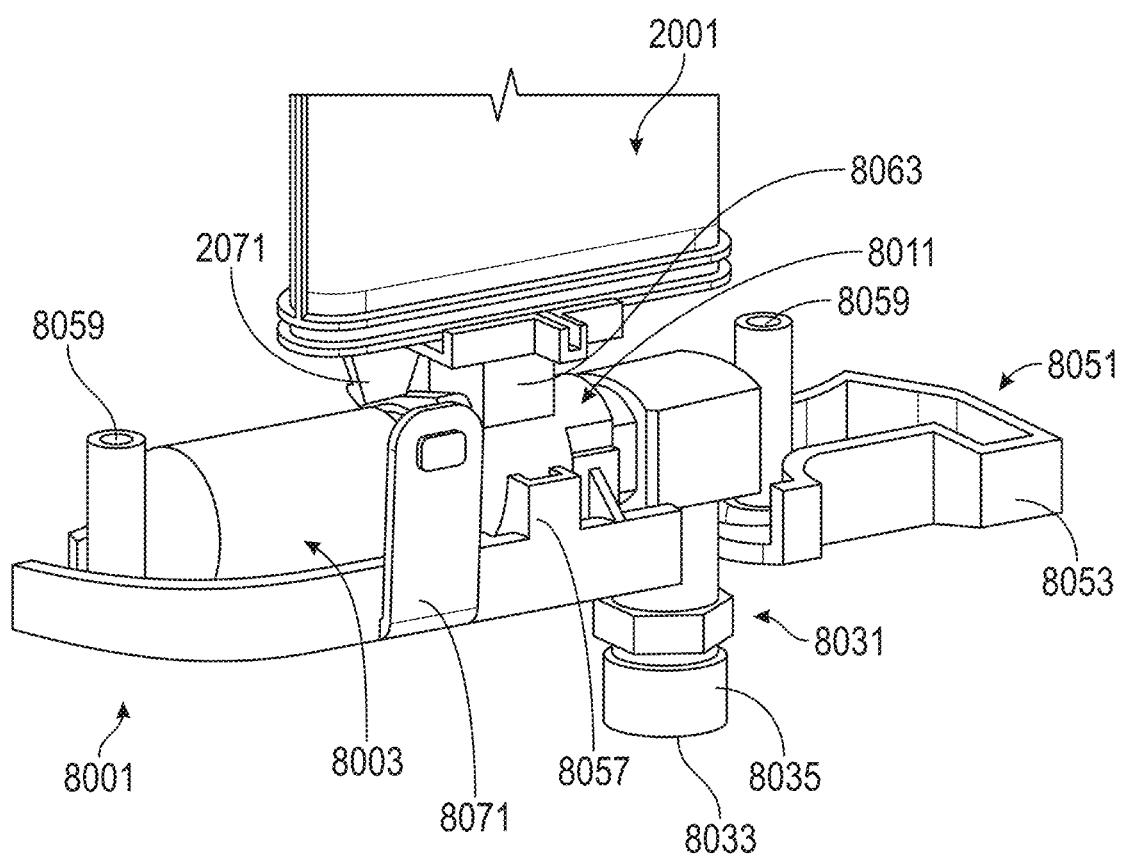
FIG. 31 is a rear side overhead perspective view of a fifth configuration valve module.
Figure 32:
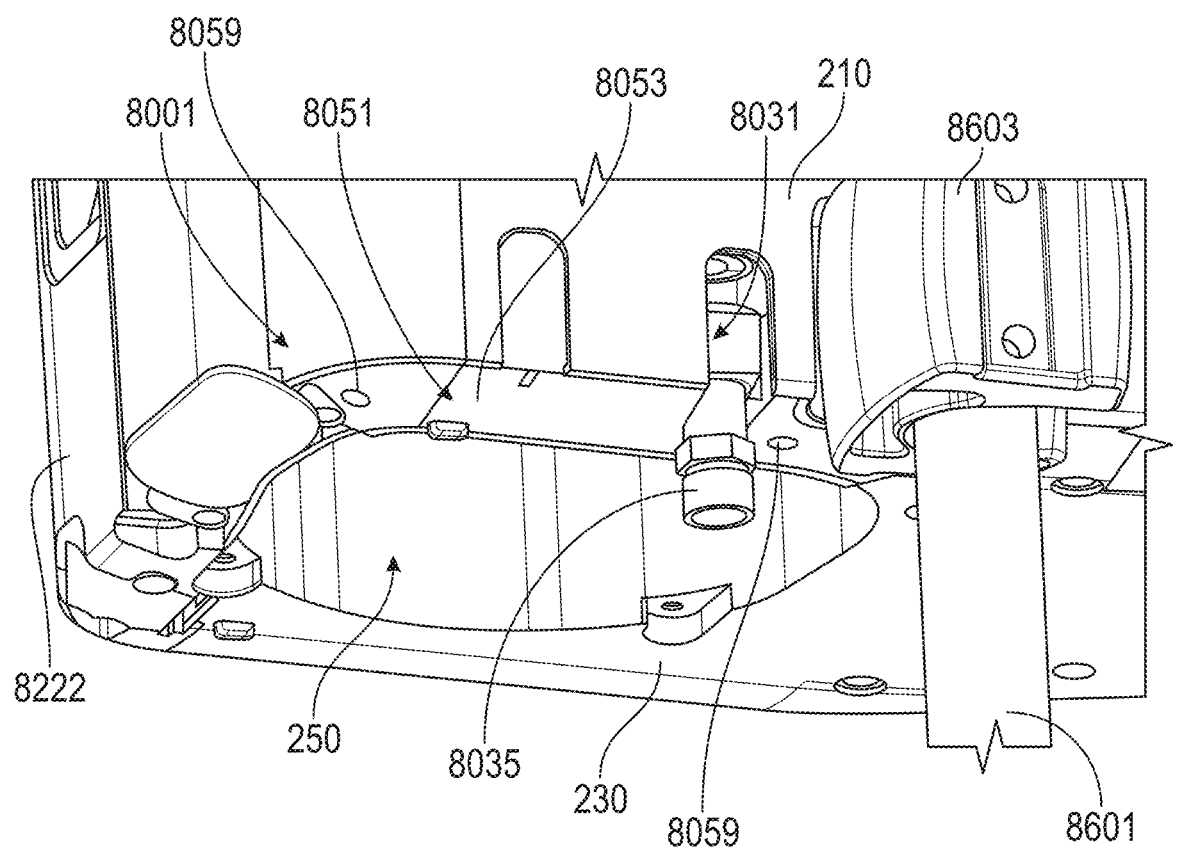
FIG. 32 is an underside perspective view of the fifth configuration valve module in position in the housing of the apparatus for delivering a flow of gas, and showing the apparatus mounted to a pole stand.
Figure 33:
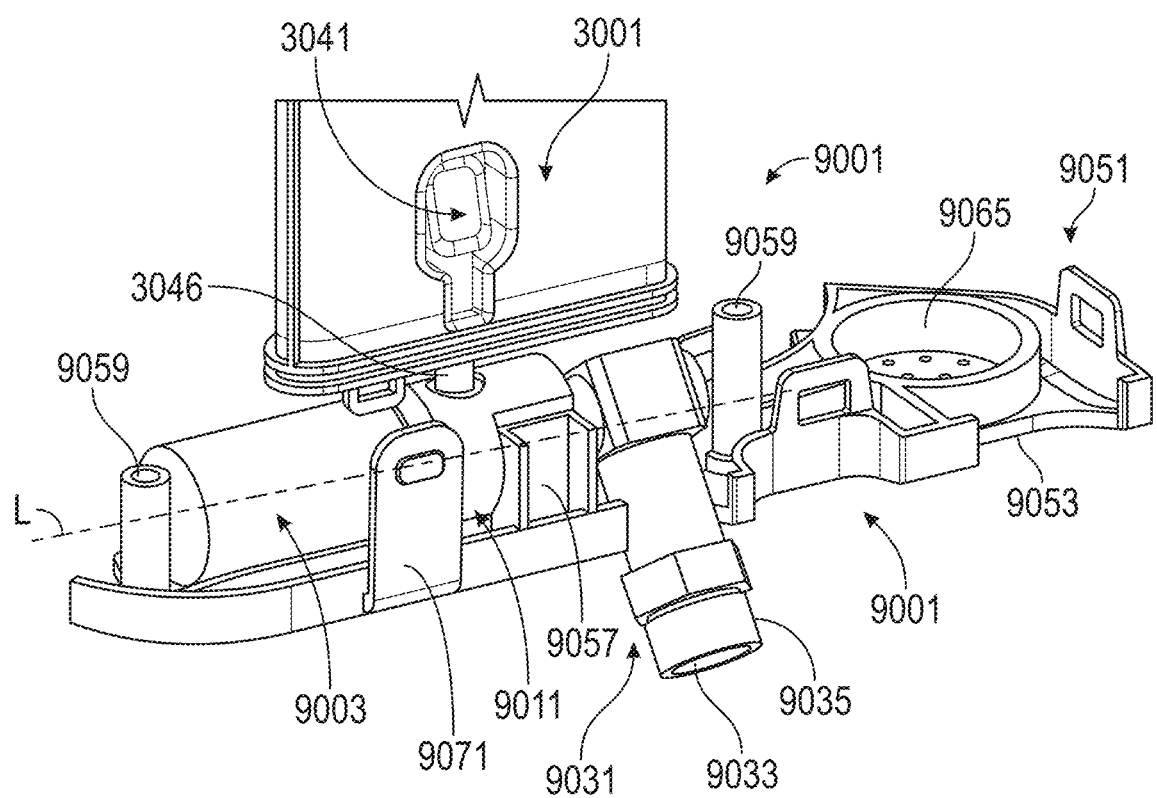
FIG. 33 is a rear side overhead perspective view of part of a sixth configuration valve module and third configuration filter module.

FIG. 31 shows a fifth configuration valve module 8001. Unless described below, the features, functionality, options, and advantages are all as outlined above for the first valve module configuration above, and like reference numerals indicate like parts with 4000 added to each numeral.

In this configuration, the valve manifold 8011 remains stationary in the valve carrier 8051. By comparison with the first, second, third and fourth configurations, the electrically actuated valve 8003, valve manifold 8011, and swivel connector 8031 are reoriented 180°. This is such that, when assembled with the apparatus 10, the swivel connector protrudes from the unit near the point at which the apparatus 10 is mounted to a pole stand 8601 via a mounting 8603 that may be integrally formed with the main housing of the apparatus 10 or separately formed and attached to the main housing.

A gas supply line, such as an oxygen supply line, connects to the valve manifold 8011 via the swivel connector 8031.

The valve manifold 8011 has a single manifold gases outlet. A flow channel duct 8063 directs oxygen from the single manifold outlet upward toward the filter 2001. The upper opening of the flow channel duct, in use, abuts or seals against the filter body inlet(s) 2009 to direct substantially all oxygen from the valve module 8001 into the filter module 2001. This aids in preventing the loss of oxygen from the system—subsequently enhancing oxygen entrainment efficiency.

In this configuration, oxygen entrainment in the air flow is enhanced by the duct 8063 directing oxygen flow upward toward the filter 2001. This provides for more reliable and consistent oxygen entrainment.

Portion 8035 of the swivel connector 8031 protrudes from the housing of the apparatus 10 near the point at which the housing unit is mounted to the pole stand 8501. The position of the swivel connector therefore enables positioning of the gas supply line such that it may run substantially adjacent the pole of the pole mount. This may avoid the gas supply line extending substantially away from the pole stand such that it may catch or drag on nearby objects. This may also avoid kinking of the gas supply line. Having the swivel connector positioned near the pole also allows a user to secure the gas supply line to the pole to provide strain relief.

FIGS. 33 to 36 and 37 show a sixth configuration valve module 9001. Unless described below, the features, functionality, options, and advantages are all as outlined above for the fifth valve module configuration above, and like reference numerals indicate like parts with 1000 added to each numeral.

Like the first, fourth and fifth configurations, the valve manifold 9011 remains stationary in the valve carrier 9051. As with the sixth configuration, portion 9035 the swivel connector protrudes from the apparatus 10 near the point at which the apparatus is mounted to a pole stand.

A gas supply line, such as an oxygen supply line, connects to the valve manifold 9011 via the swivel connector 9031.

The valve manifold has a single manifold gases outlet 9019. The single manifold gases outlet 9019 sealingly receives a filter extension duct 3046, which is integrally formed with the filter module 3001. Substantially all oxygen from the valve assembly will be directed into the filter module. This aids in preventing the loss of oxygen from the system—subsequently enhancing oxygen entrainment efficiency.

Figure 37A:
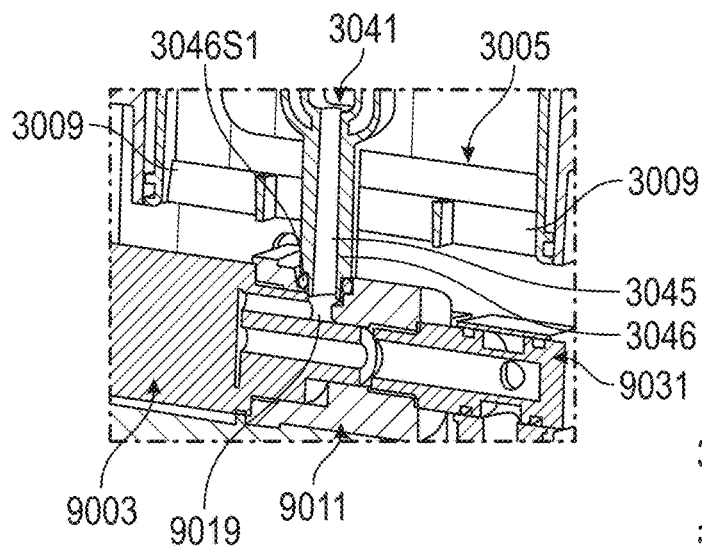
FIGS. 37A-37D show exemplary seals between the valve manifold gases outlet of the sixth configuration valve module and the filter module duct of the third configuration filter module.
Figure 37B:
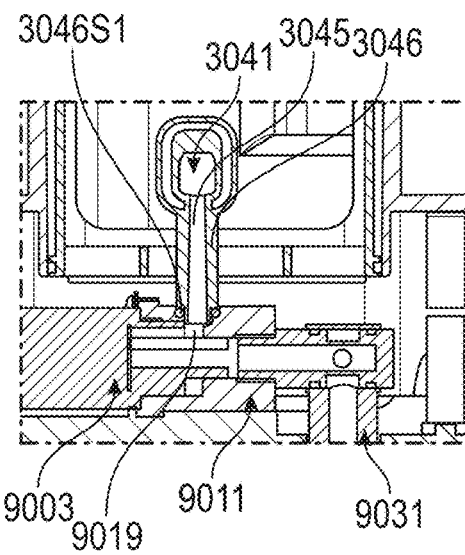
Figure 37C:
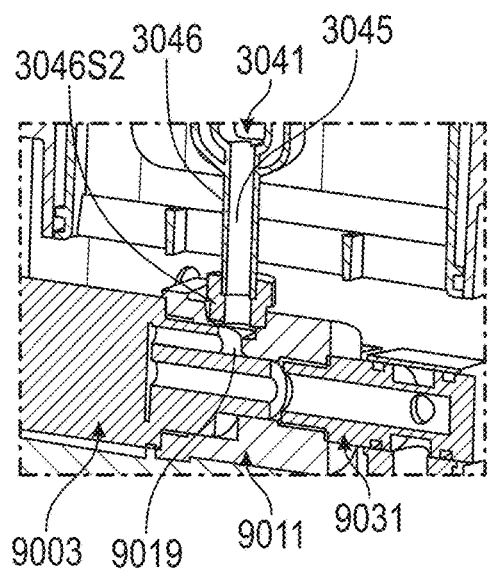
Figure 37D:
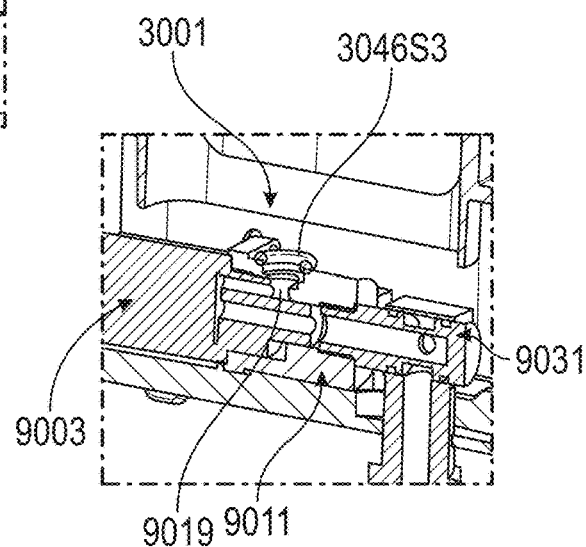

FIGS. 37A to 37D show exemplary seals that may be used to seal between the single manifold gases outlet 9019 and the filter extension duct, such as an O-ring seal 3046S1 (FIGS. 37A and 37B), a grommet seal 3046S2 (FIG. 37C), or a face seal 3046S3 (FIG. 37D).

Figure 47:
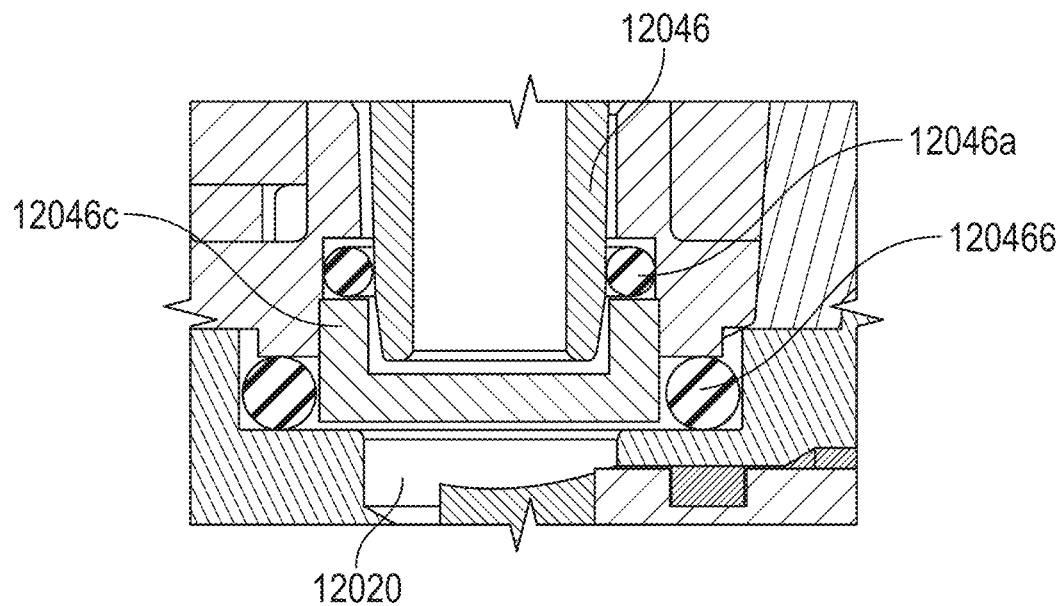
FIG. 47 is a partial sectional view of a filter extension duct and manifold outlet.
Figure 48:
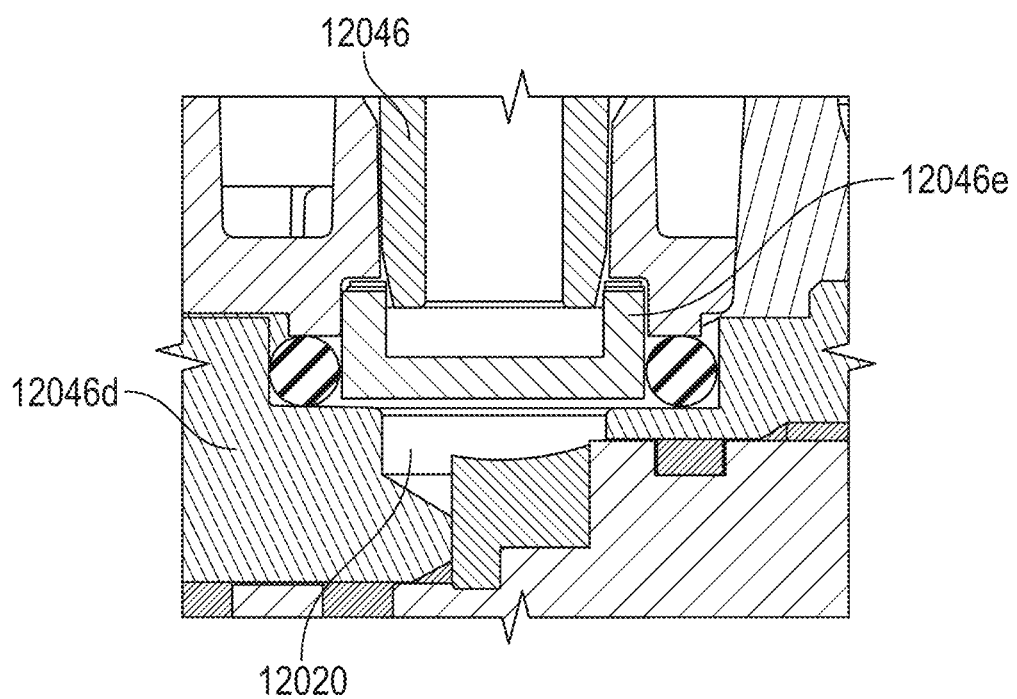
FIG. 48 is a partial sectional view of a filter extension duct and manifold outlet.

With reference to FIGS. 47 and 48, the manifold outlet 12046 may be provided with a filter 10246c to prevent, or at least minimise, bacteria, dust, and particulates from entering the manifold. A situation that may cause material to enter the manifold is when the filter module is disconnected from the apparatus, the valve module, or both. A similar filter could be additionally or alternatively placed at the manifold inlet for similar purposes.

In an embodiment, the filter 10246c may be or comprise a sintered metal filter. Examples of suitable sintered metals include copper, bronze, or steel. Alternatively, the filter may be a ceramic or polymeric filter, which may be sintered filters. Sintered metal filters provide long term reliability, and due to the proximity to the oxygen supply source the resulting pressure drop would not be prohibitive.

FIG. 47 shows a seal 12046a in the form of an O-ring between the filter extension duct 12046 and the filter and/or manifold outlet. Other appropriate seals may be used, such as a grommet seal, or a face seal. Additionally, or alternatively, the filter extension duct could seal with the manifold through an interference fit, as shown in FIG. 48, or a tight clearance fit.

In addition to any of these embodiments, the filter could be sealed to the manifold outlet by an O-ring seal, a grommet seal, a face seal, and/or any other suitable seal. Alternatively, the lower seal may not be present.

The valve carrier 9051 comprises a speaker housing 9065 and an audio speaker 9066 located and retained in the speaker housing. The speaker is in electronic communication with the control system of the apparatus 10.

Figure 52:
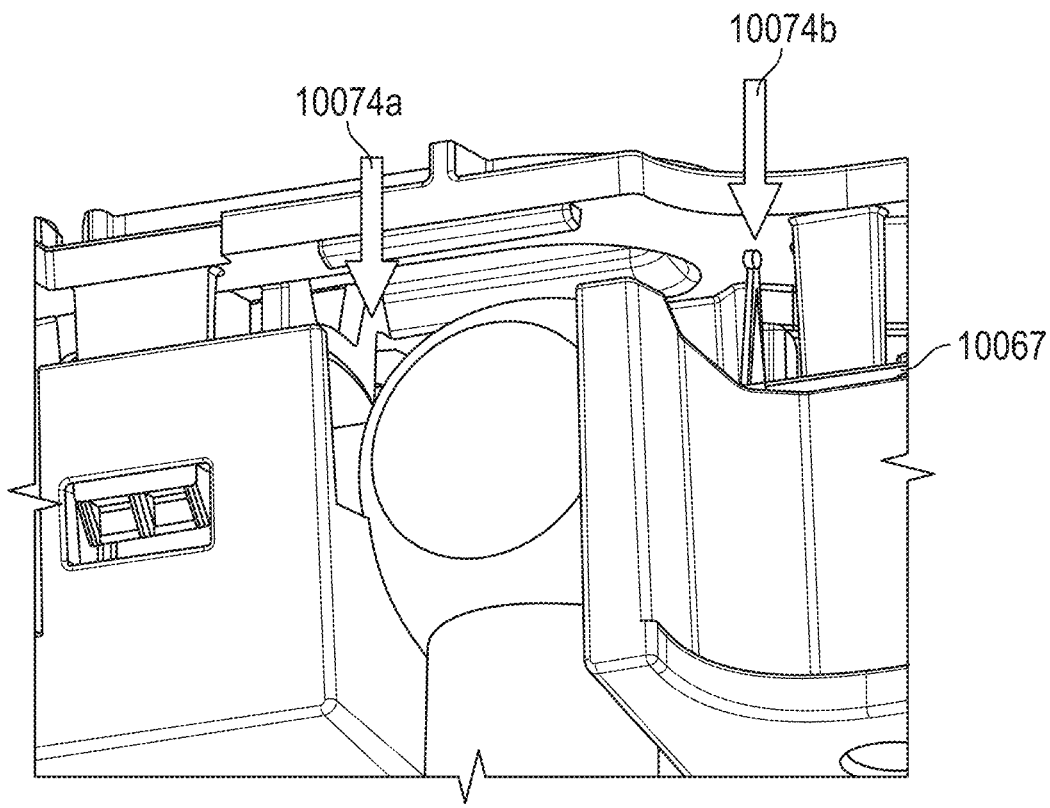
FIG. 52 is an underside perspective view of a valve module showing the location of temperature sensor(s).

One or more temperature sensor(s) is/are provided on or in the valve carrier 9051, such as in the vicinity of the speaker. In some configurations, the temperature sensor(s) comprises a thermistor, a digital temperature sensor, or any other suitable type of temperature sensor. The temperature sensor(s) provides ambient temperature feedback to a controller of the apparatus, indicative of the ambient temperature external to the apparatus 10. The temperature sensor(s) is/are preferably positioned in a gases stream. For example, the temperature sensor(s) may be positioned in the gas ambient air flow path. Additionally, or alternatively, the temperature sensor(s) is/are positioned near the edge of the unit. These positions eliminate, or at least reduce, the effect of the heat generated within the unit on the temperature sensed by the temperature sensors and allows the temperature sensor(s) to detect a temperature that is close to the ambient temperature. In one embodiment, a temperature sensor is near the inlet. FIG. 52 shows two options for the position of the sensor, indicated by arrows. The arrow on the right indicates the temperature sensor being located on an extension 10074 of a flexible PCB 10067, which is described below. The apparatus may have one temperature sensor positioned at one location, one temperature sensor at the other location, or two temperature sensors: one positioned at each both locations. In other alternatives, the sensor or sensors may be positioned in other locations on the apparatus.

The upper valve carrier part 9055 has the effect of 'sandwiching' the valve 9003, valve manifold 9011, and speaker 9066 in place on the valve carrier 9051. Specifically, the upper valve carrier part 9055 supports the valve 9003, valve manifold 9011 and speaker 9066 from above. This assists in the assembly of the valve module 9001 and in retaining all components together as a complete module during transport. Sleeves 9060 are provided in the upper carrier part to receive fasteners from sleeves 9059 in the lower carrier part.

In some configurations, the upper valve carrier part 9055 and lower valve carrier part 9053 may be integrally formed as a unitary item.

The valve module 9001 has an electrical connector to provide an electrical connection between the valve module and the apparatus 10 for delivering a flow of gas, to provide modularity of the valve module. In some configurations, the electrical connector is in electric/electronic communication with the valve 9003, and the electrical connector is arranged or adapted to engage with a complementary connector in the apparatus 10 for delivering a flow of gas; for example by plugging into the complementary connector. In some configurations, wires provide the electrical/electronic communication between the valve and the electrical connector. In some configurations, grommets provide a seal between the wires and an opening that the wires pass through, and shield the wires from contact with the edges of the opening that the wires pass through. In the form shown, the upper valve carrier part 9055 has an electrical connector, such as a PCB 9067, extending therethrough. The PCB 9067 is part of the lower chassis 202 of the apparatus 10, and couples with a PCB edge connector in the valve carrier 9051 so that the PCB 9067 is in electronic communication with the valve 9003, temperature sensor, and speaker 9066, and so that the valve module 9001 and apparatus 10 are in electronic communication. The PCB 9067 is orientated vertically. Alternatively, the PCB 9067 may be provided in the valve module, and the PCB may project from a housing of the valve carrier to engage with a complementary edge connector internal to the apparatus 10, such that the valve module 9001 and apparatus 10 control system are in electronic communication.

While the electrical connector is shown as being accessible from the top of the valve carrier, in some configurations, the electrical connector may be positioned in, or accessible from, a top, side, or base of the valve carrier.

Figure 44:
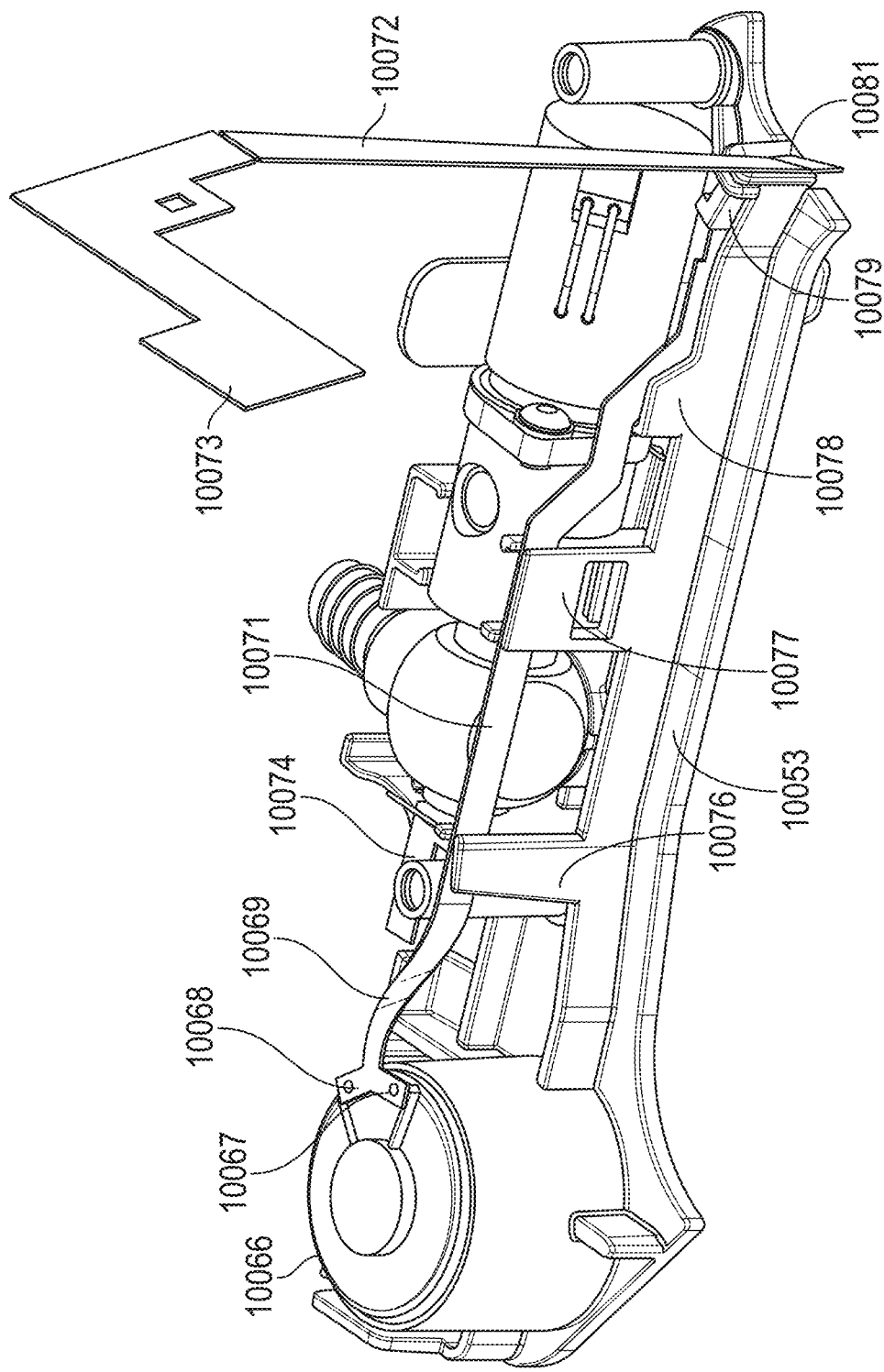
FIG. 44 is a view similar to FIG. 43, but viewed from the other side, with the upper valve carrier part removed.
Figure 45:
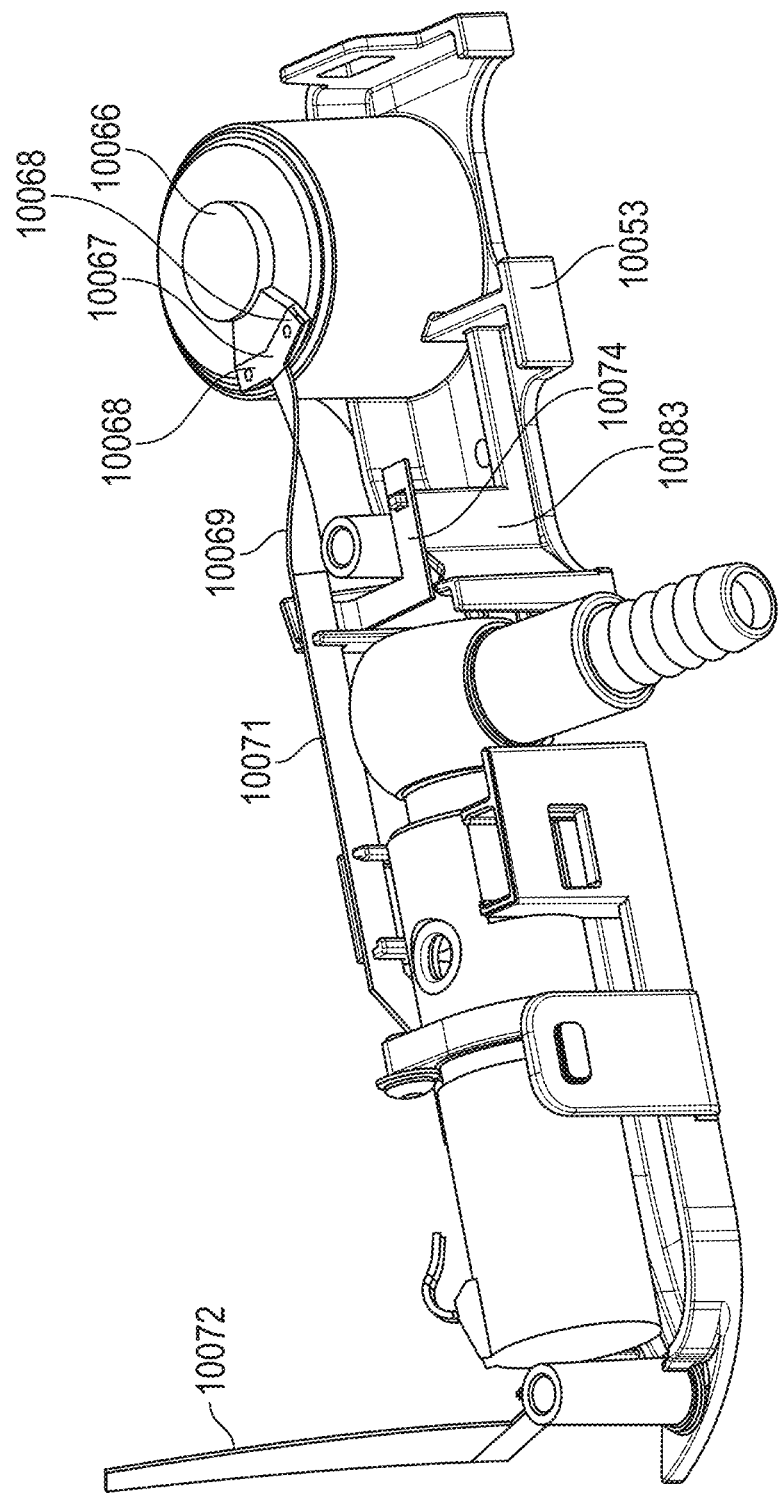
FIG. 45 is a view similar to FIG. 43 with the upper valve carrier part removed.

FIGS. 43 to 45 show an alternative configuration of the valve module. Unless described below, the features, functionality, options, and advantages are all as outlined above for the first valve module configuration above, and like reference numerals indicate like parts with 9000 added to each numeral.

In particular, this alternative embodiment has a flexible PCB 10067. The flexible PCB 10067 is a ribbon having a width, a relatively thin depth, and a relatively long length. The flexible PCB 10067 is a flexible plastic substrate, such as polyimide, and contains a plurality of parallel tracks that electronically connect the components. The flexible PCB 10067 is in electronic communication with the valve 10003, temperature sensor and speaker 10066, so that the valve module and apparatus 10 are in electronic communication.

The flexible PCB 10067 has two outwardly extending tabs 10068 that electronically connect to the speaker 10066. The flexible PCB 10067 could have a differently shaped end to connect to the speaker 10066. The shape of the end of the flexible PCB 10067 will be chosen or designed depending on the shape of the speaker, other components, or the necessary connection of the flexible PCB.

The end of the flexible PCB 10067 adjacent the speaker is oriented with the width of the ribbon extending horizontally. Extending from the speaker, the flexible PCB 10067 then twists from the horizontal orientation to a vertical orientation in which the width of the ribbon is now oriented vertically. The vertically oriented section of the flexible PCB 10067 is supported in stands 10076, 10077, and 10078 of the lower valve carrier part 10053. The flexible PCB 10067 is shaped with two steps, with ramps between the steps. The shape and orientation of the flexible PCB 10067 reduces the space required for the flexible PCB 10067.

The next portion 10072 of the flexible PCB 10067 extends vertically; that is, the ribbon is oriented with the length extending vertically. This portion 10072 and has a slight twist. The end 10073 of the flexible PCB 10067 electronically connects to the apparatus 10 control system.

The flexible PCB 10057 also includes an extension 10074 that connects to the temperature sensor. The extension 10074 is an L-shaped extension with the width of the ribbon oriented horizontally. The shape and orientation of the extension 10074 will be chosen or designed depending on the relative position of the components. The extension 10074 is oriented to lie horizontally and is supported by a stand of the lower valve carrier part 10053.

The shape and configuration of the flexible PCB 10067 is chosen or designed to fit around the other components and to ensure the flexible PCB 10067 is supported. It will be appreciated that the shape and/or configuration can be modified depending on the shape, size, and/or orientation of the other components.

FIG. 43 shows an alternative embodiment of the upper valve carrier part 10055 having a spacer 10080 to assist with securing the speaker 10066 rigidly. The spacer 10080 contacts the components above and prevents the upper valve carrier part 10055 from moving, such as flexing. In particular, the spacer 10080 extends upwardly from the upper valve carrier part 10055. The spacer 10080 prevents, or at least substantially inhibits, the speaker 10066 from moving relative to the other components during transport.

Figure 49:
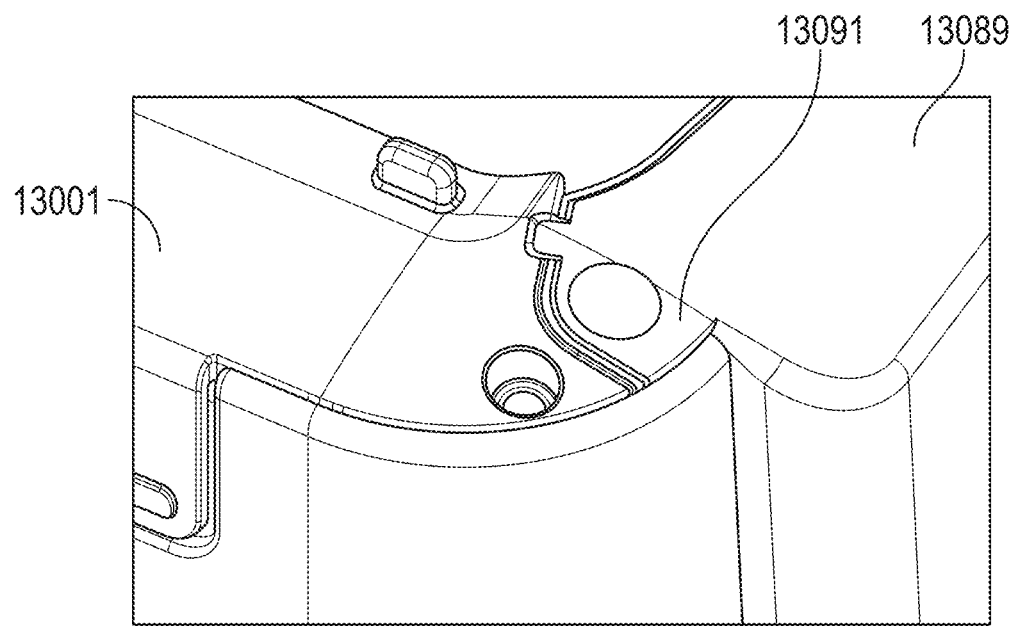
FIG. 49 is a partial underside view of a battery cover and valve module.

In some configurations, the location of the wires or flexible PCB may result in a grommet being located between the valve module 9001 and a removable battery pack 13089, shown in FIG. 49. With reference to the grommet 10079 in FIG. 44, the grommet 10079 engages the battery cover when assembled. During disassembly, the grommet 10079 will disengage with whichever module is removed first. If the valve module 9001 is removed first, the grommet 10079 will remain with the battery pack 13089. In this case, the wires or flexible PCB will be pulled through the grommet 10079. When the device is reassembled, the wires or flexible PCB strip will need to be pulled back through the grommet 10079. It is preferable for the battery pack 13089 to be removed before the valve module 9001. To ensure disassembly is done in this order, the battery pack 13089 has a lip or small extension on the case that extends over the valve module 9001. The lip prevents the valve module 9001 from being removed before the battery is removed.

Figure 57:
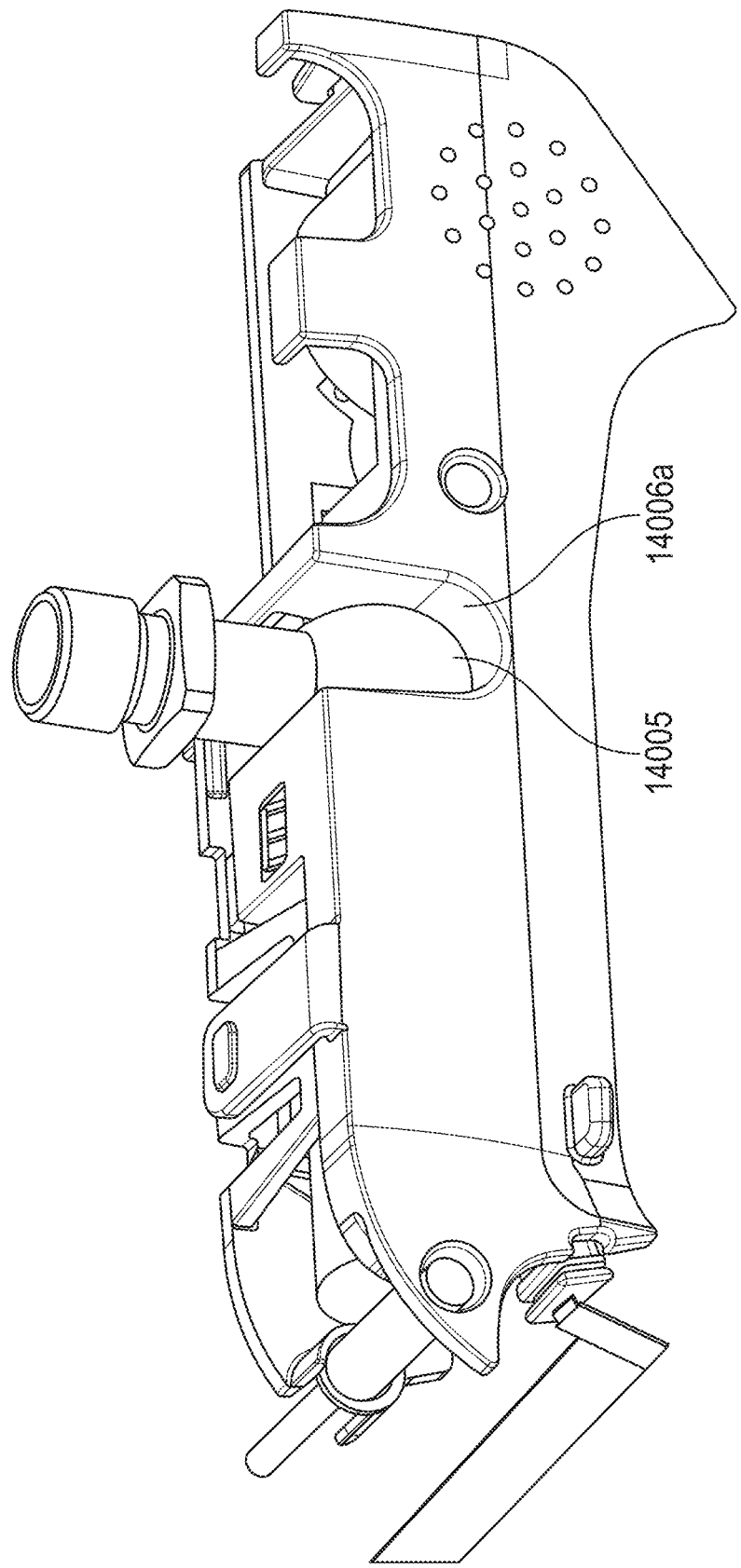
FIG. 57 is an underside view of the valve module of FIG. 56.
Figure 58:
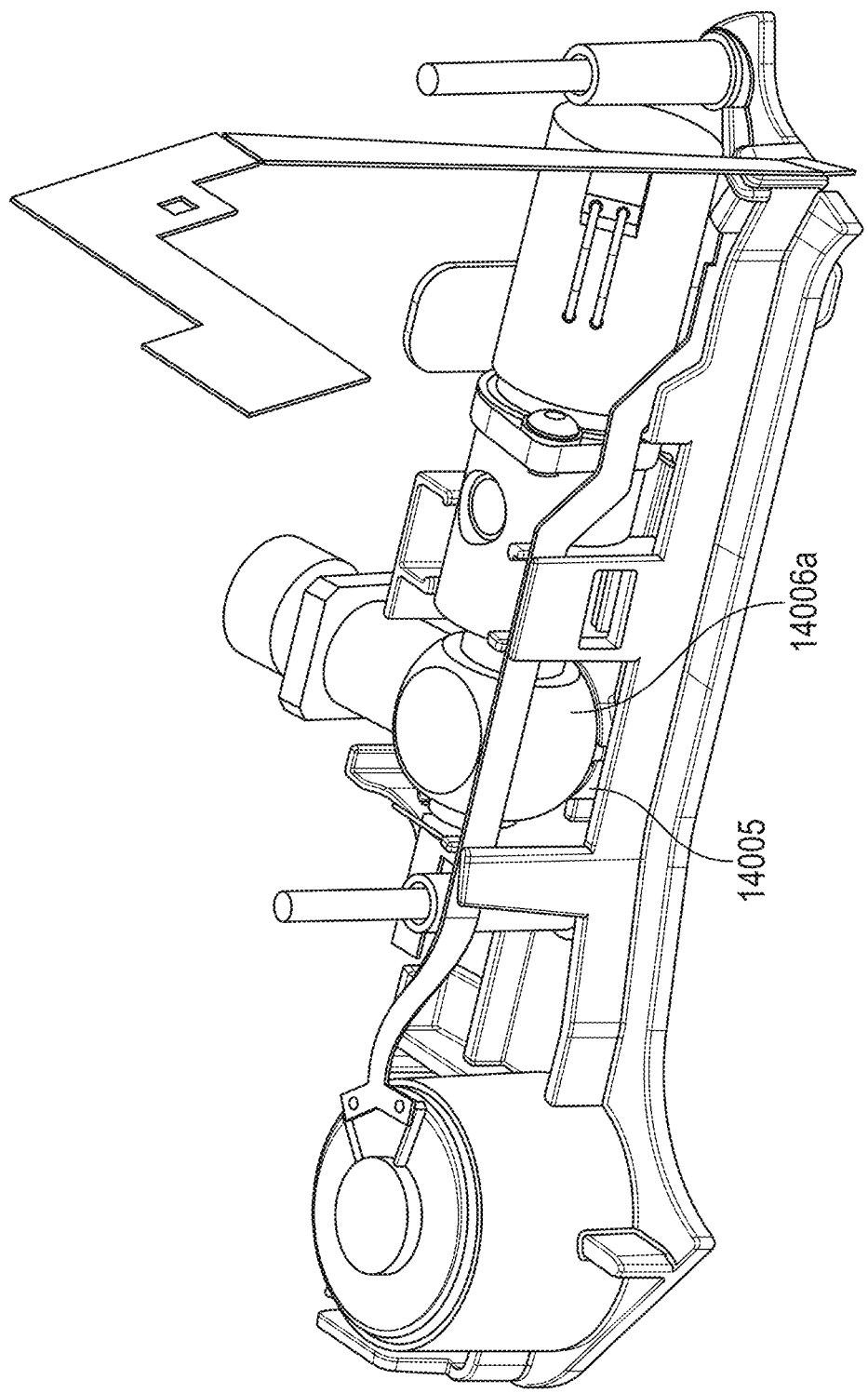
FIG. 58 is another perspective view of the valve module of FIG. 56.

FIGS. 52, and 56 to 58 show a variation of the embodiment of FIGS. 43 to 45. In this embodiment, the swivel connector is a ball joint 14005. As described in relation to other embodiments, the swivel connector is a ball joint for providing rotation in multiple directions. In this embodiment, the ball joint 14005 will pivot about a single axis of rotation. This arrangement provides a tight fit between the valve carrier and the swivel connector regardless of the position of the swivel connector. This prevents, or at least substantially inhibits oxygen from leaking into the underside of the apparatus, and instead directs it out around the swivel connector. The valve carrier has a cup shaped surface 14006a to receive the ball of the swivel joint. In this embodiment, ambient air is drawn through one or more gaps that occur when the valve carrier is assembled. This is shown in FIG. 57.

Figure 34:
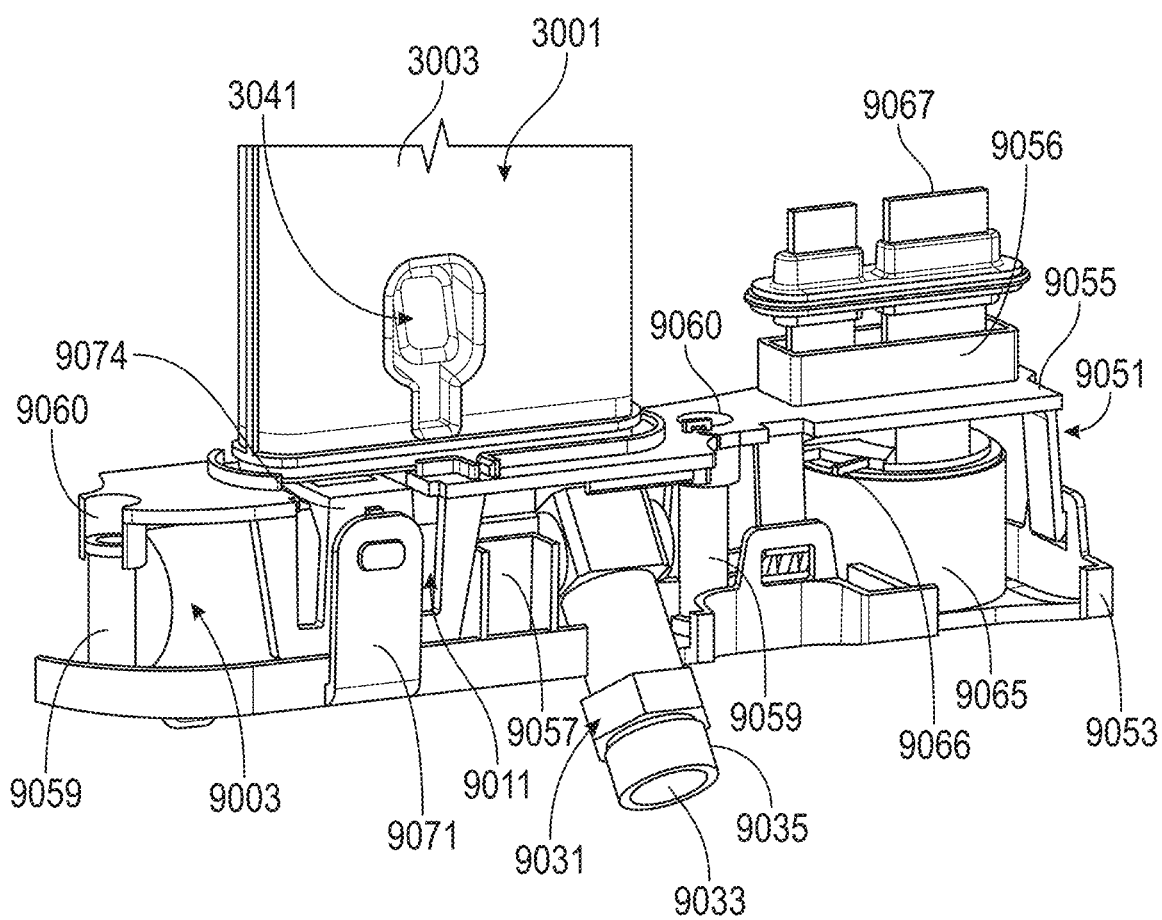
FIG. 34 is a rear side overhead perspective view or the third configuration filter module and sixth configuration valve module including a valve carrier top panel.
Figure 35:
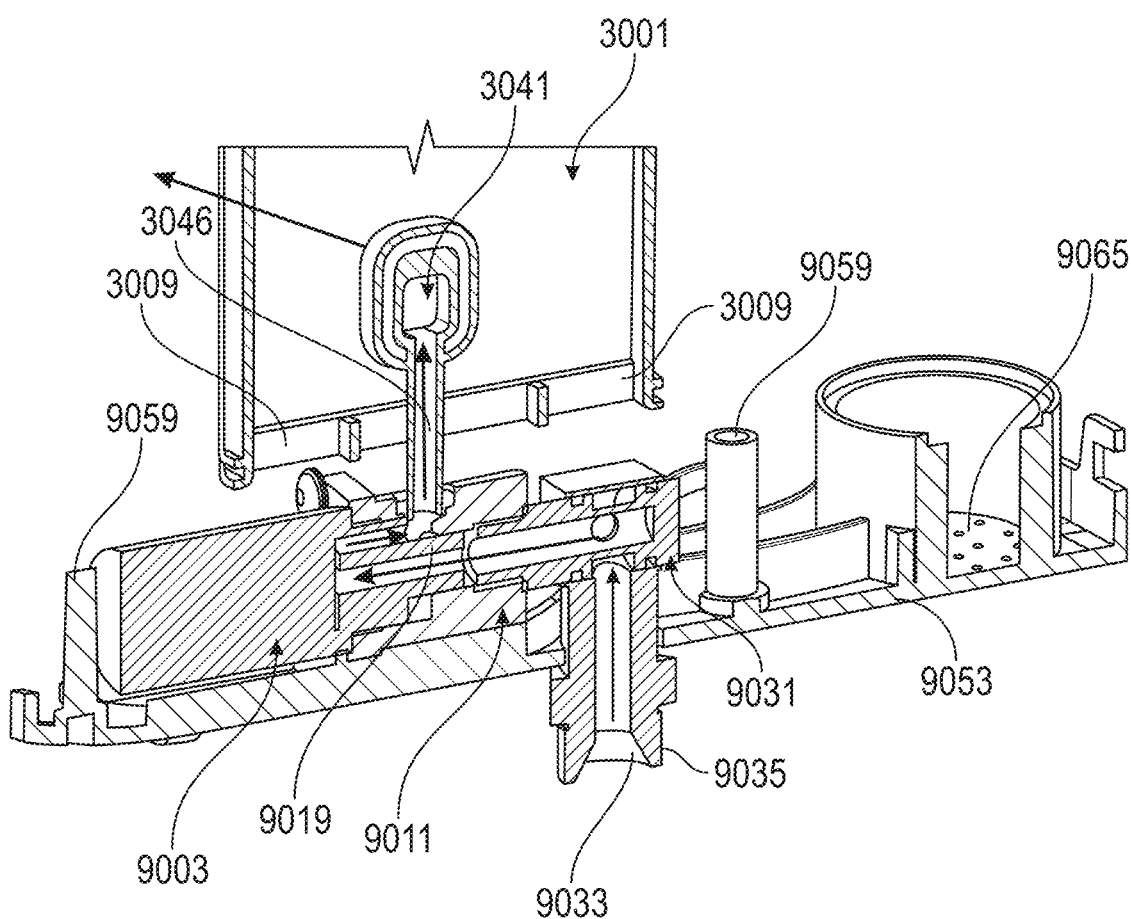
FIG. 35 is a sectional view of part of the sixth configuration valve module and part of the third configuration filter module, showing the gas flow path of oxygen (or another gas) through the valve module and filter module.
Figure 36:
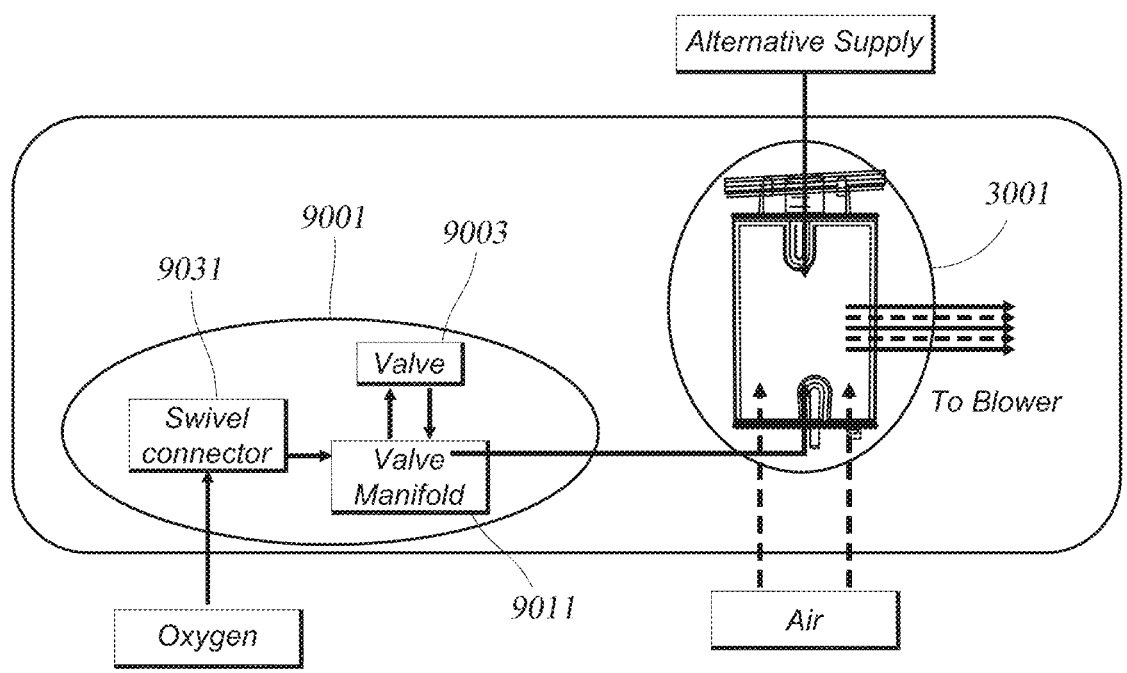
FIG. 36 is a schematic gas flow path diagram for the sixth configuration valve module and the third configuration filter module, with the solid line arrows representing the flow of oxygen (or another gas), and the dashed line arrows representing the flow of ambient air.

With reference to FIG. 34, the top panel further includes an intermediary filter clip 9074. Pressing the filter module release tab 9071, located on the lower part 9053 of the valve carrier, displaces the intermediary filter clip 9074 to clear the projection on the filter engagement tab 3071 (FIGS. 38 and 39), and enables the filter 3001 to be withdrawn from the apparatus housing.

The filter module engagement tab 3071 includes an aperture therethrough. The intermediary filter clip 9074 (see FIG. 34) includes an aperture with an internal projection.

When the intermediary filter clip 9074 is depressed, the filter module engagement tab 3071 is allowed to pass into the aperture of the intermediary filter clip 9074. When the intermediary filter is released (i.e. not depressed), the internal projection of the intermediary filter clip passes through and engages the aperture in the filter module engagement tab 3071.

This secures the filter module 9001 in place. This prevents accidental removal in the event that a tube attached to alternative gas supply connector 1039/3039 is pulled.

In this configuration, oxygen entrainment in the air flow is enhanced by the filter extension duct receiving oxygen from the valve assembly.

Portion 9035 of the swivel connector protrudes from the apparatus housing near the point at which the apparatus 10 is mounted to a pole stand. The position of the swivel connector, therefore, enables positioning of the gas supply line such that it may run substantially adjacent the pole of the pole mount. This may avoid the gas supply line extending substantially away from the pole stand such that it may catch or drag on nearby objects. This may also avoid kinking of the gas supply line.

Because the gases inlets 4033, 5015, 6015, 7033, 8033, 9033 of the valve modules 4001, 5001, 6001, 7001, 8001, 9001 can move relative to the housing of the apparatus 10, the apparatus 10 can be placed (for example on a surface or pole mount or bracket) without kinking or damaging a coupled gases line, which could compromise the gas supply to a patient. This provides enhanced flexibility of positioning of the apparatus.

The valve modules and filter modules described herein are an open system—as a result, some oxygen may be lost, or leak, from the system. The apparatus 10 is advantageously capable of delivering approximately 100% concentration of oxygen to a patient where required. The apparatus 10 using the valve modules and filter modules may be able to deliver gases with between about 21% and about 100% oxygen concentration to a patient, as required. As the filter is open to ambient air, oxygen from the valve manifold displaces air from the system. For example, a greater supply of oxygen displaces a greater amount of air, resulting in a greater proportion of oxygen entering the system.

The filter modules and valve modules described herein may provide varying gas flow paths for the apparatus. For example, the valve module may control the flow of oxygen entering the gas flow path of the apparatus, via the valve module and filter module. Alternatively, the valve module may be bypassed by means of direct connection of an alternative oxygen source to the filter module by the first sub-compartment gases inlet (inlet 1011 of FIG. 10 for example). This may be practical in circumstances where a user may wish to manually adjust the oxygen supply (i.e. such as by the wall supply rotameter).

It will be appreciated that the filter modules and the valve modules described herein may be used separately in apparatuses for delivering a flow of gas. Alternatively, the filter and the valve module may be used together as a filer and valve assembly for improved functionality.

In the configurations shown, the apparatus 10 receives oxygen by at least one of the following:

via the valve module (for automatic oxygen regulation by the apparatus), or via the alternative gases inlet provided on the top of the filter (allowing attachment of a manually adjustable oxygen supply—i.e. such as by the wall supply rotameter).

A further alternate flow path configuration is envisaged in which either a source of pressurised oxygen or a manually adjustable oxygen supply connects to a single gases inlet via the valve module 4001, 5001, 6001, 7001, 8001, 9001. As a result, all oxygen supply would pass through the valve module. Such a configuration is shown schematically in FIG. 42.

In this configuration, where attachment of a manually adjusted oxygen supply 21 is required, the apparatus is set to a 'manual supply' mode. In this mode, the oxygen valve is held open in a non-active, non-regulating, state—allowing oxygen to pass through freely.

Alternatively, the valve employed in the valve module could be of the 'normally open' type. When the apparatus is set to a 'manual supply' mode, the valve is simply powered off—allowing oxygen to pass through freely.

The manually adjusted oxygen supply 21 may be manually controlled by a user via an external flow controller 22, such as a wall supply rotameter or gas tank valve for example.

Figure 42:
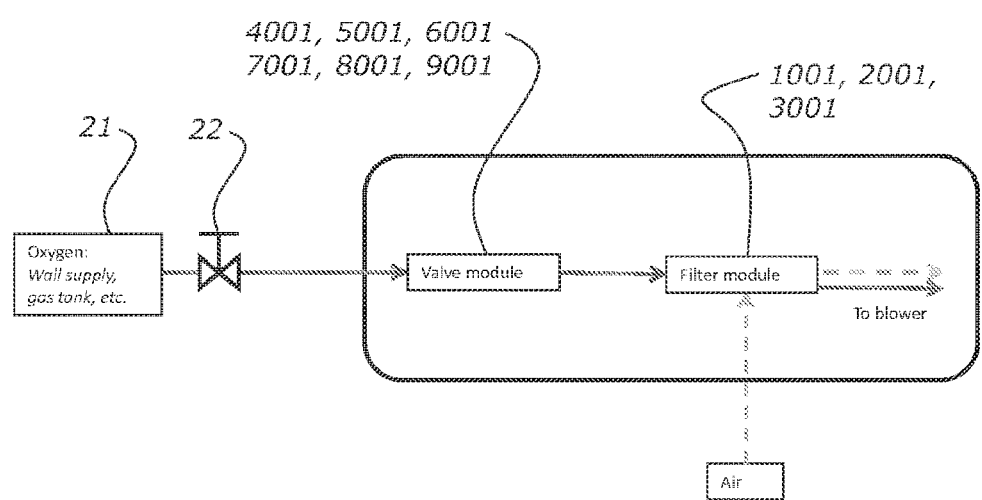
FIG. 42 is an alternative schematic gas flow path diagram for one of the valve modules and one of the filter modules, with the solid line arrows representing the flow of oxygen (or another gas), and the dashed line arrows representing the flow of ambient air.

The configuration of FIG. 42 eliminates the separate alternative oxygen inlet, which bypasses the valve. As a result, the filter body would only require a single, main chamber and the top panel could be more readily integrally mouldable with the filter unit—thereby simplifying manufacture.

This configuration also provides the apparatus 10 a capacity to shut-off or control the manually adjusted oxygen supply in exceptional or unsafe circumstances—such as excessive pressure or if the patient was to become hyperoxic (excess blood oxygen retention).

The apparatus 10 may be provided with or without the valve module 4001, 5001, 6001, 7001, 8001, 9001. For example, for some home use applications, the user may not require supplemental oxygen, but may benefit from high flow therapy. For such applications, the valve module housing 306 of the apparatus 10 may be provided with a cover that ambient air can pass through (via apertures) or around, or may be uncovered. This would reduce the overall cost of the apparatus.

With that configuration, if supplemental manually adjusted oxygen is required, that can be connected via the alternative gas supply inlet 1011, 2011, 3011 on the top of the filter 1001, 2001, 3001, 11001.

The various configurations described are exemplary configurations only. Any one or more features from any of the configurations may be used in combination with any one or more features from any of the other configurations.

For example, the swivel connector used in the valve module may have additional functionality. In some configurations, the swivel connector may be arranged to swivel about more than one axis; and may for example have two adjacent swivel connection portions with swivel axes that are transverse to each other, so that the gases inlet of the swivel connector can rotate around the two axes. In some configurations, the swivel connector may comprise a ball and socket arrangement or similar, to enable the gases inlet of the swivel connector to rotate in substantially any direction. In some configurations, the swivel connector may be arranged to provide both swivelling and translational movement; so that the gases inlet of the swivel connector may both swivel about one or more axes and may also travel linearly for example. This may be practical for translating the gases inlet from one portion of the apparatus to another, such as from one side of the apparatus to the other of the apparatus for example. In some configurations, the gases inlet may be arranged to translate instead of rotate.

As another example, while the motor and/or sensor sub-assembly recess is described as being in the underside of the main housing, it could alternatively be in a rear, side, front, or top of the housing. With such a variant, the air and/or oxygen inlets may also be positioned differently as required.

As another example, rather than the liquid chamber and chamber bay being configured so that the liquid chamber is inserted into and removed from the chamber bay from a front of the housing, the configuration could be such that the liquid chamber is inserted into and removed from the chamber bay from a side, rear, or top of the housing.

As another example, while the filter modules are described as being inserted into the housing from above and the valve modules inserted into the housing from below, either or both of those components could be inserted into any suitable part of the housing, such as an upper part, lower part, side part, front part, or rear part.

The valve modules may be used together with the filter modules as a filter and valve assembly. Alternatively, only the filter module may be used in an apparatus or only the valve module may be used in an apparatus. For example, the valve module may not be used where a user does not require supplemental oxygen, but would still benefit from high flow therapy. The user may still have the option of connecting an external oxygen supply by means of direct connection to the filter module.

The filter module and valve module are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the filter module and/or valve module may be used in an apparatus for a different purpose. The apparatus may be a high flow therapy apparatus, or may be a low flow therapy apparatus. The features may also be provided in an apparatus for providing continuous positive airway pressure (CPAP), which may deliver gases (humidified or otherwise) at positive pressure.

The filter module and/or valve module may alternatively be used with an apparatus that does not require a humidifier and therefore does not require the liquid chamber 300 or chamber bay 108 features. For example, it will be appreciated that the configuration that isolates the motor and gas flow path from the electrical and electronic components has broad applications in other types of gas delivery apparatuses.

The 'flow therapy apparatus' language is intended to cover all such variants.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to when the apparatus is in a typical in-use position, and are used to show and/or describe relative directions or orientations.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The invention claimed is:

1. A filter for an apparatus for delivering a flow of gas, the filter comprising:
 a filter body, wherein the filter body has a main compartment and a sub-compartment at least partly within the main compartment, wherein the main compartment is in fluid communication with a main compartment gases inlet and the sub-compartment is in fluid communication with a sub-compartment gases inlet, the sub-compartment comprising at least one sub-compartment wall that provides a barrier to direct all gases from the sub-compartment gases inlet through a sub-compartment gases outlet;
 a filter medium associated with both the main compartment and the sub-compartment, and that is arranged to filter gases in, or exiting, the main compartment and the sub-compartment;
 wherein a direction of gas flow through a main compartment gases outlet is generally transverse to a direction of gas flow through the main compartment gases inlet;
 wherein a direction of gas flow through the sub-compartment gases outlet is generally transverse to a direction of gas flow through the sub-compartment gases inlet; and
 wherein the main compartment gases inlet and the sub-compartment gases inlet provide separate inlets into the filter body.

2. The filter of claim 1, wherein the filter is a filter module that is removably and sealably engageable with a housing of the apparatus for delivering a flow of gas.

3. The filter of claim 2, wherein the filter has a filter engagement tab configured to engage a retention block of the apparatus for securing the filter.

4. The filter of claim 2, comprising at least one seal extending about an external periphery of the filter to sealingly engage the filter in the housing of the apparatus.

5. The filter of claim 4, wherein the at least one seal comprises one or more O-rings or one or more integrally formed wiper seals.

6. The filter of claim 1, wherein the main compartment is defined by at least one main compartment wall bounding a main compartment volume.

7. The filter of claim 6, wherein the sub-compartment is defined by the at least one sub-compartment wall bounding a sub-compartment volume at least partly within the main compartment volume.

8. The filter of claim 7, wherein the filter medium is ultrasonically welded to the at least one main compartment wall and the at least one sub-compartment wall.

9. The filter of claim 1, comprising a second sub-compartment at least partly within the main compartment, wherein the second sub-compartment is arranged to receive gas from a second sub-compartment gases inlet.

10. The filter of claim 1, wherein the filter medium comprises substantially a same material as the filter body.

11. The filter of claim 1, wherein the filter body comprises a polymeric material, and wherein the filter medium comprises polymeric or synthetic material(s), and/or wool fibres.

12. The filter of claim 1, comprising a second sub-compartment at least partly within the main compartment, wherein the second sub-compartment is arranged to receive gas from a second sub-compartment gases inlet, and wherein a duct is provided in fluid communication with the second sub-compartment.

13. The filter of claim 1, wherein the sub-compartment gases outlet is arranged so that gases exit the sub-compartment in the direction of gas flow that is offset from an axis of the sub-compartment gases inlet.

14. The filter of claim 1, wherein the sub-compartment is configured to receive gases from an alternative supply to that of the main compartment.

15. The filter of claim 1, wherein the main compartment is configured to receive a flow of ambient air.

16. The filter of claim 1, wherein the sub-compartment is configured to receive a flow of oxygen.

17. The filter of claim 1, wherein the sub-compartment gases inlet receives a flow of gas from a hospital wall supply rotameter, a gas tank, or from an oxygen concentrator.

18. The filter of claim 1, wherein an alternative gas supply connector is in fluid communication with the sub-compartment, and wherein the alternative gas supply connector is an elongate tapering connector suitable for releasably connecting semi-rigid gas supply tubes.

19. The filter of claim 1, wherein at least a portion of the main compartment tapers inwardly.

20. The filter of claim 1, wherein at least a first portion of the sub-compartment spaced further from the sub-compartment gases inlet has a smaller dimension than a second portion of the sub-compartment adjacent the sub-compartment gases inlet.

21. The filter of claim 1, wherein the at least one sub-compartment wall is positioned within the main compartment.

22. A filter for an apparatus for delivering a flow of gas, the filter comprising:
  a filter body, wherein the filter body has a main compartment and a sub-compartment at least partly within the main compartment, wherein the main compartment is in fluid communication with a main compartment gases inlet and the sub-compartment is in fluid communication with a sub-compartment gases inlet, the sub-compartment comprising walls that provide a barrier to direct all gases from the sub-compartment gases inlet through a sub-compartment gases outlet; and
  a filter medium associated with both the main compartment and the sub-compartment, and that is arranged to filter gases in, or exiting, the main compartment and the sub-compartment,
  wherein the main compartment inlet is on a first side of the filter body,
  wherein the sub-compartment inlet is on a second side of the filter body,
  wherein the first side is opposite the second side along a longitudinal axis of the filter body, and
  wherein the sub-compartment walls extend within the main compartment and extend from the sub-compartment gases inlet.

23. The filter of claim 22, further comprising a second sub-compartment at least partly within the main compartment, wherein the second sub-compartment is arranged to receive gas from a second sub-compartment gases inlet.

24. The filter of claim 23, wherein the second sub-compartment comprises walls that provide a barrier to direct all gases from the second sub-compartment gases inlet through a second sub-compartment gases outlet.

25. The filter of claim 23, wherein the second sub-compartment inlet is on the first side of the filter body.

26. The filter of claim 22, wherein the sub-compartment walls are positioned within the main compartment.

* * * * *

UNITED STATES PATENT AND TRADEMARK OFFICE
CERTIFICATE OF CORRECTION

PATENT NO. : 11,202,878 B2
APPLICATION NO. : 16/342472
DATED : December 21, 2021
INVENTOR(S) : Andre Van Schalkwyk It is certified that error appears in the above-identified patent and that said Letters Patent is hereby corrected as shown below:

In the Specification

In Column 7, Line 35, delete "Hoe," and insert --line,--.

In Column 8, Line 38, delete "through" and insert --or through--.

In Column 8, Line 60, delete "pas" and insert --gas--.

In Column 10, Line 38, delete "sub-compartments)," and insert --sub-compartment(s),--.

In Column 18, Line 47, delete "how" and insert --flow--.

In Column 22, Line 38, delete "or" and insert --of--.

In Column 24, Line 2, delete "beat" and insert --heat--.

In Column 31, Line 14 (Approx.), delete "cuter" and insert --outer--.

In Column 34, Line 35, delete "pas" and insert --gas--.

In Column 34, Line 48, delete "5001," and insert --6001,--.

In Column 35, Line 29, delete "cut" and insert --out--.

In Column 35, Line 32, delete "cases" and insert --gases--.

In Column 37, Line 27, delete "flit," and insert --fit,--.

In Column 41, Line 53, delete "walk" and insert --walls--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,202,878 B2

In Column 48, Line 11, delete "cutlets," and insert --outlets,--.

In Column 52, Line 9, delete "a such" and insert --such--.

In Column 53, Line 27, delete "8501." and insert --8601.--.

In Column 56, Line 3, delete "10057" and insert --10067--.